US011512297B2

(12) United States Patent
Garst et al.

(10) Patent No.: US 11,512,297 B2
(45) Date of Patent: Nov. 29, 2022

(54) AFFINITY TAG FOR RECOMBINATION PROTEIN RECRUITMENT

(71) Applicant: Inscripta, Inc., Boulder, CO (US)

(72) Inventors: Andrew Garst, Boulder, CO (US); Tian Tian, Boulder, CO (US); Daniel Held, Boulder, CO (US)

(73) Assignee: Inscripta, Inc., Boulder, CO (US)

( * ) Notice: Subject to any disclaimer, the term of this patent is extended or adjusted under 35 U.S.C. 154(b) by 0 days.

(21) Appl. No.: 17/522,399

(22) Filed: Nov. 9, 2021

(65) Prior Publication Data

US 2022/0145277 A1 May 12, 2022

Related U.S. Application Data

(60) Provisional application No. 63/111,495, filed on Nov. 9, 2020.

(51) Int. Cl.
  *C12N 9/22* (2006.01)
  *C12N 15/11* (2006.01)
  *C12N 15/90* (2006.01)

(52) U.S. Cl.
  CPC .............. *C12N 9/22* (2013.01); *C12N 15/11* (2013.01); *C12N 15/902* (2013.01); *C12N 15/905* (2013.01); *C12N 15/907* (2013.01); *C07K 2319/00* (2013.01); *C12N 2310/20* (2017.05); *C12N 2800/80* (2013.01)

(58) Field of Classification Search
  CPC ........ C12N 9/22; C12N 15/11; C12N 15/902; C12N 15/905; C12N 15/907; C12N 2310/20; C12N 2800/80; C07K 2319/00
  See application file for complete search history.

(56) References Cited

U.S. PATENT DOCUMENTS

| | | | |
|---|---|---|---|
| 6,391,582 B2 | 5/2002 | Ying et al. | |
| 6,837,995 B1 | 1/2005 | Vassarotti et al. | |
| 7,166,443 B2 | 1/2007 | Walker et al. | |
| 8,332,160 B1 | 12/2012 | Platt et al. | |
| 8,697,359 B1 | 4/2014 | Zhang et al. | |
| 8,926,977 B2 | 1/2015 | Miller et al. | |
| 9,260,505 B2 | 2/2016 | Weir et al. | |
| 9,361,427 B2 | 6/2016 | Hillson | |
| 9,499,855 B2 | 11/2016 | Hyde et al. | |
| 9,776,138 B2 | 10/2017 | Innings et al. | |
| 9,790,490 B2 | 10/2017 | Zhang et al. | |
| 9,896,696 B2 | 2/2018 | Begemann et al. | |
| 9,982,279 B1 | 5/2018 | Gill et al. | |
| 9,988,624 B2 | 6/2018 | Serber et al. | |
| 10,011,849 B1 | 7/2018 | Gill et al. | |
| 10,017,760 B2 | 7/2018 | Gill et al. | |
| 10,227,576 B1 | 3/2019 | Cameron et al. | |
| 10,266,851 B2 | 4/2019 | Chen | |
| 10,704,033 B1 | 7/2020 | Kim et al. | |
| 10,724,021 B1 | 7/2020 | Kim et al. | |
| 10,745,678 B1 | 8/2020 | Kim et al. | |
| 10,767,169 B1 | 9/2020 | Kim et al. | |
| 10,837,021 B1 | 11/2020 | Tian et al. | |
| 10,927,385 B2 | 2/2021 | Kannan et al. | |
| 2002/0139741 A1 | 10/2002 | Kopf | |
| 2004/0110253 A1 | 6/2004 | Kappler et al. | |
| 2006/0014137 A1 | 1/2006 | Ghosh et al. | |
| 2007/0020761 A1 | 1/2007 | Yu | |
| 2010/0076057 A1 | 3/2010 | Sontheimer et al. | |
| 2011/0294217 A1 | 12/2011 | McConnell-Smith et al. | |
| 2013/0236970 A1 | 9/2013 | Anneren et al. | |
| 2014/0068797 A1 | 3/2014 | Doudna et al. | |
| 2014/0199767 A1 | 7/2014 | Barrangou et al. | |
| 2014/0242033 A1 | 8/2014 | Gruber et al. | |
| 2014/0273226 A1 | 9/2014 | Wu et al. | |
| 2015/0024464 A1 | 1/2015 | Lippow et al. | |
| 2015/0071898 A1 | 3/2015 | Liu et al. | |
| 2015/0098954 A1 | 4/2015 | Hyde et al. | |
| 2015/0159174 A1 | 6/2015 | Frendewey et al. | |
| 2015/0176013 A1 | 6/2015 | Musunuru et al. | |
| 2015/0191719 A1 | 7/2015 | Hudson et al. | |

(Continued)

FOREIGN PATENT DOCUMENTS

| | | |
|---|---|---|
| EP | 2395087 | 12/2011 |
| EP | 3199632 | 8/2017 |

(Continued)

OTHER PUBLICATIONS

Chang et al., New logic facilitated identification of novel phage recombinase function units . bioRxiv, this version posted Apr. 10, 2019, pp. 1-30. (Year: 2019).*

Chang et al., The efficiency for recombineering is dependent on the source of the phage recombinase function unit. bioRxiv, this version posted Aug. 24, 2019, pp. 1-26. (Year: 2019).*

Stella et al., Conformational Activation Promotes CRISPR-Cas12a Catalysis and Resetting of the Endonuclease Activity. Cell, 2018, vol. 175: 1856-1871. (Year: 2018).*

Bao, et al., "Genome-scale engineering of *Saccharomyces cerevisiae* with single-nucleotide precision", Nature Biotechnology, doi:10.1038/nbt.4132, pp. 1-6 (May 7, 2018).

Dicarlo, et al., "Genome engineering in *Saccharomyces cervisiae* using CRISPR-Case systems", Nucleic Acids Research, 41(7):4336-43 (2013).

(Continued)

*Primary Examiner* — Ganapathirama Raghu
(74) *Attorney, Agent, or Firm* — Sarah Brashears

(57) ABSTRACT

The present disclosure provides compositions and methods to increase the percentage of edited cells in a cell population when employing nucleic-acid guided editing, as well as automated multi-module instruments for performing these methods. Specifically, the disclosure relates to methods, compositions, modules and automated multi-module cell processing instruments that increase the efficiency of nucleic acid-guided editing in a cell population using a nucleic acid nuclease (i.e., an RNA-guided nuclease or "RGN")/single-strand binding protein ("SSB") fusion system. The system leverages a single-strand binding protein (SSP) and single-strand DNA annealing protein ("SSAP") interactions to drive enhanced recruitment.

23 Claims, 27 Drawing Sheets

(56) References Cited

U.S. PATENT DOCUMENTS

| | | |
|---|---|---|
| 2015/0225732 A1 | 8/2015 | Williams et al. |
| 2015/0344549 A1 | 12/2015 | Muir et al. |
| 2016/0024529 A1 | 1/2016 | Carstens et al. |
| 2016/0053272 A1 | 2/2016 | Wurzel et al. |
| 2016/0053304 A1 | 2/2016 | Wurzel et al. |
| 2016/0076093 A1 | 3/2016 | Shendure et al. |
| 2016/0102322 A1 | 4/2016 | Ravinder et al. |
| 2016/0130608 A1 | 5/2016 | Doudna et al. |
| 2016/0168592 A1 | 6/2016 | Church et al. |
| 2016/0264981 A1 | 9/2016 | Yang et al. |
| 2016/0281053 A1 | 9/2016 | Sorek et al. |
| 2016/0289673 A1 | 10/2016 | Huang et al. |
| 2016/0298134 A1 | 10/2016 | Chen et al. |
| 2016/0354487 A1 | 12/2016 | Zhang et al. |
| 2017/0002339 A1 | 1/2017 | Barrngou et al. |
| 2017/0022499 A1 | 1/2017 | Lu et al. |
| 2017/0044525 A1 | 2/2017 | Kaper et al. |
| 2017/0051310 A1 | 2/2017 | Doudna et al. |
| 2017/0073705 A1 | 3/2017 | Chen et al. |
| 2017/0191123 A1 | 7/2017 | Kim et al. |
| 2017/0211078 A1 | 7/2017 | Kamineni et al. |
| 2017/0240922 A1 | 8/2017 | Gill et al. |
| 2017/0369870 A1 | 12/2017 | Gill et al. |
| 2018/0028567 A1 | 2/2018 | Li et al. |
| 2018/0052176 A1 | 2/2018 | Holt et al. |
| 2018/0073013 A1 | 3/2018 | Lorenz et al. |
| 2018/0112235 A1 | 4/2018 | Li et al. |
| 2018/0187149 A1 | 7/2018 | Ma et al. |
| 2018/0200342 A1 | 7/2018 | Bikard et al. |
| 2018/0230460 A1 | 8/2018 | Gill et al. |
| 2018/0230461 A1 | 8/2018 | Gill et al. |
| 2018/0284125 A1 | 10/2018 | Gordon et al. |
| 2019/0017072 A1 | 1/2019 | Ditommaso et al. |
| 2019/0085324 A1 | 3/2019 | Regev et al. |
| 2019/0136230 A1 | 5/2019 | Sather et al. |
| 2019/0169605 A1 | 6/2019 | Masquelier et al. |
| 2019/0194650 A1 | 6/2019 | Gill et al. |
| 2019/0225928 A1 | 7/2019 | Masquelier et al. |
| 2019/0270987 A1 | 9/2019 | Masquelier et al. |
| 2020/0071660 A1 | 3/2020 | Spindler et al. |
| 2020/0095533 A1 | 3/2020 | Garst et al. |
| 2020/0216794 A1 | 7/2020 | Belgrader et al. |
| 2020/0263197 A1 | 8/2020 | Cheng et al. |
| 2020/0270632 A1 | 8/2020 | Roy et al. |
| 2021/0054362 A1* | 2/2021 | Park .................. C12N 9/22 |

FOREIGN PATENT DOCUMENTS

| | | | |
|---|---|---|---|
| WO | WO2002/010183 | 2/2002 | |
| WO | WO 2003/087341 | 10/2003 | |
| WO | WO 2010/079430 | 7/2010 | |
| WO | WO 2011/072246 | 6/2011 | |
| WO | WO 2011/143124 | 11/2011 | |
| WO | WO 2013/142578 | 9/2013 | |
| WO | WO 2013/176772 | 11/2013 | |
| WO | WO 2014/018423 | 1/2014 | |
| WO | WO2014/143381 | 9/2014 | |
| WO | WO 2014/144495 | 9/2014 | |
| WO | WO2016/110453 | 7/2016 | |
| WO | WO 2016/110453 | 7/2016 | |
| WO | WO 2017/053902 | 3/2017 | |
| WO | WO2017/075265 | 5/2017 | |
| WO | WO 2017/078631 | 5/2017 | |
| WO | WO 2017/083722 | 5/2017 | |
| WO | WO 2017/106414 | 6/2017 | |
| WO | WO2017/106414 | 6/2017 | |
| WO | WO 2017/161371 | 9/2017 | |
| WO | WO 2017/174329 | 10/2017 | |
| WO | WO 2017/186718 | 11/2017 | |
| WO | WO2017/212400 | 12/2017 | |
| WO | WO 2017/216392 | 12/2017 | |
| WO | WO2017/216392 | 12/2017 | |
| WO | WO 2017/223330 | 12/2017 | |
| WO | WO2017/223330 | 12/2017 | |
| WO | WO 2018/031950 | 2/2018 | |
| WO | WO 2018/071672 | 4/2018 | |
| WO | WO 2018/083339 | 5/2018 | |
| WO | WO2018/152325 | 8/2018 | |
| WO | WO2018/172556 | 9/2018 | |
| WO | WO 2018/191715 | 10/2018 | |
| WO | WO2019/006436 | 1/2019 | |
| WO | WO2019/055878 | 3/2019 | |
| WO | WO2019/200004 | 10/2019 | |
| WO | WO2019/209926 | 10/2019 | |
| WO | WO2020/005383 | 1/2020 | |
| WO | WO2020/021045 | 1/2020 | |
| WO | WO2020/074906 | 4/2020 | |
| WO | WO 2020/237066 A2 * | 11/2020 | ............. C12N 15/74 |

OTHER PUBLICATIONS

Garst, et al., "Genome-wide mapping of mutations at single-nucleotide resolution for protein, metabolic and genome engineering", Nature Biotechnology, 35(1):48-59 (2017).

Hsu, et al., "DNA targeting specificity of RNA-guided Cas9 nucleases", Nature Biotechnology, 31(9):827-32 (2013).

Jiang, et al., "RNA-guided editing of bacterial genomes using CRISPR-Cas systems", Nature Biotechnology, 31(3):233-41 (2013).

Jinek, et al., "A Programmable Dual-RNA-Guided DNA Endonuclease in Adaptive Bacterial Immunity", Science, 337:816-20 (2012).

Verwaal, et al., "CRISPR/Cpf1 enables fast and simple genome editing of *Saccharamyces cerevisiae*", Yeast, 35:201-11 (2018).

Lian, et al., "Combinatorial metabolic engineering using an orthogonal tri-functional CRISPR system", Nature Communications, DOI:1038/s41467-017-01695-x/www.nature.com/naturecommunications, pp. 1-9 (2017).

Roy, et cl., "Multiplexed precision genome editing with trackable genomic barcodes in yeast", Nature Biotechnolgy, doi:10.1038/nbt.4137, pp. 1-16 (2018).

Dong, "Establishment of a highly efficient virus-inducible CRISPR/Cas9 system in insect cells," Antiviral Res., 130:50-7(2016).

Epinat et al., "A novel engineered meganuclease induces homologous recombination in eukaryotic cells, e.g., yeast and mammalian cells", Nucleic Acids Research, 31(11): 2952-2962.

Farasat et al., "A Biophysical Model of CRISPR/Cas9 Activity for Rational Design of Genome Editing and Gene Regulation," PLoS Comput Biol., 29:12(1):e1004724 (2016).

Liu et al., "A chemical-inducible CRISPR-Cas9 system for rapid control of genome editing", Nature Chemical Biology, 12:980-987(2016).

Eklund, et al., "Altered target site specificity variants of the I-Ppol His-Cys bis homing endonuclease" Nucleic Acids Research, 35(17):5839-50 (2007).

Boles, et al., "Digital-to-biological converter for on-demand production of biologics", Nature Biotechnology, doi:10.1038/nbt.3859 (May 29, 2017).

Pines, et al., "Codon Compression Algorithms for Saturation Mutagenesis", ACS Synthetic Biology, 4:604-14 (2015).

Bessa et al., "Improved gap repair cloning in yeast: treatment of the gapped vector with Taq DNA polymerase avoids vector self-ligation," Yeast, 29(10):419-23 (2012).

Boch, "TALEs of genome targeting," Nature Biotechnology vol. 29, pp. 135-136 (2011).

Campbell et al., "Targeting protein function: the expanding toolkit for conditional disruption," Biochem J., 473(17):2573-2589 (2016).

Casini et al., "Bricks and blueprints: methods and standards for DNA assembly," Nat Rev Mol Cell Biol., (9):568-76 (2015).

Chica et al., "Semi-rational approaches to engineering enzyme activity: combining the benefits of directed evolution and rational design," Current Opinion in Biotechnology, 16(4): 378-384 (2005).

Durai et al., "Zinc finger nucleases: custom-designed molecular scissors for genome engineering of plant and mammalian cells", Nucleic Acids Res., 33(18):5978-90 (2005).

Kadonaga et al., "Regulation of RNA polymerase II transcription by sequence-specific DNA binding factors", Cell, 116(2):247-57 (2004).

Lee et al., "Targeted chromosomal deletions in human cells using zinc finger nucleases", Genome Res., 20(1): 81-9 (2009).

(56) References Cited

OTHER PUBLICATIONS

Miller et al., "A Tale nuclease architecture for efficient genome editing", Nature Biotechnology, 29 (2): 143-8 (2011).
Mittelman et al., "Zinc-finger directed double-strand breaks within CAG repeat tracts promote repeat instability in human cells", PNAS USA, 106 (24): 9607-12 (2009).
Shivange, "Advances in generating functional diversity for directed protein evolution", Current Opinion in Chemical Biology, 13 (1): 19-25 (2009).
Udo, "An Alternative Method to Facilitate cDNA Cloning for Expression Studies in Mammalian Cells by Introducing Positive Blue White Selection in Vaccinia Topoisomerase I-Mediated Recombination," PLoS One, 10(9):e0139349 (2015).
Urnov et al., "Genome editing with engineered zinc finger nucleases", Nature Reviews Genetics, 11:636-646 (2010).
International Search Report and Written Opinion for International Application No. PCT/US2018/053608, dated Dec. 13, 2018, p. 1-9.
International Search Report and Written Opinion for International Application No. PCT/US2018/053670, dated Jan. 3, 2019, p. 1-13.
International Search Report and Written Opinion for International Application No. PCT/US2018/053671, dated Sep. 26, 2018, p. 1-12.
International Search Report and Written Opinion for International Application No. PCT/US2018/040519, dated Sep. 26, 2018, p. 1-8.
International Search Report and Written Opinion for International Application No. PCT/US2019/026836, dated Jul. 2, 2019, p. 1-10.
International Search Report and Written Opinion for International Application No. PCT/US2019/023342, dated Jun. 6, 2019, p. 1-34.
International Search Report and Written Opinion for International Application No. PCT/US2019/030085, dated Jul. 23, 2019, p. 1-14.
International Search Report and Written Opinion for International Application No. PCT/US20/24341, dated Jun. 19, 2020, p. 1-9.
NonFinal Office Action for U.S. Appl. No. 16/399,988, dated Jul. 31, 2019, p. 1-20.
First Office Action Interview Pilot Program Pre-Interview Communication for U.S. Appl. No. 16/024,831, dated Feb. 12, 2019, p. 1-37.
NonFinal Office Action for U.S. Appl. No. 16/024,816 dated Sep. 4, 2018, p. 1-10.
Final Office Action for U.S. Appl. No. 16/024,816 dated Nov. 26, 2018, p. 1-12.
First Office Action Interview Pilot Program Pre-Interview Communication Preinterview for U.S. Appl. No. 16/454,865 dated Aug. 16, 2019, p. 1-36.
Yoshioka, et al., "Development of a mono-promoter-driven CRISPR/Cas9 system in mammalian cells", Scientific Reports, Jul. 3, 2015, p. 1-8.
Remaut, et al., "Plasmid vectors for high-efficiency expression controlled by the PL promoter of coliphage lambda," Laboratory of Molecular Biology, Apr. 15, 1981, p. 81-93.
International Search Report and Written Opinion for International Application No. PCT/US2019/028821, dated Aug. 2, 2019, p. 1-14.
International Search Report and Written Opinion for International Application No. PCT/US2019/028883, dated Aug. 16, 2019, p. 1-12.
International Search Report and Written Opinion for International Application No. PCT/US2019/46526, dated Dec. 18, 2019, p. 1-17.
International Search Report and Written Opinion for International Application No. PCT/US2018/34779, dated Nov. 26, 2018, p. 1-39.
International Search Report and Written Opinion for International Application No. PCT/US19/57250, dated Feb. 25, 2020, p. 1-16.
International Search Report and Written Opinion for International Application No. PCT/US19/47135, dated Jun. 11, 2020, p. 1-15.
International Search Report and Written Opinion for International Application No. PCT/US20/19379, dated Jul. 22, 2020, p. 1-10.
International Search Report and Written Opinion for International Application No. PCT/US20/36064, dated Sep. 18, 2020, p. 1-16.
International Search Report and Written Opinion for International Application No. PCT/US20/40389, dated Oct. 13, 2020, p. 1-12.
Arnak, et al., "Yeast Artificial Chromosomes", John Wiley & Sons, Ltd., doi:10.1002/9780470015902.a0000379.pub3, pp. 1-10 (2012).

Woo, et al., "Dual roles of yeast Rad51 N-terminal domain in repairing DNA double-strand breaks", Nucleic Acids Research, doi:10.1093/nar/gkaa.587, vol. 48, No. 15, pp. 8474-8489 (2020).
International Search Report and Written Opinion for International Application No. PCT/US2021/012868, dated Mar. 26, 2021, p. 1-15.
Anzalone et al., "Search-and-replace genome editing without doubles-strand breaks or donor DNA," Nature, Oct. 21, 2019, vol. 576, No. 7785, pp. 149-157.
Alvarez, et al., "In vivo diversification of target genomic sites using processive T7 RNA polymerase-base deaminase fusions blocked by RNA-guided dCas9", Dept.of Microbial Biotechnology and Systems Biology Program, Madrid, Spain, Jan. 1, 2019, p. 1-33.
International Search Report and Written Opinion for International Application No. PCT/US20/65168, dated Mar. 17, 2021, p. 1-15.
International Search Report and Written Opinion for International Application No. PCT/US2020/038345, dated Nov. 23, 2020, p. 1-13.
International Search Report and Written Opinion for International Application No. PCT/US21/12867, dated May 12, 2021, p. 1-17.
International Search Report and Written Opinion for International Application No. PCT/US2020/064727, dated Apr. 28, 2021, p. 1-13.
International Search Report and Written Opinion for International Application No. PCT/US21/29008, dated Aug. 24, 2021, p. 1-19.
International Search Report and Written Opinion for International Application No. PCT/US21/29011, dated Aug. 24, 2021, p. 1-20.
Bauer, et al., "Cell-microcarrier Adhesion to Gas-Liquid Interfaces and Foam", Biotechnol. Prog. 2000, 16, 125-132, Oct. 19, 1999.
Datlinger, et al., "Pooled CRISPR screening with single-cell transcriptome readout", Nature Methods, Jan. 10, 2017; p. 1-10, doi:10.1038/nmeth.4177.
Dixit, et al., "Perturb-Seq: Dissecting Molecular Circuits with Scalable Single-Cell RNA Profiling of Pooled Genetic Screens", Cell 167, p. 1853-1866, Dec. 15, 2016.
GE Healthcare Life Sciences, "Microcarrier Cell Culture Principles and Methods", 18-1140-62 AC, p. 1-23, Nov. 2013.
Jacobi, et al., "Simplified CRISPR tools for efficient genome editing and streamlined protocols for their delivery into mammalian cells and mouse zygotes", Methods 121-122, p. 16-28, Mar. 23, 2017.
Jaitin, et al., "Dissecting Immune Circuits by Linking CRISPR-Pooled Screens with Single-Cell RNA-Seq", Cell 167, p. 1883-1896, Dec. 15, 2016.
Kim, et al., "Formation of Thermoresponsive Poly(N-isopropylacrylamide)/Dextran Particles by Atom Transfer Radical Polymerization", Macromol. Rapid Commun., 24, p. 517-521, 2003.
Kimple, et al., "Overview of Affinity Tags for Protein Purification", Curr Protoc Protein Sci.; 73: Unit-9-9. Doi:10.1002/0471140864.ps0909s73, p. 1-26, Aug. 6, 2015.
Nienow, et al., "A potentially scalable method for the harvesting of hMSCs from microcarriers", Biochemical Engineering Journal 85, p. 79-88, Feb. 4, 2014.
Replogle, et al., "Direct capture of CRISPR quides enables scalable, multiplexed, and multi-omic Perturb-Seq", bioRxiv; doi:http://dx.doi.org/10.1101/503367, p. 1-26, Dec. 21, 2018.
Sivalingam, et al., "Superior Red Blood Cell Generation from Human Pluripotent Stem Cells Through a Novel Microcarrier-Based Embryoid Body Platform", Tissue Engineering: Part C, vol. 22, No. 8, p. 765-780, Jun. 9, 2016.
International Search Report and Written Opinion for International Application No. PCT/US21/35807, dated Nov. 24, 2021, p. 1-21.
International Search Report and Written Opinion for International Application No. PCT/US21/50338, dated Dec. 10, 2021, p. 1-17.
International Search Report and Written Opinion for International Application No. PCT/US21/43097, dated Nov. 19, 2021, p. 1-12.
International Search Report and Written Opinion for International Application No. PCT/US21/39872, dated Oct. 27, 2021, p. 1-14.
International Search Report and Written Opinion for International Application No. PCT/US21/48566, dated Dec. 10, 2021, p. 1-10.
Filsinger, et al., "Characterizing the portability of RecT-mediated oligonucleotide recombination", bioRxiv, Apr. 15, 2020, doi:org/10.1101/2020.04.14.041095, p. 1-25.

(56) References Cited

OTHER PUBLICATIONS

Nelson, et al., "Engineered pegRNAs improve prime editing efficiency", Nature Biotechnology, Jul. 25, 2021, doi.org/10.1038/s41587-021-01039-7, p. 1-14.
Yu, et al., "Improved delivery of Cas9 protein/gRNA complexes using lipofectamine CRISPRMAX", Biotechnol Ltt, Feb. 18, 2016, doi 10.1007/s10529-016-2064-9, p. 919-929.
Bengali, et al., "Gene Delivery Through Cell Culture Substrate Adsorbed DNA Complexes", Biotechnol Bioeng., May 5, 2005, doi:10.1002/bit.20393, p. 1-23.
Segura, et al., "Substrate-mediated DNA delivery: role of the cationic polymer structure and extent of modification", Journal of Controlled Release, Aug. 9, 2003, doi:10.1016/j.jconrel.2003.08.003, p. 69-84.
Takahashi, et al., "Integration of CpG-free DNA induces de novo methylation of CpG islands in pluripotent stem cells," Science, May 5, 2017, vol. 356, No. 6337, pp. 1-7.
Chen, et al., "Human Pluripotent Stem Cell Culture: Considerations for Maintenance, Expansion, and Therapeutics", Cell Stem Cell, Jan. 2, 2014, doi.org/10.1016/j.stem.2013.12.005, p. 13-26.
Fayazpour, F., "Exploring New Applications For Photophysically Encoded Mircrocarriers", Ghent University Faculty of Pharmaceutical Sciences, Thesis Submission, Sep. 2008, 169 pages.
Chueng, et al., "Unlinking the methylome pattern from nucleotide sequence, revealed by large-scale in vivo genome engineering and methylome editing in medaka fish," PLoS Genetics, Dec. 21, 2017, vol. 13, No. 12, pp. 1-25.
Elvin, et al., "Modified bacteriophage lambda promoter vectors for overproduction of proteins in *Escherichia coli*", Gene, 87, Sep. 15, 1989, p. 123-126.
Segall-Shapiro, et al., "Engineered promoters enable constant gene expression at any copy number in bacteria", Nature Biotechnology, vol. 36, No. 4, Mar. 19, 2018, p. 352-363.
Xing, et al., "A CRISPR/Cas9 toolkit for multiplex genome editing in plants", BMC Plant Biology, 2014, p. 1-12.
Sun, et al., "A Single Multiplex crRNA Array for FnCpf1-Mediated Human Genome Editing," Molecular Therapy, Aug. 1, 2018, vol. 26, No. 8, pp. 2070-2076.
Kurata, et al., "Highly multiplexed genome engineering using CRISPR/Cas9 gRNA arrays," PLoS One, Sep. 17, 2018, vol. 13, No. 9, pp. 1-17.
Hubmann, et al., "Natural and Modified Promoters for Tailored Metabolic Engineering of the Yeast *Saccharomyces cerevisiae*", Methods in Molecular Biology, vol. 1152, doi10.1007/978-1-4939-0563-8_2, p. 17-42.
Unciti-Broceta, et al., "Combining Nebulization-Mediated Transfection and Polymer Microarrays for the Rapid Determination of Optimal Transfection Substrates", Journal of Combinatorial Chemistry, vol. 10, No. 2, Feb. 5, 2008, p. 179-184.
Fayazpour, et al., "Evaluation of Digitally Encoded Layer-by-layer Coated Microparticles as Cell Carriers", Advanced Functional Materials, Sep. 1, 2008, p. 2716-2723.
UniProtKB/TrEMBL, "A0A1G4WF58_9FIRM", Nov. 22, 2017, rerieved from Internet: https://www.uniprot.org/uniprot/AOA_1G4WF58.txt, pp. 1-3.
Natsume, et al., "Conditional Degrons for Controlling Protein Expression at the Protein Level", Annual Review of Genetics, vol. 51, 2017, doi.org/10.1146/annurev-genet-120116-024656, p. 83-104.
Chen, et al., "Enhancing the copy number of episomal plasmids in *Saccharomyces cerevisiae* for improved protein production", FEMS Yeast Research, Apr. 25, 2012, doi:10.1111/j.1567-1364.2012.00809.x; p. 598-607.
Price, et al., "Expanding and understanding the CRISPR toolbox for Bacillus subtilis with MAD7 and dMAD7", Biotechnology and Bioengineering, Feb. 19, 2020, doi:10.1002/bit.27312 p. 1805-1816.
International Search Report and Written Opinion for International Application No. PCT/US21/43534, dated Nov. 10, 2021, p. 1-16.
International Search Report and Written Opinion for International Application No. PCT/US20/26095, dated Jul. 17, 2020, p. 1-10.
Fu, Jun, et al.—"Full-length RecE enhances linear-linear homologous recombination and facilitates direct cloning for bioprospecting," Nature Biotechnology, vol. 30, No. 5, May 2012, pp. 440-448.
Wu, Yan, et al.—"RecET recombination system driving chromosomal target gene replaceement in Zymomonas mobilis," Electronic Journal of Biotechnology, vol. 30, 2017, pp. 118-124.

* cited by examiner

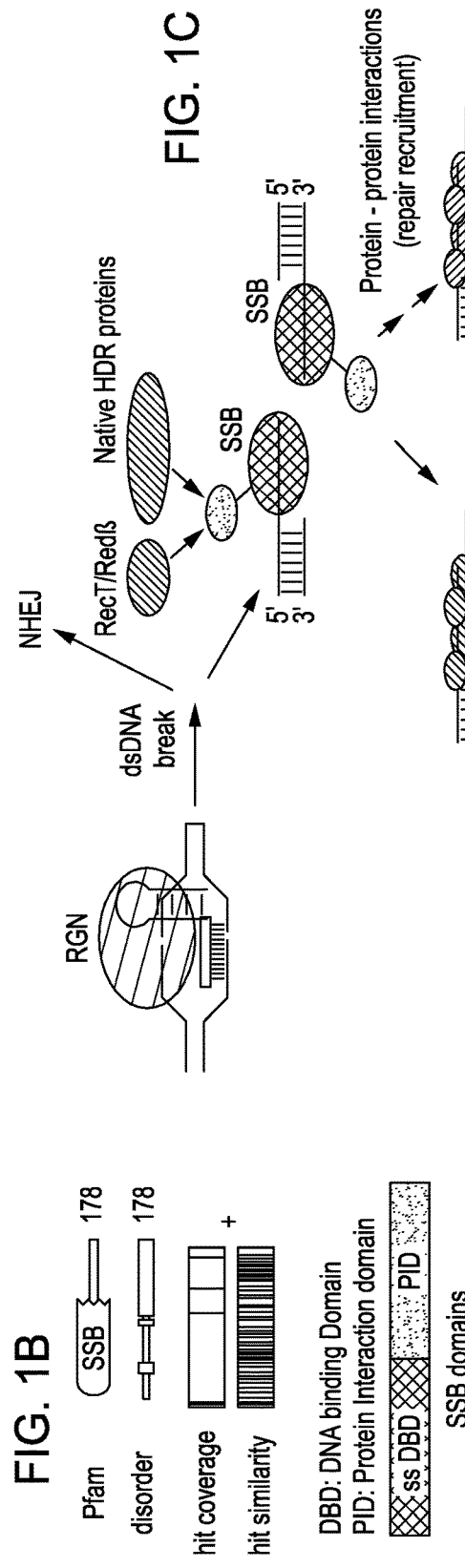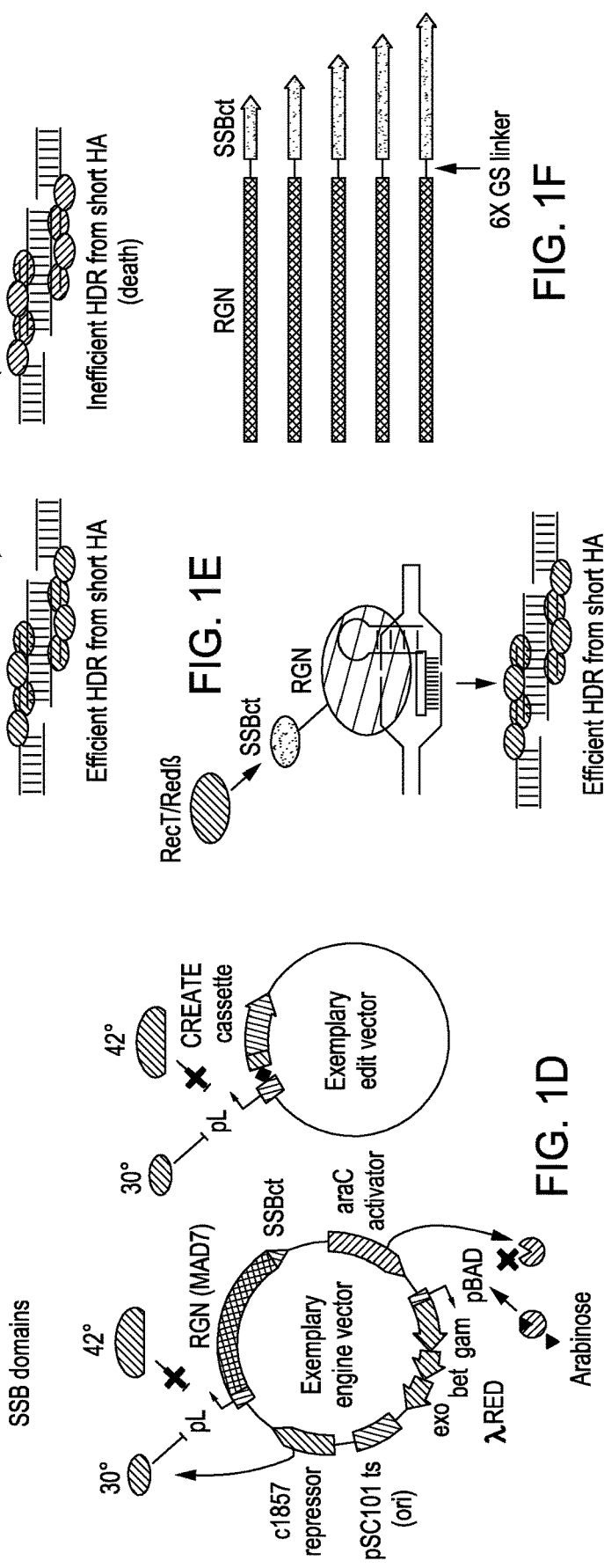

AFFINITY TAG FOR RECOMBINATION PROTEIN RECRUITMENT

RELATED CASES

This application claims priority to U.S. Ser. No. 63/111,495 filed 9 Nov. 2020, entitled "Affinity Tag for Recombination Protein Recruitment", which is incorporated herein in its entirety.

FIELD OF THE INVENTION

The present disclosure relates to methods and compositions to increase the percentage of edited cells in a cell population when employing nucleic-acid guided editing, as well as automated multi-module instruments for performing these methods and using these compositions.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

The ability to make precise, targeted changes to the genome of living cells has been a long-standing goal in biomedical research and development. Recently, various nucleases have been identified that allow for manipulation of gene sequences, and hence gene function. The nucleases include nucleic acid-guided nucleases (or RNA-guided nucleases or "RGNs"), which enable researchers to generate permanent edits in live cells. Of course, it is desirable to attain the highest editing rates possible in a cell population; however, in many instances the percentage of edited cells resulting from nucleic acid-guided nuclease editing can be in the single digits due to toxicity of the double-strand breaks made by these nucleases during the editing process.

There is thus a need in the art of nucleic acid-guided nuclease editing for improved methods, compositions, modules and instruments for increasing the efficiency of editing. The present disclosure addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present disclosure relates to methods, compositions, modules and automated multi-module cell processing instruments that increase the efficiency of nucleic acid-guided editing in a cell population using a nucleic acid nuclease (i.e., an RNA-guided nuclease or "RGN")/single-strand binding protein ("SSB") fusion system. The system leverages a single-strand binding protein ("SSB") and single-strand DNA annealing protein ("SSAP") interactions to drive enhanced recruitment. The system (i.e., "RGN-SSB+SSAP system") addresses the inefficiency of homology-directed recombination ("HDR") by ensuring rapid association kinetics of the HDR proteins to the site of the double-strand break thereby decreasing the incidence of pathways that lead to cell death or error-prone repair.

Thus, there is provided in a first embodiment a system for homologous recombination-based editing of live cells comprising: a fusion protein comprising two domains; an N-terminal RNA-guided endonuclease domain and a C-terminal domain consisting of a full or C-terminal portion of a SSB protein; a single-strand DNA annealing protein (SSAP) that is co-expressed with the fusion protein and exhibits high affinity binding for the SSB fusion domain; auxiliary exonuclease proteins that have co-evolved with the SSAP protein; and an editing cassette comprising a gRNA transcription sequence and a repair template transcription sequence present in an editing vector backbone.

In some aspects, the SSB protein is EcSSB and the SSAP is Redβ; in some aspects, the SSB protein is EcSSB and the SSAP is PapRecT; in some aspects, the SSB protein is PaSSB and the SSAP is Redβ; in some aspects, the SSB protein is PaSSB and the SSAP is PapRecT; in some aspects, the SSB protein is MsSSB and the SSAP is MspRecT; in some aspects, the SSB protein is MsSSB and the SSAP is PapRecT; in some aspects, the SSB protein is LrSSB and the SSAP is LrRecT; and in some aspects, the SSB protein is RPA1 and the SSAP is RAD51.

In addition, in a second embodiment there is provided a system for homologous recombination-based editing of live cells comprising: an RNA-guided endonuclease domain; an over-expressed SSB protein; a single strand DNA annealing protein (SSAP) that is co-expressed with the RGN and SSB proteins and exhibits high affinity binding for the SSB; auxiliary exonuclease proteins that have co-evolved with the SSAP protein; and an editing cassette comprising a gRNA transcription sequence and a repair template transcription sequence present in an editing vector backbone.

In yet a third embodiment there is provided a system for homologous recombination-based editing of live cells comprising: a fusion protein comprising two domains: an N-terminal RNA-guided nuclease (RGN) domain and a C-terminal domain consisting of a full or C-terminal portion of an SSB protein; a single-strand DNA annealing protein (SSAP) that is co-expressed with the fusion protein and exhibits high affinity binding for the SSB fusion domain; and an editing cassette comprising a gRNA transcription sequence and a repair template transcription sequence present in an editing vector backbone.

In some aspects of these embodiments, the endonuclease is selected from the group consisting of MAD7, MAD2, MAD4 and other MADzymes, Cas9 or Cas12, and in some aspects, the live cells are mammalian cells, bacterial cells, or yeast cells.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which:

FIG. 1B shows an exemplary single-strand DNA binding protein characterized by an N-terminal DNA binding domain that is highly conserved and a disordered C-terminal portion that is responsible for mediating protein-protein interactions that recruit repair proteins to the site of DNA damage. FIG. 1C shows a current model of HDR-mediated recombination in *E. coli* following RGN-mediated cutting at a targeted location in the genome to form a double-stranded DNA break. The single-strand DNA binding protein is shown bound to the single-strand DNA ends at the break as it recruits DNA repair proteins for either efficient or inefficient HDR-meditated DNA repair via incorporation of a short donor DNA sequence (HA). FIG. 1D is an exemplary dual-vector system for editing in *E. coli*, with one vector encoding the gRNA/repair template editing cassette and one vector encoding the nucleic acid-guided nuclease (in this case MAD7) fused at its C-terminal end to the C-terminal portion of an *E. coli* single-strand binding protein ("SSBct"). FIG. 1E illustrates the mode of action of a model system comprising the MAD7-SSBct fusion protein where the MAD7-SSBct fusion protein directly recruits repair proteins to gRNA-encoded double-strand DNA breaks, resulting in efficient HDR-meditated DNA repair via HA incorporation. FIG. 1F depicts alternative fusion constructs for the nucleic acid nuclease ("RGN")-single-strand binding protein ("SSB") fusion ("RGN-SSB") protein.

It should be understood that the drawings are not necessarily to scale, and that like reference numbers refer to like features.

DETAILED DESCRIPTION

Figure 1A:
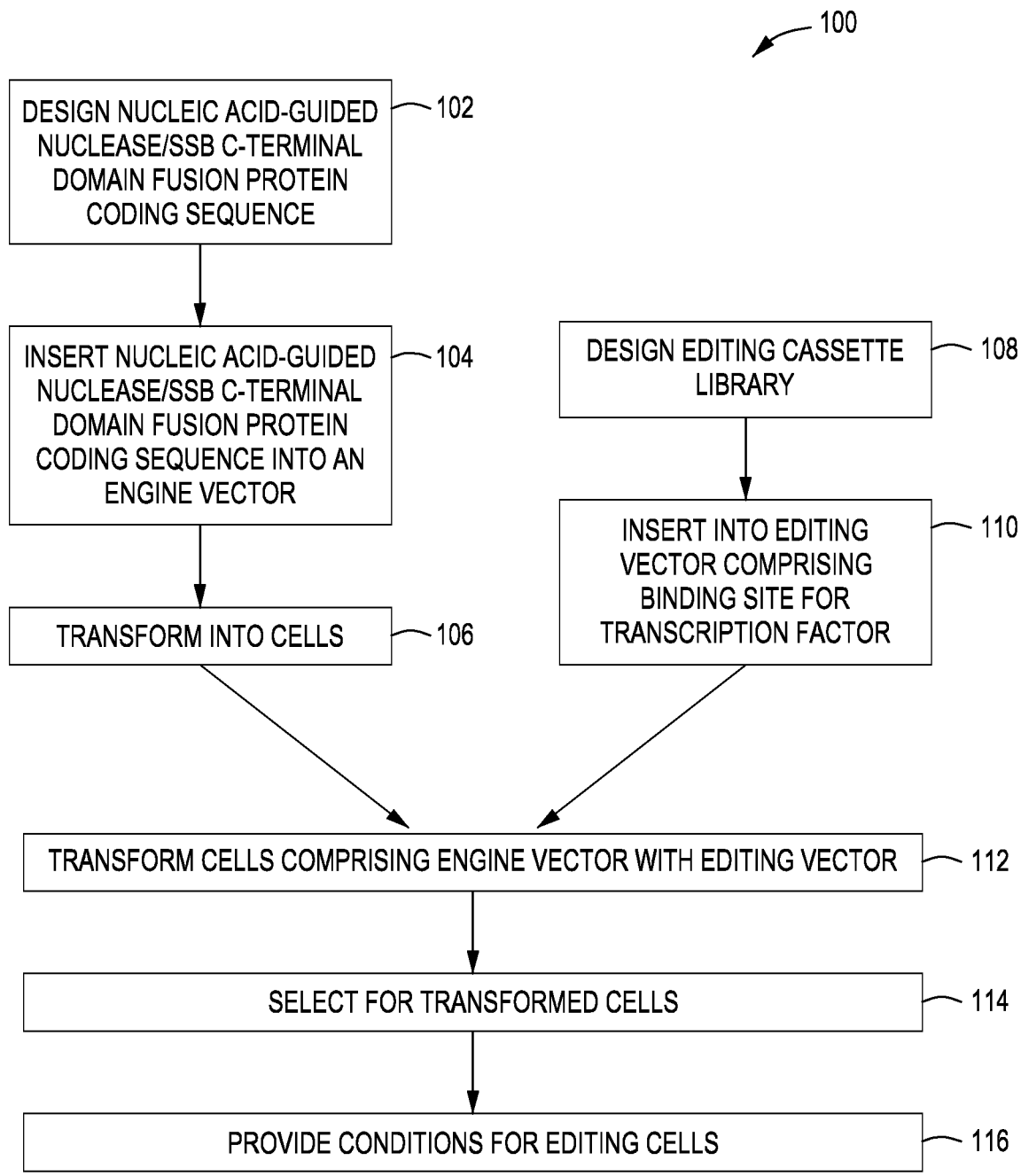
FIG. 1A is a simple process diagram for nucleic acid-guided nuclease editing using a first vector comprising a nucleic acid-guided nuclease fused at its C-terminus to the C-terminal amino acids of a single-strand DNA binding protein.

All of the functionalities described in connection with one embodiment of the methods, devices or instruments described herein are intended to be applicable to the additional embodiments of the methods, devices and instruments described herein except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

The practice of the techniques described herein may employ, unless otherwise indicated, techniques and descriptions of molecular biology (including recombinant techniques), cell biology, biochemistry, and genetic engineering technology. Such techniques and descriptions can be found in standard laboratory manuals such as Green and Sambrook, *Molecular Cloning: A Laboratory Manual*. 4th ed., Cold Spring Harbor Laboratory Press, Cold Spring Harbor, N.Y. (2014); *Current Protocols in Molecular Biology*, Ausubel, et al. eds. (2017); Neumann, et al., *Electroporation and Electrofusion in Cell Biology*, Plenum Press, N Y (1989); and Chang, et al., *Guide to Electroporation and Electrofusion*, Academic Press, CA (1992), all of which are herein incorporated in their entirety by reference for all purposes. Nucleic acid-guided nuclease techniques can be found in, e.g., *Genome Editing and Engineering from TALENs and CRISPRs to Molecular Surgery*, Appasani and Church (2018); and *CRISPR: Methods and Protocols*, Lindgren and Charpentier (2015); both of which are herein incorporated in their entirety by reference for all purposes.

Note that as used herein and in the appended claims, the singular forms "a," "an," and "the" include plural referents unless the context clearly dictates otherwise. Thus, for example, reference to "a cell" refers to one or more cells, and reference to "the system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations, and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TAGCTG-3'.

The term DNA "control sequences" refers collectively to promoter sequences, polyadenylation signals, transcription termination sequences, upstream regulatory domains, origins of replication, internal ribosome entry sites, nuclear localization sequences, enhancers, and the like, which collectively provide for the replication, transcription and translation of a coding sequence in a recipient cell. Not all of these types of control sequences need to be present so long as a selected coding sequence is capable of being replicated, transcribed and—for some components—translated in an appropriate host cell.

The terms "editing cassette", "CREATE cassette", or "CREATE editing cassette", refer to a nucleic acid molecule comprising a coding sequence for transcription of a guide nucleic acid (gRNA) covalently linked to a coding sequence for transcription of a repair template.

As used herein, "enrichment" refers to enriching for edited cells by singulation, inducing editing, and growth of singulated cells into terminal-sized colonies (e.g., saturation or normalization of colony growth).

The terms "guide nucleic acid" or "guide RNA" or "gRNA" refer to a polynucleotide comprising 1) a guide sequence capable of hybridizing to a genomic target locus, and 2) a scaffold sequence capable of interacting or complexing with a nucleic acid-guided nuclease.

"Homology" or "identity" or "similarity" refers to sequence similarity between two peptides or, more often in the context of the present disclosure, between two nucleic acid molecules. The term "homologous region" or "homology arm" refers to a region on the repair template with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Nucleic acid-guided editing components" refer to one, some, or all of a nucleic acid-guided nuclease enzyme (RNA-guided nuclease or RGN), a guide nucleic acid and a repair template.

"Operably linked" refers to an arrangement of elements where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

A "protospacer adjacent motif (PAM) mutation" or "PAM mutation" refers to one or more edits to a target sequence that removes, mutates, or otherwise renders inactive a PAM or spacer region in the target sequence.

A "promoter" or "promoter sequence" is a DNA regulatory region capable of binding RNA polymerase and initiating transcription of a polynucleotide or polypeptide coding sequence such as messenger RNA, ribosomal RNA, small nuclear or nucleolar RNA, guide RNA, or any kind of RNA transcribed by any class of any RNA polymerase I, II or III. Promoters may be constitutive or inducible, and in some embodiments—particularly many embodiments such as those described herein—the transcription of at least one component of the nucleic acid-guided nuclease editing system (and typically at least three components of the nucleic acid-guided nuclease editing system) is under the control of an inducible promoter.

As used herein, the terms "protein" and "polypeptide" are used interchangeably. Proteins may or may not be made up entirely of amino acids.

As used herein the terms "repair template" or "donor DNA" or "donor nucleic acid" or "homology arm" refer to a nucleic acid that is designed to introduce a DNA sequence modification (insertion, deletion, substitution) into a locus by homologous recombination using nucleic acid-guided nucleases (RNA-guided nuclease or RGN). For homology-directed repair, the repair template must have sufficient homology to the regions flanking the "cut site" or the site to be edited in the genomic target sequence. The length of the repair template(s) will depend on, e.g., the type and size of the modification being made. In many instances and preferably, the repair template will have two regions of sequence homology (e.g., two homology arms) complementary to the genomic target locus flanking the locus of the desired edit in the genomic target locus. Typically, an "edit region" or "edit locus" or "DNA sequence modification" region—the nucleic acid modification that one desires to be introduced into a genome target locus in a cell (e.g., the desired edit)—will be located between two regions of homology. The DNA sequence modification may change one or more bases of the target genomic DNA sequence at one specific site or multiple specific sites. A change may include changing 1, 2, 3, 4, 5, 10, 15, 20, 25, 30, 35, 40, 50, 75, 100, 150, 200, 300, 400, or 500 or more base pairs of the target sequence. A deletion or insertion may be a deletion or insertion of 1, 2, 3, 4, 5, 10, 15, 20, 25, 30, 40, 50, 75, 100, 150, 200, 300, 400, or 500 or more base pairs of the target sequence.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, nourseothricin N-acetyl transferase, chloramphenicol, erythromycin, tetracycline, gentamicin, bleomycin, streptomycin, rifampicin, puromycin, hygromycin, blasticidin, and G418 may be employed. In other embodiments, selectable markers include, but are not limited to, sugars such as rhamnose; human nerve growth factor receptor (detected with a MAb, such as described in U.S. Pat. No. 6,365,373); truncated human growth factor receptor (detected with MAb); mutant human dihydrofolate reductase (DHFR; fluorescent MTX substrate available); secreted alkaline phosphatase (SEAP; fluorescent substrate available); human thymidylate synthase (TS; confers resistance to anti-cancer agent fluorodeoxyuridine); human glutathione S-transferase alpha (GSTA1; conjugates glutathione to the stem cell selective alkylator busulfan; chemoprotective selectable marker in CD34+cells); CD24 cell surface antigen in hematopoietic stem cells; human CAD gene to confer resistance to N-phosphonacetyl-L-aspartate (PALA); human multi-drug resistance-1 (MDR-1; P-glycoprotein surface protein selectable by increased drug resistance or enriched by FACS); human CD25 (IL-2α; detectable by Mab-FITC); Methylguanine-DNA methyltransferase (MGMT; selectable by carmustine); and Cytidine deaminase (CD; selectable by Ara-C). "Selective medium" as used herein refers to cell growth medium to which has been added a chemical compound or biological moiety that selects for or against selectable markers.

The term "specifically binds" as used herein includes an interaction between two molecules, e.g., an engineered peptide antigen and a binding target, with a binding affinity represented by a dissociation constant of about $10^{-7}$ M, about $10^{-8}$ M, about $10^{-9}$ M, about $10^{-10}$ M, about $10^{-11}$ M, about $10^{-12}$ M, about $10^{-13}$ M, about $10^{-14}$ M or about $10^{-15}$ M.

The terms "target genomic DNA sequence", "target region", "cellular target sequence", or "genomic target locus" refer to any locus in vitro or in vivo, or in a nucleic acid (e.g., genome or episome) of a cell or population of cells, in which a change of at least one nucleotide is desired using a nucleic acid-guided nuclease editing system. The cellular target sequence can be a genomic locus or extrachromosomal locus. The target genomic DNA sequence comprises the edit region or edit locus.

The terms "transformation", "transfection", and "transduction" are used interchangeably herein to refer to the process of introducing exogenous DNA into cells.

The term "variant" may refer to a polypeptide or polynucleotide that differs from a reference polypeptide or polynucleotide but retains essential properties. A typical variant of a polypeptide differs in amino acid sequence from another reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide may be a conservatively modified variant. A substituted or inserted amino acid residue may or may not be one encoded by the genetic code (e.g., a non-natural amino acid). A variant of a polypeptide may be naturally occurring, such as an allelic variant, or it may be a variant that is not known to occur naturally.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like. As used herein, the phrase "engine vector" comprises a coding sequence for a nuclease to be used in the nucleic acid-guided nuclease systems and methods of the present disclosure. The engine vector may also comprise, in a bacterial system, the λ Red recombineering system or an equivalent thereof. Engine vectors also typically comprise a selectable marker. As used herein the phrase "editing vector" comprises a repair template, including an alteration to the cellular target sequence that prevents nuclease binding at a PAM or spacer in the cellular target sequence after editing has taken place, and a coding sequence for a gRNA. The editing vector may also and preferably does comprise a selectable marker and/or a barcode. In some embodiments, the engine vector and editing vector may be combined; that is, all editing and selection components may be found on a single vector. Further, the engine and editing vectors comprise control sequences operably linked to, e.g., the nuclease coding sequence, recombineering system coding sequences (if present), repair template, guide nucleic acid(s), and selectable marker(s).

Nuclease-Directed Genome Editing Generally

The compositions and methods described herein are employed to perform nuclease-directed genome editing (e.g., RNA-guided nuclease or RGN editing) to introduce desired edits to a population of cells. The most commonly employed method for using RGNs to introduce precision edits is to co-deliver an appropriate gRNA and repair template with the repair template serving as the template for homology-directed repair (HDR) at the intended site. In most organisms, however, innate inefficiencies in HDR lead to high levels of toxicity associated with double-strand DNA breaks. First, cells that receive inactive gRNAs out-compete cells that go through the editing process since cells with inactive gRNAs are not subject to double-strand DNA breaks. Likewise, non-homologous end joining (NHEJ) in mammalian systems outcompetes HDR leading to error-prone repair outcomes which are an impediment to precision editing. Thus, methods and compositions for increasing HDR is a goal in the art of nucleic acid-guided nuclease editing.

Nucleic acid-guided nuclease (RNA-guided nuclease or RGN) editing begins with a nucleic acid-guided nuclease complexing with an appropriate synthetic guide nucleic acid in a cell which can cut the genome of the cell at a desired location. The guide nucleic acid helps the nucleic acid-guided nuclease recognize and cut the DNA at a specific target sequence. By manipulating the nucleotide sequence of the guide nucleic acid, the nucleic acid-guided nuclease may be programmed to target any DNA sequence for cleavage as long as an appropriate protospacer adjacent motif (PAM) is nearby. In certain aspects, the nucleic acid-guided nuclease editing system may use two separate guide nucleic acid molecules that combine to function as a guide nucleic acid, e.g., a CRISPR RNA (crRNA) and trans-activating CRISPR RNA (tracrRNA). In other aspects, the guide nucleic acid may be a single guide nucleic acid that includes both the crRNA and tracrRNA sequences.

In general, a guide nucleic acid (e.g., gRNA) complexes with a compatible RGN and can then hybridize with a target sequence, thereby directing the nuclease to the target sequence. A guide nucleic acid can be DNA or RNA; alternatively, a guide nucleic acid may comprise both DNA and RNA. In some embodiments, a guide nucleic acid may comprise modified or non-naturally occurring nucleotides. In cases where the guide nucleic acid comprises RNA, the gRNA may be encoded by a DNA sequence on a polynucleotide molecule such as a plasmid, linear construct, or the coding sequence may and preferably does reside within an editing cassette and is under the control of an inducible promoter as described below. For additional information regarding "CREATE" editing cassettes, see U.S. Pat. Nos. 9,982,278; 10,266,849; 10,240,167; 10,351,877; 10,364,442; 10,435,715; 10,465,207; 10,669,559; 10,771,284; 10,731,498; and 11,078,498, all of which are incorporated by reference herein.

A guide nucleic acid comprises a guide sequence, where the guide sequence is a polynucleotide sequence having sufficient complementarity with a target sequence to hybridize with the target sequence and direct sequence-specific binding of a complexed RGN to the target sequence. The degree of complementarity between a guide sequence and the corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences. In some embodiments, a guide sequence is about or more than about 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, or 20 nucleotides in length. Preferably the guide sequence is 10-30 or 15-20 nucleotides in length, or 15, 16, 17, 18, 19, or 20 nucleotides in length.

In the present methods and compositions, the guide nucleic acids are provided as a sequence to be expressed from a plasmid or vector and comprises both the guide sequence and the scaffold sequence as a single transcript under the control of an inducible promoter. The guide nucleic acids are engineered to target a desired target sequence by altering the guide sequence so that the guide sequence is complementary to a desired target sequence, thereby allowing hybridization between the guide sequence and the target sequence. In general, to generate an edit in the target sequence, the gRNA/nuclease complex binds to a target sequence as determined by the guide RNA, and the nuclease recognizes a protospacer adjacent motif (PAM) sequence adjacent to the target sequence. The target sequence can be any polynucleotide endogenous or exogenous to a prokaryotic or eukaryotic cell, or in vitro. For example, the target sequence can be a polynucleotide residing in the nucleus of a eukaryotic cell. A target sequence can be a sequence encoding a gene product (e.g., a protein) or a non-coding sequence (e.g., a regulatory polynucleotide, an intron, a PAM, or "junk" DNA).

The gRNA may be and preferably is part of an editing cassette that encodes the repair template that targets a cellular target sequence. Alternatively, the gRNA may not be part of the editing cassette and instead may be encoded on the editing vector backbone or other vector in the system. For example, a sequence coding for an editing gRNA can be assembled or inserted into a vector backbone first, followed by insertion of the repair template in, e.g., an editing cassette. In other cases, the repair template in, e.g., an editing cassette can be inserted or assembled into a vector backbone first, followed by insertion of the sequence coding for the editing gRNA. Preferably, the sequence encoding the editing gRNA and the repair template are located together in a rationally designed editing cassette and are simultaneously inserted or assembled into a vector backbone to create an editing vector. In yet other embodiments, the sequence encoding the gRNA and the sequence encoding the repair template are both included in the editing cassette.

The target sequence is associated with a protospacer adjacent motif (e.g., PAM), which is a short nucleotide sequence recognized by the gRNA/nuclease complex. The precise preferred PAM sequence and length requirements for different nucleic acid-guided nucleases vary; however, PAMs typically are 2-10 base-pair sequences adjacent or in proximity to the target sequence and, depending on the nuclease, can be 5' or 3' to the target sequence. Engineering of the PAM-interacting domain of a nucleic acid-guided nuclease may allow for alteration of PAM specificity, improve target site recognition fidelity, decrease target site recognition fidelity, or increase the versatility of a nucleic acid-guided nuclease.

In certain embodiments, the genome editing of a cellular target sequence both introduces a desired DNA change to a cellular target sequence, e.g., the genomic DNA of a cell, and removes, mutates, or renders inactive a protospacer adjacent motif mutation (e.g., PAM mutation) region in the cellular target sequence. Rendering the PAM at the cellular target sequence inactive precludes additional editing of the cell genome at that cellular target sequence, e.g., upon subsequent exposure to a nucleic acid-guided nuclease complexed with a synthetic guide nucleic acid in later rounds of editing. Thus, cells having the desired cellular target sequence edit and an altered PAM can be selected for by using a nucleic acid-guided nuclease complexed with a synthetic guide nucleic acid complementary to the cellular target sequence. Cells that did not undergo the first editing event will be cut rendering a double-stranded DNA break, and thus will not continue to be viable. The cells containing the desired cellular target sequence edit and PAM alteration will not be cut, as these edited cells no longer contain the necessary PAM site and will continue to grow and propagate.

The range of target sequences that nucleic acid-guided nucleases can recognize is constrained by the need for a specific PAM to be located near the desired target sequence. As a result, it often can be difficult to target edits with the precision that is necessary for genome editing. It has been found that nucleases can recognize some PAMs very well (e.g., canonical PAMs), and other PAMs less well or poorly (e.g., non-canonical PAMs). Because the methods disclosed herein allow for identification of edited cells in a background of unedited cells, the methods allow for identification of edited cells where the PAM is less than optimal; that is, the methods for identifying edited cells herein allow for identification of edited cells even if editing efficiency is very low. Additionally, the present methods expand the scope of target sequences that may be edited since edits are more readily identified, including cells where the genome edits are associated with less functional PAMs.

As for the nuclease component of the RNA-guided nuclease (RGN) editing system, a polynucleotide sequence encoding the RGN can be codon-optimized for expression in particular cell types, such as archaeal, prokaryotic or eukaryotic cells. Eukaryotic cells can be yeast, fungi, algae, plant, animal, or human cells. Eukaryotic cells may be those of or derived from a particular organism, such as a mammal, including but not limited to human, mouse, rat, rabbit, dog, or non-human mammals including non-human primates. The choice of RGN to be employed depends on many factors, such as what type of edit is to be made in the target sequence and whether an appropriate PAM is located close to the desired target sequence. Nucleases of use in the methods described herein include but are not limited to Cas 9, Cas 12/Cpf1, MAD2, or MAD7 or other MADzymes (for more information about MADzymes see U.S. Pat. Nos. 10,011,849; 10,435,714; 10,626,416; 10,604,746; 10,655,114; 10,640,754; 10,876,102; 10,704,033; 10,745,678, 10,724,021; 10,767,169; 10,870,761; 10,626,416; 9,982,279 and 10,337,028). In the present disclosure, the RGN is fused to a single-strand binding protein (discussed in detail infra).

As with the guide nucleic acid, the nuclease is often encoded by a DNA sequence on a vector (e.g., the engine vector) and be under the control of an inducible promoter. In some embodiments, the inducible promoter may be separate from but the same as the inducible promoter controlling transcription of the guide nucleic acid; that is, a separate inducible promoter drives the transcription of the nuclease and guide nucleic acid sequences but the two inducible promoters may be the same type of inducible promoter (e.g., both are pL promoters). Alternatively, the inducible promoter controlling expression of the nuclease may be different from the inducible promoter controlling transcription of the guide nucleic acid; that is, e.g., the nuclease may be under the control of the pBAD inducible promoter, and the guide nucleic acid may be under the control of the pL inducible promoter.

Another component of the RGN system is the repair template comprising homology to the cellular target sequence. In some embodiments, the repair template is on the same polynucleotide (e.g., editing vector or editing cassette) as the gRNA and preferably is (but not necessarily is) under the control of the same promoter as the gRNA (e.g., a single promoter driving the transcription of both the gRNA and the repair template). The repair template is designed to serve as a template for homologous recombination with a cellular target sequence nicked or cleaved by the nucleic acid-guided nuclease as a part of the gRNA/nuclease complex. A repair template polynucleotide may be of any suitable length, such as about or more than about 20, 25, 50, 75, 100, 150, 200, 500, or 1000 nucleotides in length. In certain preferred aspects, the repair template can be provided as an oligonucleotide of between 20-300 nucleotides, more preferably between 50-250 nucleotides. The repair template comprises a region that is complementary to a portion of the cellular target sequence (e.g., a homology arm). When optimally aligned, the repair template overlaps with (i.e., is complementary to) the cellular target sequence by, e.g., about 20, 25, 30, 35, 40, 50, 60, 70, 80, 90 or more nucleotides. The repair template comprises two homology arms (regions complementary to the cellular target sequence) flanking the mutation or difference between the repair template and the cellular target sequence. The repair template comprises at least one mutation or alteration compared to the cellular target sequence, such as an insertion, deletion, modification, or any combination thereof compared to the cellular target sequence.

Again, the repair template is preferably provided as part of a rationally-designed editing cassette, which is inserted into an editing vector backbone where the editing vector backbone may comprise a promoter driving transcription of the gRNA and the repair template, and also comprise a selectable marker different from the selectable marker contained on the engine vector. Moreover, there may be more than one, e.g., two, three, four, or more gRNA/repair template rationally-designed editing cassettes inserted into an editing vector (alternatively, a single rationally-designed editing cassette may comprise two to several gRNA/repair template pairs), where each gRNA is under the control of separate different promoters, separate like promoters, or where all gRNAs/repair template pairs are under the control of a single promoter. In preferred embodiments the promoter driving transcription of the gRNA and the repair template (or driving more than one gRNA/repair template pair) is an inducible promoter and the promoter driving transcription of the nuclease is an inducible promoter as well. In some embodiments and preferably, the nuclease and gRNA/repair template are under the control of the same inducible promoter.

Inducible editing is advantageous in that singulated cells can be grown for several to many cell doublings before editing is initiated, which increases the likelihood that cells with edits will survive, as the double-strand cuts caused by active editing are largely toxic to the cells. This toxicity results both in cell death in the edited colonies, as well as possibly a lag in growth for the edited cells that do survive but must repair and recover following editing. However, once the edited cells have a chance to recover, the size of the colonies of the edited cells will eventually catch up to the size of the colonies of unedited cells (see, e.g., U.S. Pat. Nos. 10,633,626; 10,844,344; and 11,046,928).

In addition to the repair template, an editing cassette may comprise and preferably does comprise one or more primer sites. The primer sites can be used to amplify the editing cassette by using oligonucleotide primers; for example, if the primer sites flank one or more of the other components of the editing cassette.

Also, as described above, the repair template may comprise—in addition to the at least one mutation relative to a cellular target sequence—one or more PAM sequence alterations that mutate, delete or render inactive the PAM site in the cellular target sequence. The PAM sequence alteration in the cellular target sequence renders the PAM site "immune" to the nucleic acid-guided nuclease and protects the cellular target sequence from further editing in subsequent rounds of editing if the same nuclease is used.

In addition, the editing cassette may comprise a barcode. A barcode is a unique DNA sequence that corresponds to the repair template sequence such that the barcode can identify the edit made to the corresponding cellular target sequence. The barcode typically comprises four or more nucleotides. In some embodiments, the editing cassettes comprise a collection or library gRNAs and of repair templates representing, e.g., gene-wide or genome-wide libraries of gRNAs and repair templates. The library of editing cassettes is cloned into vector backbones where, e.g., each different repair template is associated with a different barcode.

Additionally, in some embodiments, an expression vector or cassette encoding components of the nucleic acid-guided nuclease system further encodes a nucleic acid-guided nuclease comprising one or more nuclear localization sequences (NLSs), such as about or more than about 1, 2, 3, 4, 5, 6, 7, 8, 9, 10, or more NLSs. In some embodiments, the engineered nuclease comprises NLSs at or near the amino-terminus, NLSs at or near the carboxy-terminus, or a combination.

The engine and editing vectors comprise control sequences operably linked to the component sequences to be transcribed. As stated above, the promoters driving transcription of one or more components of the nucleic acid-guided nuclease editing system preferably are inducible. A number of gene regulation control systems have been developed for the controlled expression of genes in plant, microbe, and animal cells, including mammalian cells, including the pL promoter (induced by heat inactivation of the cI857 repressor), the pPhIF promoter (induced by the addition of 2,4 diacetylphloroglucinol (DAPG)), the pBAD promoter (induced by the addition of arabinose to the cell growth medium), and the rhamnose inducible promoter (induced by the addition of rhamnose to the cell growth medium). Other systems include the tetracycline-controlled transcriptional activation system (Tet-On/Tet-Off, Clontech, Inc. (Palo Alto, Calif.); Bujard and Gossen, PNAS, 89(12):5547-5551 (1992)), the Lac Switch Inducible system (Wyborski et al., Environ Mol Mutagen, 28(4):447-58 (1996); DuCoeur, et al., Strategies 5(3):70-72 (1992); U.S. Pat. No. 4,833,080), the ecdysone-inducible gene expression system (No, et al., PNAS, 93(8):3346-3351 (1996)), the cumate gene-switch system (Mullick, et al., BMC Biotechnology, 6:43 (2006)), and the tamoxifen-inducible gene expression (Zhang, et al., Nucleic Acids Research, 24:543-548 (1996)) as well as others. In the present methods used in the modules and instruments described herein, it is preferred that at least one of the nucleic acid-guided nuclease editing components (e.g., the nuclease and/or the gRNA) is under the control of a promoter that is activated by a rise in temperature, as such a promoter allows for the promoter to be activated by an increase in temperature, and de-activated by a decrease in temperature, thereby "turning off" the editing process. Thus, in the scenario of a promoter that is de-activated by a decrease in temperature, editing in the cell can be turned off without having to change media; to remove, e.g., an inducible biochemical in the medium that is used to induce editing.

Increasing Efficiency of Editing of an RGN-SSB Fusion System

The present disclosure is drawn to increasing the efficiency of nucleic acid-guided nuclease (RNA-guided nuclease or RGN) editing. Genome editing using RGN technology requires precise repair of nuclease-induced double-strand DNA breaks via homologous recombination with an editing plasmid. Double-strand DNA breaks in cells caused by RGNs have three main outcomes: 1) cell death if the break is not repaired; 2) non-homologous end joining (NHEJ), which repairs the break without a homologous repair template; and 3) homology-directed recombination (HDR), which uses auxiliary (here, exogenous) homologous DNA—e.g., a repair template sequence from an editing cassette inserted into the editing plasmid—to repair the break.

To increase HDR in nucleic-guided nuclease editing, a nucleic acid nuclease (i.e., RNA-guided nuclease or "RGN")-single-strand binding protein ("SSB") fusion ("RGN-SSB") system is employed. The RGN-SSB system leverages single-strand binding protein and single-strand DNA annealing protein ("S SAP") interactions to drive enhanced recruitment of repair proteins to the site of the break. The system (i.e., "RGN-SSB+SSAP system") addresses the inefficiency of homology-directed recombination ("HDR") by ensuring rapid association of the HDR proteins at the site of the double-strand DNA break in favor of competing pathways that lead to cell death or error-prone repair. Although specific embodiments describe an RGN-SSB+SSAP system that is operable in *E. coli*, in practice the RGN-SSB+SSAP system may be selected from a variety of host-phage systems with homology to the recT and/or other SSAP families thus allowing for modular editing systems with broad host applicability. See, e.g., Table 1.

TABLE 1

| SSB | Genbank Accession No. | Source | SSAP (RecT) | Genbank Accession No. | Source |
| --- | --- | --- | --- | --- | --- |
| EcSSB | NP_418483 | *E. coli* | Redβ | ALA45773 | Escherichia virus Lambda |
| EcSSB | NP_418483 | *E. coli* | PapRecT | WP_003088368 | Pseudomonas aeruginosa |
| PaSSB | 6JDG_D | Pseudomonas aeruginosa | Redβ | ALA45773 | Escherichia virus Lambda |
| PaSSB | 6JDG_D | Pseudomonas aeruginosa | PapRecT | WP_003088368 | Pseudomonas aeruginosa |

TABLE 1-continued

| SSB | Genbank Accession No. | Source | SSAP (RecT) | Genbank Accession No. | Source |
|---|---|---|---|---|---|
| MsSSB | SUA33216 | *Mycobacterium smegmatis* | MspRecT | NP_817738 | Mycobacterium virus Che9c |
| MsSSB | SUA33216 | *Mycobacterium smegmatis* | PapRecT | WP_003088368 | Pseudomonas aeruginosa |
| LrSSB | WP_003669492 | *Limosilactobacillus reuteri* | LrRecT | WP_003668036 | Limosilactobacillus reuteri |
| RPA1 | KAF1906078 | *Saccharomyces cerevisiae* | RAD51 | CAA45563 | Saccharomyces cerevisiae |

One HDR based technology that has been developed for high efficiency recombination, called Recombineering, was originally developed in *E. coli* using the Red operon derived from λ phage. The Red operon encodes three genes that cooperate to catalyze homologous recombination. The exo gene has 5'-3' exonuclease activity that chews back one strand and recruits a single-stranded DNA annealing protein (SSAP) known as Redβ to the exposed ssDNA overhang thereby promoting the subsequent base pairing and recombination reactions. Finally, the gam protein forms a protein filament that mimics the structure of DNA and binds to recBCD complexes thereby serving as a competitive inhibitor for dsDNA binding.

Although Recombineering is primarily based on the ability of this system catalyze ssDNA integration at the lagging strand of DNA replication forks, the λ-Red system and other recT-like SSAP based systems have also been shown to promote highly efficient recombination between dsDNA substrates in vivo. This activity has also been leveraged extensively for generating BACs and for massively parallel CRISPR-based genome editing (see Garst, et al., Nature Biotechnology, 35(1):48-55 (2017)). Despite the utility of SSAP-based HDR, these systems have remained limited due to their narrow tropism and inactivity outside enterobacteriaceae hosts. Recent work however has shed light on this elusive problem by demonstrating that the host single-strand DNA binding protein (SSB), which plays a central role in native DNA repair (see FIG. 1C described infra), is also responsible for recruiting the phage derived SSAP to its DNA substrate. For example, over-expression of the *E. coli* SSB protein in the non-enterobacteriaceae species *L. lactis* was shown to yield high efficiency recombination, suggesting that minimally-reconstituted SSAP and SSB partners can provide sufficient activity to promote high efficiency HDR. Furthermore it has been demonstrated that the nine amino acid residues at the C-terminus of the SSB are sufficient to drive the protein-protein interaction that recruits SSAP to DNA (see Filsinger, et al., bioRxiv, 2020.04.14.041095 (2020)).

The present disclosure presents a more versatile and efficient HDR-based editing platform by leveraging the modular SSB-SSAP interactions to drive enhanced SSAP recruitment in an organism agnostic manner (see FIG. 1E described infra). In one embodiment, a two-vector editing system is used (see FIG. 1D described infra). This system encodes the RGN-SSBct fusion protein along with the SSAP Redβ protein along with the rest of the λ-Red operon and a CREATE cassette expressed of a second vector under the same inducible promoter architecture. The SSB-tagged RGN binds to and recruits the SSAP proteins required for HDR (FIG. 1E) and increases the local concentration of the SSAPs at the target cut site. As a result, this strategy addresses the inefficiency of HDR by ensuring more rapid association kinetics of the HDR proteins in favor of competing pathways that can lead to cell death or error-prone repair. Addressing the toxicity issue directly opens the door to better multiplexing capabilities (i.e. multiple edits per cell) allowing more rapid combinatorial optimization for strain engineering and deconvolution of genotype-phenotype associations in disease etiology. Thus, the present disclosure provides the exemplary *E. coli* system as well as a more generalized strategy of RGN-SSB+SSAP editing systems which are selected from a variety of host-phage systems with homology to the recT and other SSAP families (see Filsinger, et al., bioRxiv, 2020.04.14.041095 (2020)). This general strategy lends itself to construction of modular editing systems with broad host activities.

One solution to establishing recombineering in a new species is to temporarily overexpress an exogenous SSB and an exogenous recT or SSAP. Identifying optimal fusions for the nucleic acid nuclease-single-strand binding protein fusion ("RGN-SSB") is within the skill of one of ordinary skill given the teachings of the present disclosure (see, e.g., FIG. 1F and the description thereof infra).

FIG. 1A is a simple process diagram for a method of RNA-guided nuclease (RGN) editing 100 using an engine vector comprising a coding sequence for an RGN-SSB fusion protein. Single-strand DNA-binding protein (SSB) binds to single-stranded regions of DNA serving a variety of functions. First, SSB protects the single-stranded DNA from being broken down (or "chewed up") by nucleases during DNA repair. Second, SSB removes the secondary structure of the strands so that other enzymes are able to access the strands to act effectively. Single-stranded DNA is utilized primarily during major aspects of DNA metabolism such as replication, recombination and repair. In addition to stabilizing ssDNA, SSB proteins also bind to and control the function of many other proteins that are involved in all three of these cellular processes. During DNA replication, SSB molecules bind to the newly separated individual DNA strands, keeping the strands separated by holding them in place so that each strand can serve as a template for new DNA synthesis.

SSB proteins have been identified in many different organisms, but the most well understood SSB remains the SSB of *E. coli*. *E. coli* SSB is a homotetramer consisting of four identical subunits which are each about 19 kDa in size. There are two different binding modes of the *E. coli* SSB when it complexes with ssDNA, found to be dependent on salt concentration in addition to other unknown factors. Under low salt conditions, the protein is less efficient as only two of the four identical subunits of *E. coli* SSB were found to bind to the ssDNA. Under high salt concentrations, however, all four subunits of the homotetramer bind to the ssDNA, thereby increasing the number of nucleotides in contact with the SSB and thus favoring SSB-ssDNA interactions. Depending on the salt concentration and other factors, estimates of the size of the site of interaction between SSB and ssDNA range anywhere from 30 to 73 nucleotides for each tetramer.

The tetramers of *E. coli* SSB consist of α-helices, β-sheets, and random coils. Each subunit contains an α-helix and several β-sheets. The secondary structure also includes a $NH_2$ terminus, which consists of multiple basic residues, or positively charged amino acids. The DNA-binding domain lies within 115 amino acid residues from this terminus. The COOH terminus includes many negatively charged, or acidic amino acids.

Several specific amino acid residues play essential roles in the binding of ssDNA to SSB. Phe60 is a key residue involved in binding the ssDNA to the protein, as it has been shown to be the site for cross-linking. Tryptophan and lysine residues are important in binding as well, as evidenced by modification treatments of lysine and tryptophan residues resulting in a complete loss of binding activity for the protein. The two tryptophan residues involved in ssDNA binding are Trp40 and Trp54, which were determined by mutagenesis. One more key residue in the binding site, His55, was determined by site-specific mutagenesis, as when His55 is substituted with Leu it decreases the overall binding affinity for ssDNA. All of these residues are found in a hydrophobic region, which is suitable for nucleotide base interactions. Treatments that modified arginine, cysteine, or tyrosine residues had no effect on binding of SSB to DNA, suggesting that these amino acids are not involved in significant interactions of the protein with the ssDNA. Most of the SSB molecule loses flexibility after ssDNA binding. However, three phenylalanine residues in the COOH terminal domain remain flexible, even after DNA binding, and it has been found that the COOH terminus is responsible for protein binding. See Filsinger, et al., bioRxiv, 2020.04.14.041095 (2020). Indeed, Filsinger demonstrated that the nine amino acid residues at the C-terminus of the SSB are sufficient to drive the protein-protein interaction that recruits SSAP to the ssDNA.

The first step 102 in FIG. 1A is to design an RNA-guided nuclease (RGN) and single-strand binding protein ("SSB") fusion ("RGN-SSB") or an RNA-guided nuclease (RGN) and C-terminal single-strand binding protein ("SSBct") fusion ("RGN-SSBct") protein coding sequence. The nucleic acid nuclease used for the fusion protein can be any nucleic acid-guided nuclease including but are not limited to Cas 9, Cas 12/CpfI, MAD2, or MAD7 or other MADzymes (see, e.g., for more information about MADzymes U.S. Pat. Nos. 10,011,849; 10,435,714; 10,626,416; 10,604,746; 10,655,114; 10,640,754; 10,876,102; 10,704,033; 10,745,678, 10,724,021; 10,767,169; 10,870,761; 10,626,416; 9,982,279 and 10,337,028) and the single-strand binding protein can be one of a variety of host-phage systems with homology to the recT and other SSAP families. See Filsinger, et al., bioRxiv, 2020.04.14.041095 (2020). Identifying optimal fusion constructs may be accomplished by creating for each SSB-SSAP candidate pair RGN-SSB or RGN-SSBct fusions that vary both the length of a linker between the RGN and the SSB or SSBct domains, if present, and the length of the SSB or SSBct domain followed by systematic testing of these fusions. (See, e.g., FIG. 1F.) In addition, SSB or SSBct copy number (e.g., SSB or SSBct repeats) may be altered as well. Note that in some embodiments, the C-terminal portion of the SSB may be used (e.g., C-terminal truncations known to recruit the SSAP) ("SSBct"), in other embodiments, the entire SSB coding sequence may be used in the fusion.

Following design of the RGN-SSBct or RGN-SSB fusion coding sequence, the RGN-SSBct fusion coding sequence is inserted (via, e.g., Gibson Assembly) into a vector backbone 104 comprising, e.g., a promoter to drive transcription and expression of the RGN-SSBct fusion coding sequence, as well as one or more origins of replication, a selective marker such as a gene coding for antibiotic resistance and the λRed recombineering system. Following insertion of the RGN-SSBct fusion coding sequence into a vector backbone thereby creating an engine vector, the engine vector is transformed 106 into cells of choice, in this instance, *E. coli* cells.

Transformation is intended to include a variety of art-recognized techniques for introducing an exogenous nucleic acid sequence (e.g., engine and/or editing vectors) into a target cell, and the term "transformation" as used herein includes all transformation and transfection techniques. Such methods include, but are not limited to, electroporation, lipofection, optoporation, injection, microprecipitation, microinjection, liposomes, particle bombardment, sonoporation, laser-induced poration, calcium phosphate or calcium chloride co-precipitation, or DEAE-dextran-mediated transfection. Cells can also be prepared for vector uptake using, e.g., a sucrose, sorbitol or glycerol wash. Additionally, hybrid techniques that exploit the capabilities of mechanical and chemical transfection methods can be used, e.g., magnetofection, a transfection methodology that combines chemical transfection with mechanical methods. In another example, cationic lipids may be deployed in combination with gene guns or electroporators. Suitable materials and methods for transforming or transfecting target cells can be found, e.g., in Green and Sambrook, *Molecular Cloning: A Laboratory Manual,* 4th ed., Cold Spring Harbor Laboratory Press, Cold Spring Harbor, N.Y. (2014).

Simultaneously or next, an editing cassette library is designed 108. Methods and compositions for designing and synthesizing editing cassettes are described in U.S. Pat. Nos. 9,982,278; 10,266,849; 10,240,167; 10,351,877; 10,364,442; 10,435,715; 10,465,207; 10,669,559; 10,771,284; 10,731,498; and 11,078,498, where 11,078,498 describes compound editing cassettes that are used in some embodiments of the compositions and methods described herein. Compound editing cassettes are editing cassettes comprising more than one gRNA and more than one repair template and are particularly useful with the RGN-SSBct+SSAP system, which improves HDR even during simultaneous editing of two to several genomic loci. Once designed 108 and synthesized, the library of editing cassettes is amplified, purified and inserted 110 into an editing vector to produce a library of editing vectors where the editing vectors also comprise a binding site for the dimerized transcription factor linked to the N-terminal and C-terminal portions of the nuclease. The library of editing vectors is then transformed into the cells that have already been transformed with the N-terminal and C-terminal transcription factor constructs 112.

Once transformed, the cells are allowed to recover and selection is performed 114 to select for cells transformed with the engine vector(s) and editing vector, both of which most often comprise a selectable marker. As described above, drug selectable markers such as ampicillin/carbenicillin, kanamycin, chloramphenicol, nourseothricin N-acetyl transferase, erythromycin, tetracycline, gentamicin, bleomycin, streptomycin, puromycin, hygromycin, blasticidin, and G418 or other selectable markers may be employed. At a next step, conditions are provided such that editing takes place 116—which may include induction of editing via inducible promoters driving transcription of the editing machinery—and the cells may be used in research or may be grown to a desired OD to be made electrocompetent again, followed by another round of editing.

FIG. 1B shows an exemplary single-strand DNA binding protein characterized by an N-terminal DNA binding domain that is highly conserved, and a disordered C-terminal portion that is responsible for mediating the protein-protein interactions that recruit repair proteins to the site of DNA damage. FIG. 1C shows a current model of HDR-mediated recombination in E. coli. At left of FIG. 1C is shown an RGN binding to target DNA. The RGN complex causes a double-strand break in the target DNA which can be resolved by non-homologous end joining (NHEJ) or by strand resection where single-strand DNA annealing protein ("S SAP") interactions—here, RecT/Redβ and native HDR proteins—interact with and compete for the protein interaction domain of SSB to effect repair (either efficient or inefficient) a of the double-strand break.

FIG. 1D is an exemplary vector system for editing in E. coli, with one vector encoding the gRNA/repair template editing cassette (e.g., the editing vector) and one vector encoding the RGN (in this case MAD7) (e.g., the engine vector) fused at its C-terminal end to the C-terminal portion of an E. coli single-strand binding protein (SSBct). At left of FIG. 1D is an exemplary engine vector comprising at 11 o'clock and moving from 5' to 3': an RGN-SSBct fusion coding sequence under the control of the inducible pL promoter; an araC activator gene; a λRed recombineering system under the control of an inducible pBAD promoter (where the pBAD promoter is activated upon addition of arabinose) a pSC101 temperature sensitive origin of replication and the c1857 repressor gene. The c1857 gene product actively represses the pL promoter at low temperatures (e.g., 30° C.), but at 42° C. the c1857 gene product loses its tertiary structure and is no longer able to repress the pL promoter. That is, by raising the temperature of the cell culture to 42° C., the c1857 repressor is not able to repress the pL promoter and the RGN-SSBct fusion protein is transcribed and translated. The exemplary engine vector shown in FIG. 1D optionally may comprise additional sequences, such as a gene for a selective marker, restriction sites, and the like.

At right of FIG. 1D is an exemplary editing vector for editing in E. coli. The editing vector shown comprises at 11 o'clock a pL promoter driving transcription of an editing cassette. The c1857 gene product expressed from the engine vector actively represses the pL promoter driving transcription of the editing cassette at low temperatures, but at 42° C. the c1857 gene product loses its tertiary structure and is no longer able to repress the pL promoter. That is, by raising the temperature of the cell culture to 42° C., the c1857 repressor is not able to repress the pL promoter and the editing (e.g., CREATE) cassette is transcribed along with the RGN-SSBct fusion protein from the engine vector. Thus, in this example, transcription of both the RGN-SSBct fusion protein and the editing cassette components (e.g., gRNA and repair template) are under control of a pL promoter; however, in other embodiments, different inducible promoters may be used to drive transcription of the RGN-SSBct fusion protein and the editing cassette or in some embodiments only one of the RGN-SSBct fusion protein and editing cassette are under control of an inducible promoter.

For example, the pL and pBAD promoters are shown in relation to the exemplary engine and editing vectors in FIG. 1D; however, a number of gene regulation control systems have been developed for the controlled expression of genes in plant, microbe and animal cells, including mammalian cells. These systems include the tetracycline-controlled transcriptional activation system (Tet-On/Tet-Off, Takara-Clontech, Inc. (Palo Alto, Calif.); Bujard and Gossen, PNAS, 89(12):5547-5551 (1992)), the Lac Switch Inducible system (Wyborski, et al., Environ Mol Mutagen, 28(4):447-58 (1996); DuCoeur, et al., Strategies 5(3):70-72 (1992); and U.S. Pat. No. 4,833,080), the ecdysone-inducible gene expression system (No, et al., PNAS, 93(8):3346-3351 (1996)), the cumate gene-switch system (Mullick, et al., BMC Biotechnology, 6:43 (2006)), and the tamoxifen-inducible gene expression (Zhang, et al., Nucleic Acids Research, 24:543-548 (1996)) as well as others. However, the pL promoter is a particularly useful inducible promoter in E. coli because the pL promoter is activated by an increase in temperature, to, e.g., 42° C., and deactivated by returning the temperature to, e.g., 30° C. With other inducible systems that are activated by the presence or absence of a particular molecular compound, activating the inducible promoter requires addition of or removal of a molecular compound from the culture medium, thus requiring liquid handling, medium exchange, wash steps and the like. Also, as with the exemplary engine vector shown in FIG. 1D, the editing vector optionally may comprise additional sequences, such as a gene for a selective marker, restriction sites, and the like.

FIG. 1E illustrates the mode of action of a model system comprising the MAD7-SSBct fusion protein where the MAD7-SSBct fusion protein directly recruits repair proteins to double-strand DNA breaks. Note that in this FIG. 1E—in contrast with FIG. 1C—the RGN is fused to the SSBct, which directly recruits RecT/Redβ (i.e., the SSAPs) to the site of the double-strand break. Again, the RGN complex causes a double-strand break in the target DNA which can be resolved by non-homologous end joining (NHEJ) or by strand resection where RecT/Redβ proteins interact with the protein interaction domain (i.e., C-terminal) of SSB (e.g., SSBct) to effect repair of the double-strand break.

FIG. 1F depicts alternative fusions for the nucleic acid nuclease ("RGN")-single-strand binding protein ("SSB") fusion ("RGN-SSB") protein where an exemplary 6×GS linker is positioned between the RGN domain and the SSBct domain of the fusion protein. The length of the C-terminal domain of the SSB used will depend on the specific SSB and the optimal length may be determined by routine experimentation given the guidance provided in this disclosure. For different organisms and different SSBs, RGN fusion proteins are constructed with differing numbers of the C-terminal peptides and with different lengths and types of linkers and these constructs are tested to see which are more efficient at recruiting SSAPs and increasing DNA repair and editing rates. Linkers include a 2 amino acid $[GS]_x$ linker, a 6 amino acid $[GS]_x$ linker, a 10 amino acid $[GS]_x$ linker, a 13 amino acid linker, and the like. Additionally, one to several SSBcts may be present to create the protein interaction domain.

Figure 2A:
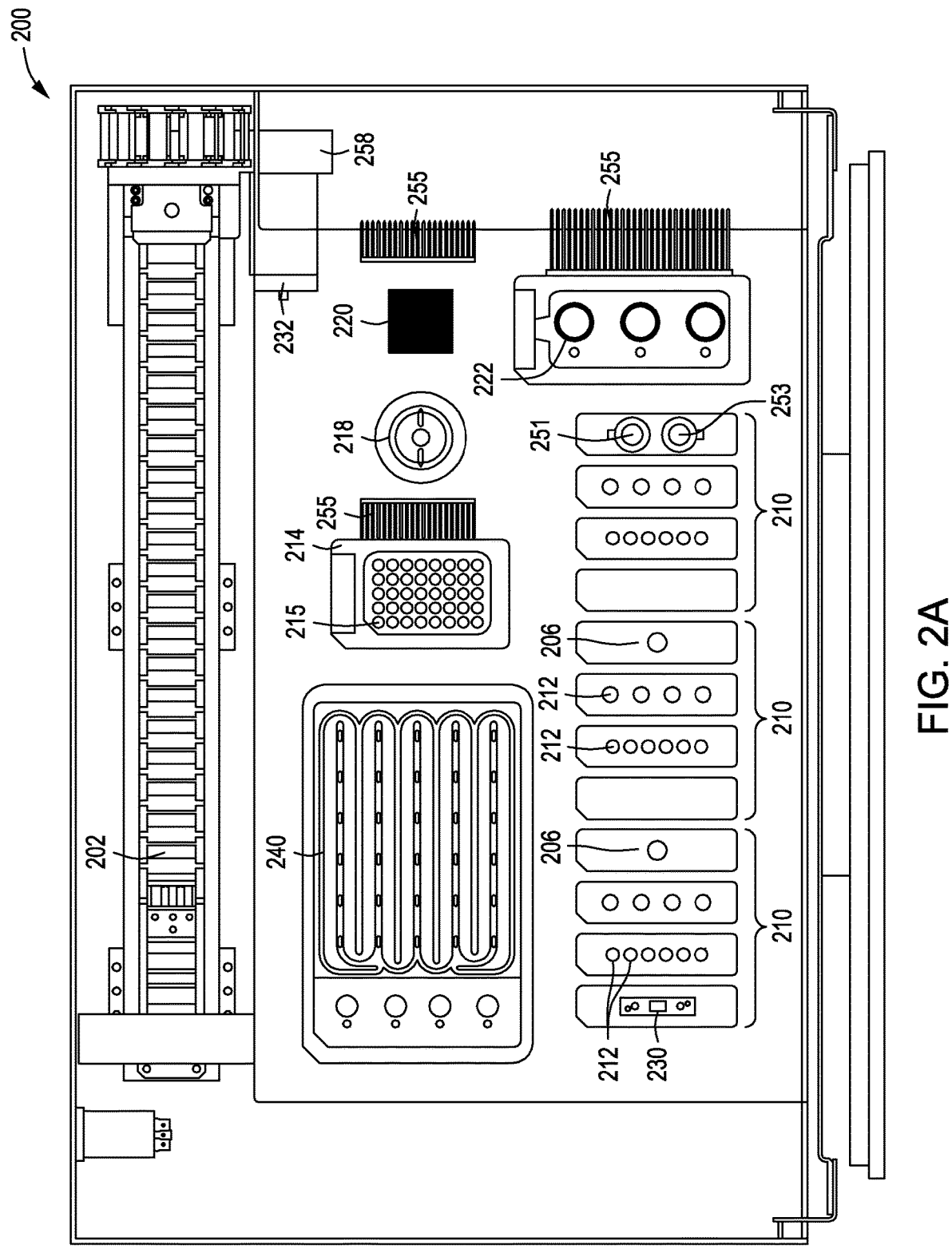
FIGS. 2A-2C depict three different views of an exemplary automated multi-module cell processing instrument for performing nucleic acid-guided nuclease editing.

Automated Cell Editing Instruments and Modules to Perform Nucleic Acid-Guided Nuclease Editing in Cells One Embodiment of an Automated Cell Editing Instrument FIG. 2A depicts an exemplary automated multi-module cell processing instrument 200 to, e.g., perform targeted gene editing of live cells. The instrument 200, for example, may be and preferably is designed as a stand-alone benchtop instrument for use within a laboratory environment. The instrument 200 may incorporate a mixture of reusable and disposable components for performing the various integrated processes in conducting automated genome cleavage and/or editing in cells without human intervention. Illustrated is a gantry 202, providing an automated mechanical motion system (actuator) (not shown) that supplies XYZ axis motion control to, e.g., an automated (i.e., robotic)

liquid handling system 258 including, e.g., an air displacement pipettor 232 which allows for cell processing among multiple modules without human intervention. In an automated multi-module cell processing instruments, the air displacement pipettor 232 is moved by gantry 202 and the various modules and reagent cartridges remain stationary; however, in other embodiments, the liquid handling system 258 may stay stationary while the various modules and reagent cartridges are moved. Also included in the automated multi-module cell processing instrument 200 are reagent cartridges 210 (see, U.S. Pat. Nos. 10,376,889; 10,406,525; 10,478,822; 10,576,474; 10,639,637; 10,738,271; and 10,799,868) comprising reservoirs 212 and transformation module 230 (e.g., a flow-through electroporation (FTEP) device as described in U.S. Pat. Nos. 10,435,713; 10,443,074; and 10,851,389), as well as wash reservoirs 206, cell input reservoir 251 and cell output reservoir 253. The wash reservoirs 206 may be configured to accommodate large tubes, for example, wash solutions, or solutions that are used often throughout an iterative process. Although two of the reagent cartridges 210 comprise a wash reservoir 206 in FIG. 2A, the wash reservoirs instead could be included in a wash cartridge where the reagent and wash cartridges are separate cartridges. In such a case, the reagent cartridge and wash cartridge may be identical except for the consumables (reagents or other components contained within the various inserts) inserted therein.

In some implementations, the reagent cartridges 210 are disposable kits comprising reagents and cells for use in the automated multi-module cell processing/editing instrument 200. For example, a user may open and position each of the reagent cartridges 210 comprising various desired inserts and reagents within the chassis of the automated multi-module cell editing instrument 200 prior to activating cell processing. Further, each of the reagent cartridges 210 may be inserted into receptacles in the chassis having different temperature zones appropriate for the reagents contained therein.

Also illustrated in FIG. 2A is the robotic liquid handling system 258 including the gantry 202 and air displacement pipettor 232. In some examples, the robotic handling system 258 may include an automated liquid handling system such as those manufactured by Tecan Group Ltd. of Mannedorf, Switzerland, Hamilton Company of Reno, Nev., USA (see, e.g., WO2018015544A1), or Beckman Coulter, Inc. of Fort Collins, Colo., USA (see, e.g., US20160018427A1). Pipette tips 215 may be provided in a pipette transfer tip supply 214 for use with the air displacement pipettor 232. The robotic liquid handling system allows for the transfer of liquids between modules without human intervention.

Inserts or components of the reagent cartridges 210, in some implementations, are marked with machine-readable indicia (not shown), such as bar codes, for recognition by the robotic handling system 258. For example, the robotic liquid handling system 258 may scan one or more inserts within each of the reagent cartridges 210 to confirm contents. In other implementations, machine-readable indicia may be marked upon each reagent cartridge 210, and a processing system (not shown, but see element 237 of FIG. 2B) of the automated multi-module cell editing instrument 200 may identify a stored materials map based upon the machine-readable indicia. In the embodiment illustrated in FIG. 2A, a cell growth module comprises a cell growth vial 218 (for details, see U.S. Pat. Nos. 10,435,662; 10,433,031; 10,590,375; 10,717,959; and 10,883,095). Additionally seen is a tangential flow filtration (TFF) module 222 (for details, see U.S. Ser. Nos. 16/516,701 and 16/798,302). Also illustrated as part of the automated multi-module cell processing instrument 200 of FIG. 2A is a singulation module 240 (e.g., a solid wall isolation, incubation and normalization device (SWIIN device) is shown here and described in detail in U.S. Pat. Nos. 10,533,152; 10,633,626; 10,633,627; 10,647,958; 10,723,995; 10,801,008; 10,851,339; 10,954,485; 10,532,324; 10,625,212; 10,774,462; and 10,835,869), served by, e.g., robotic liquid handing system 258 and air displacement pipettor 232. Additionally seen is a selection module 220 which may employ magnet separation. Also note the placement of three heatsinks 255.

Figure 2B:
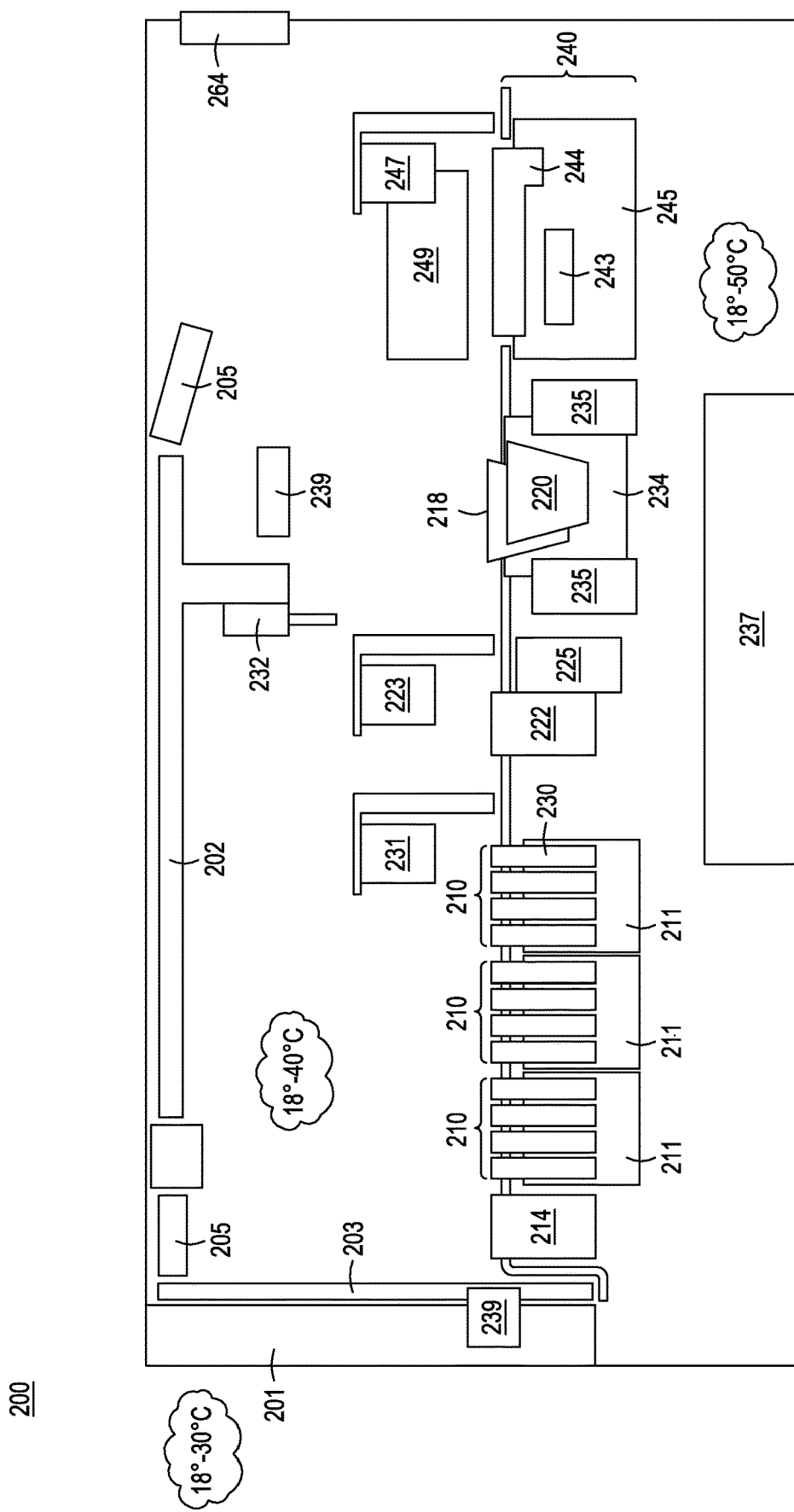

FIG. 2B is a simplified representation of the contents of the exemplary multi-module cell processing instrument 200 depicted in FIG. 2A. Cartridge-based source materials (such as in reagent cartridges 210), for example, may be positioned in designated areas on a deck of the instrument 200 for access by an air displacement pipettor 232 on gantry 202. The deck of the multi-module cell processing instrument 200 may include a protection sink (not shown) such that contaminants spilling, dripping, or overflowing from any of the modules of the instrument 200 are contained within a lip of the protection sink. Also seen are reagent cartridges 210, which are shown disposed with thermal assemblies 211 which can create temperature zones appropriate for different reagents in different regions. Note that one of the reagent cartridges also comprises a flow-through electroporation device 230 (FTEP), served by FTEP interface (e.g., manifold arm) and actuator 231. Also seen is TFF module 222 with adjacent thermal assembly 225, where the TFF module is served by TFF interface (e.g., manifold arm) and actuator 223. Thermal assemblies 225, 235, and 245 encompass thermal electric devices such as Peltier devices, as well as heatsinks, fans and coolers. The rotating growth vial 218 is within a growth module 234, where the growth module is served by two thermal assemblies 235. A selection module is seen at 220. Also seen is the SWIIN module 240, comprising a SWIIN cartridge 244, where the SWIIN module also comprises a thermal assembly 245, illumination 243 (in this embodiment, backlighting), evaporation and condensation control 249, and where the SWIIN module is served by SWIIN interface (e.g., manifold arm) and actuator 247. Also seen in this view is touch screen display 201, display actuator 203, illumination 205 (one on the side of multi-module cell processing instrument 200), and cameras 239 (one camera on either side of multi-module cell processing instrument 200). Finally, element 237 comprises electronics, such as a processor, circuit control boards, high-voltage amplifiers, power supplies, and power entry; as well as pneumatics, such as pumps, valves and sensors.

Figure 2C:
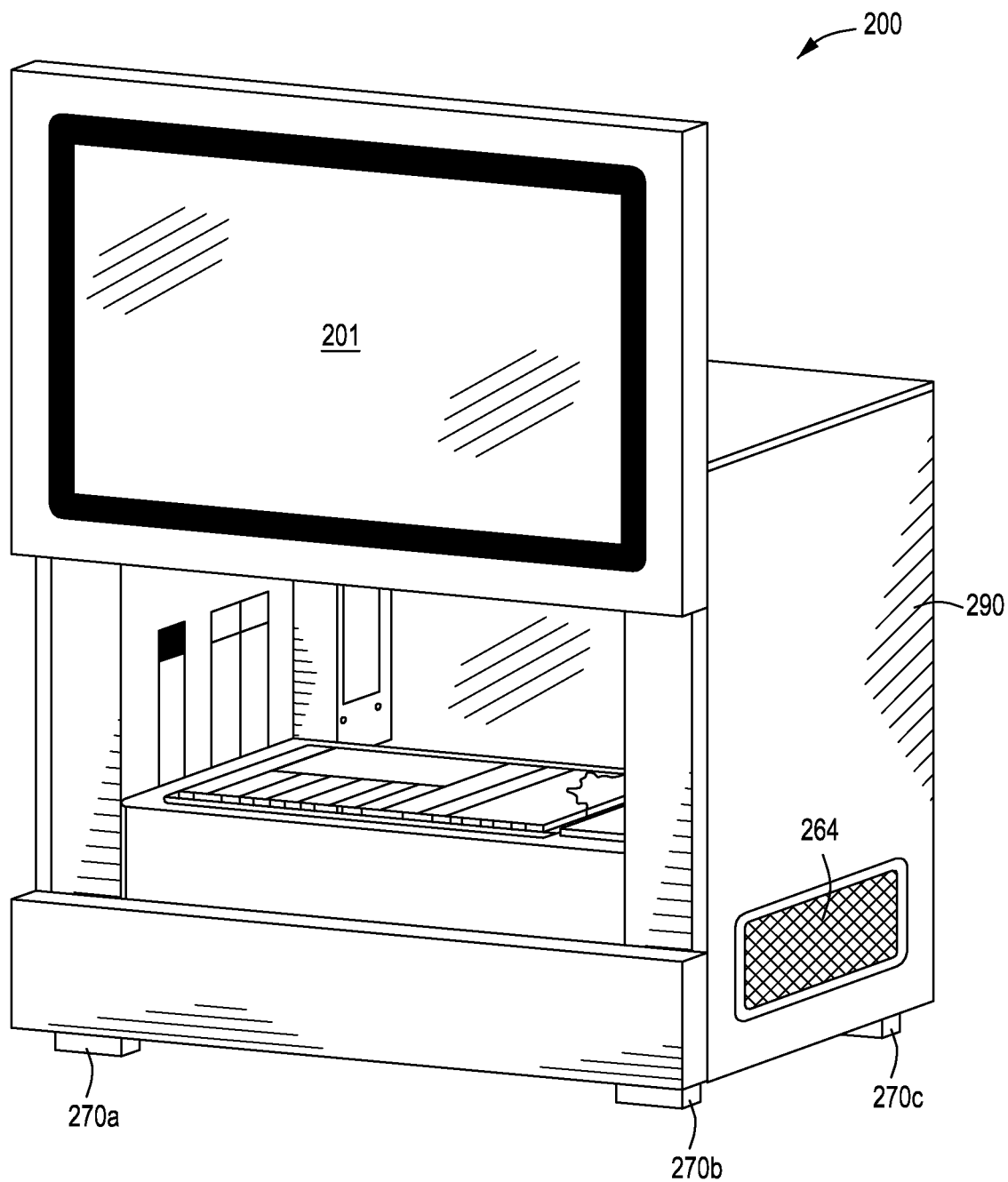

FIG. 2C illustrates a front perspective view of multi-module cell processing instrument 200 for use in as a benchtop version of the automated multi-module cell editing instrument 200. For example, a chassis 290 may have a width of about 24-48 inches, a height of about 24-48 inches and a depth of about 24-48 inches. Chassis 290 may be and preferably is designed to hold all modules and disposable supplies used in automated cell processing and to perform all processes required without human intervention; that is, chassis 290 is configured to provide an integrated, stand-alone automated multi-module cell processing instrument. As illustrated in FIG. 2C, chassis 290 includes touch screen display 201, cooling grate 264, which allows for air flow via an internal fan (not shown). The touch screen display provides information to a user regarding the processing status of the automated multi-module cell editing instrument 200 and accepts inputs from the user for conducting the cell processing. In this embodiment, the chassis 290 is lifted by adjustable feet 270*a*, 270*b*, 270*c* and 270*d* (feet 270*a*-270*c* are shown in this FIG. 2C). Adjustable feet 270*a*-270*d*, for example, allow for additional air flow beneath the chassis 290.

Inside the chassis 290, in some implementations, will be most or all of the components described in relation to FIGS. 2A and 2B, including the robotic liquid handling system disposed along a gantry, reagent cartridges 210 including a flow-through electroporation device, a rotating growth vial 218 in a cell growth module 234, a tangential flow filtration module 222, a SWIIN module 240 as well as interfaces and actuators for the various modules. In addition, chassis 290 houses control circuitry, liquid handling tubes, air pump controls, valves, sensors, thermal assemblies (e.g., heating and cooling units) and other control mechanisms. For examples of multi-module cell editing instruments, see U.S. Pat. Nos. 10,253,316; 10,329,559; 10,323,242; 10,421,959; 10,465,185; 10,519,437; 10,584,333; 10,584,334; 10,647, 982; 10,689,645; 10,738,301; 10,738,663; 10,947,532; 10,894,958; 10,954,512; and 11,034,953, all of which are herein incorporated by reference in their entirety.

Alternative Embodiment of an Automated Cell Editing Instrument

A bioreactor may be used to grow cells off-instrument or to allow for cell growth and recovery on-instrument; e.g., as one module of a multi-module fully-automated closed instrument. Further, the bioreactor supports cell selection/enrichment, via expressed antibiotic markers in the growth process or via expressed antibodies coupled to magnetic beads and a magnet associated with the bioreactor. There are many bioreactors known in the art, including those described in, e.g., WO2019/046766; U.S. Pat. Nos. 10,699, 519; 10,633,625; 10,577,576; 10,294,447; 10,240,117; 10,179,898; 10,370,629; and 9,175,259; and those available from Lonza Group Ltd. (Basel, Switzerland); Miltenyi Biotec (Bergisch Gladbach, Germany), Terumo BCT (Lakewood, CO, USA) and Sartorius GmbH (Gottingen, Germany).

Figure 3A:
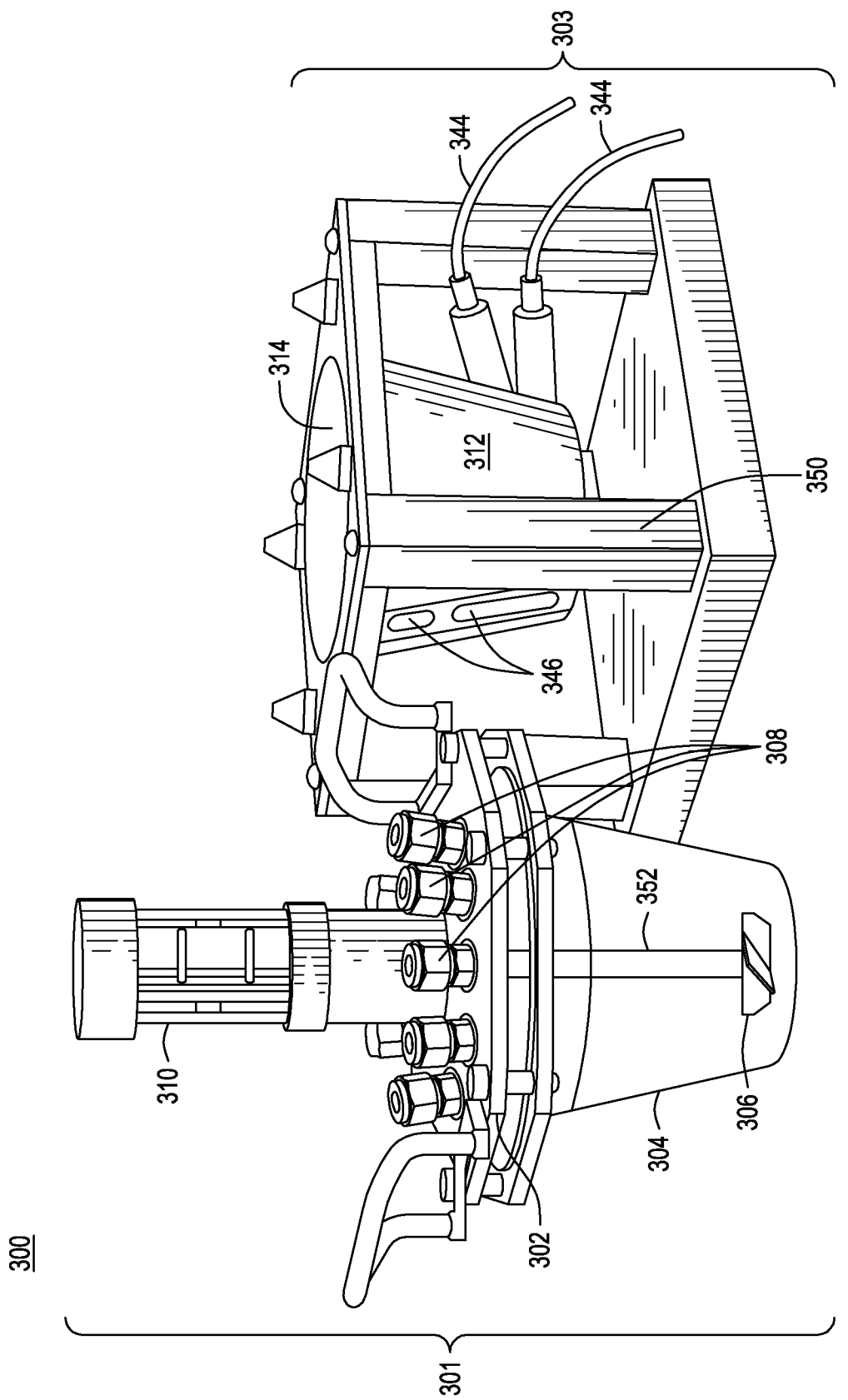
FIGS. 3A-3C depict various view and components of exemplary embodiments of a bioreactor module included in an integrated instrument useful for growing and transfecting cells.

FIG. 3A shows one embodiment of a bioreactor assembly 300 suitable for cell growth, transfection, and editing in the automated multi-module cell processing instruments described herein. Unlike most bioreactors that are used to support fermentation or other processes with an eye to harvesting the products produced by organisms grown in the bioreactor, the present bioreactor (and the processes performed therein) is configured to grow cells, monitor cell growth (via, e.g., optical means or capacitance), passage cells, select cells, transfect cells, and support the growth and harvesting of edited cells. Bioreactor assembly 300 comprises cell growth vessel 301 comprising a main body 304 with a lid assembly 302 comprising ports 308, including a motor integration port 310 configured to accommodate a motor to drive impeller 306 via impeller shaft 352. The tapered shape of main body 304 of the growth vessel 301 along with, in some embodiments, dual impellers allows for working with a larger dynamic range of volumes, such as, e.g., up to 500 ml and as low as 100 ml for rapid sedimentation of the microcarriers.

Bioreactor assembly 300 further comprises bioreactor stand assembly 303 comprising a main body 312 and growth vessel holder 314 comprising a heat jacket or other heating means (not shown) into which the main body 304 of growth vessel 301 is disposed in operation. The main body 304 of growth vessel 301 is biocompatible and preferably transparent—in some embodiments, in the UV and IR range as well as the visible spectrum—so that the growing cells can be visualized by, e.g., cameras or sensors integrated into lid assembly 302 or through viewing apertures or slots 346 in the main body 312 of bioreactor stand assembly 303. Camera mounts are shown at 344.

Bioreactor assembly 300 supports growth of cells from a 500,000 cell input to a 10 billion cell output, or from a 1 million cell input to a 25 billion cell output, or from a 5 million cell input to a 50 billion cell output or combinations of these ranges depending on, e.g., the size of main body 304 of growth vessel 301, the medium used to grow the cells, the type and size and number of microcarriers used for growth (if microcarriers are used), and whether the cells are adherent or non-adherent. The bioreactor that comprises assembly 300 supports growth of both adherent and non-adherent cells, wherein adherent cells are typically grown of microcarriers as described in detail in U.S. Ser. No. 17/237,747, filed 24 Apr. 2021. Alternatively, another option for growing mammalian cells in the bioreactor described herein is growing single cells in suspension using a specialized medium such as that developed by ACCELLTA™ (Haifa, Israel). Cells grown in this medium must be adapted to this process over many cell passages; however, once adapted the cells can be grown to a density of >40 million cells/ml and expanded 50-100× in approximately a week, depending on cell type.

Main body 304 of growth vessel 301 preferably is manufactured by injection molding, as is, in some embodiments, impeller 306 and the impeller shaft 352. Impeller 306 also may be fabricated from stainless steel, metal, plastics or the polymers listed infra. Injection molding allows for flexibility in size and configuration and also allows for, e.g., volume markings to be added to the main body 304 of growth vessel 301. Additionally, material from which the main body 304 of growth vessel 301 is fabricated should be able to be cooled to about 4° C. or lower and heated to about 55° C. or higher to accommodate cell growth. Further, the material that is used to fabricate the vial preferably is able to withstand temperatures up to 55° C. without deformation. Suitable materials for main body 304 of growth vessel 301 include cyclic olefin copolymer (COC), glass, polyvinyl chloride, polyethylene, polyetheretherketone (PEEK), polypropylene, polycarbonate, poly(methyl methacrylate (PMMA)), polysulfone, poly(dimethylsiloxane), cyclo-olefin polymer (COP), and co-polymers of these and other polymers. Preferred materials include polypropylene, polycarbonate, or polystyrene. The material used for fabrication may depend on the cell type to be grown, transfected and edited, and be conducive to growth of both adherent and non-adherent cells and workflows involving microcarrier-based transfection. The main body 304 of growth vessel 301 may be reusable or, alternatively, may be manufactured and configured for a single use. In one embodiment, main body 304 of growth vessel 301 may support cell culture volumes of 25 ml to 500 ml, but may be scaled up to support cell culture volumes of up to 3 L.

The bioreactor stand assembly comprises a stand or frame 350, a main body 312 which holds the growth vessel 301 during operation. The stand/frame 350 and main body 312 are fabricated from stainless steel, other metals, or polymer/plastics. The bioreactor stand assembly main body further comprises a heat jacket (not seen in FIG. 3A) to maintain the growth vessel main body 304—and thus the cell culture—at a desired temperature. Additionally, the stand assembly can host a set of sensors and cameras (camera mounts are shown at 344) to monitor cell culture.

Figure 3B:
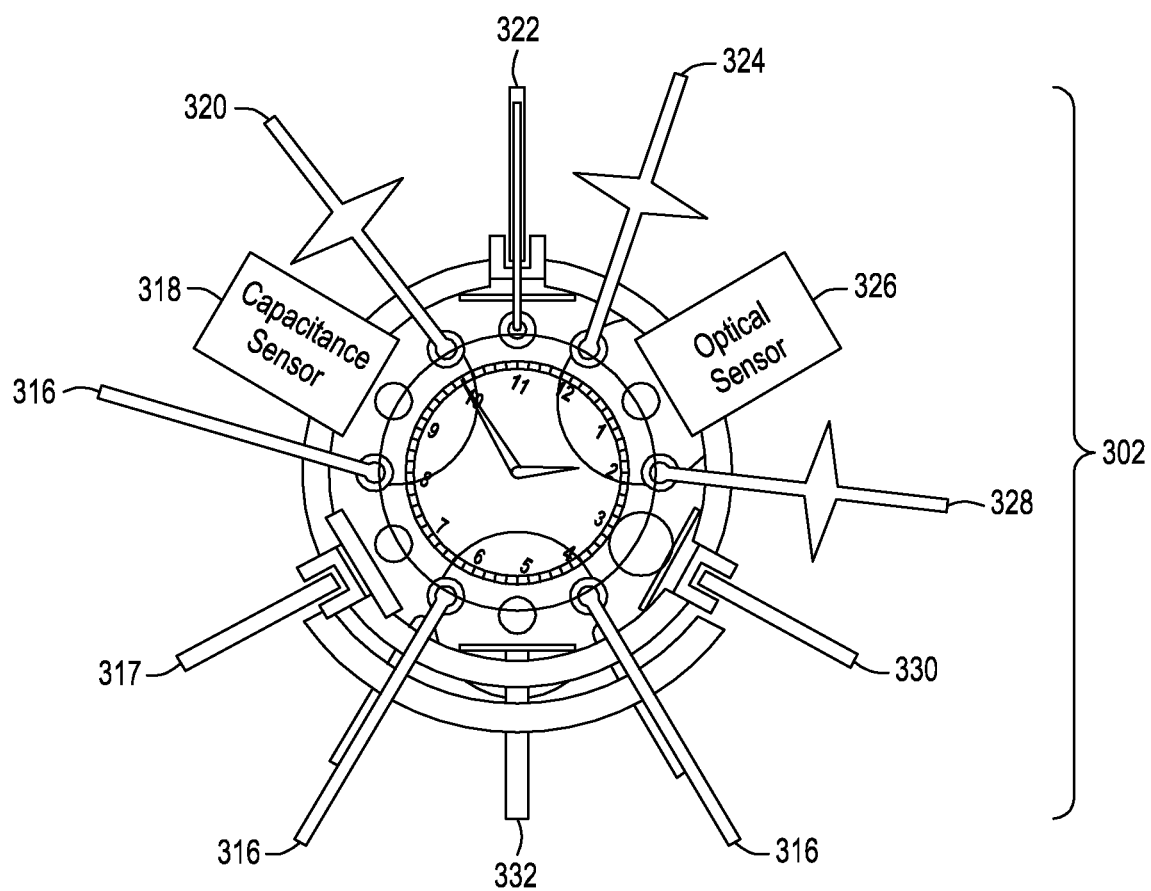

FIG. 3B depicts a top-down view of one embodiment of vessel lid assembly 302. Growth vessel lid assembly 302 is configured to be air-tight, providing a sealed, sterile environment for cell growth, transfection and editing as well as to provide biosafety in a closed system. Vessel lid assembly 302 and the main body 304 of growth vessel 301 can be reversibly sealed via fasteners such as screws, or permanently sealed using biocompatible glues or ultrasonic welding. Vessel lid assembly 302 in some embodiments is fabricated from stainless steel such as S316L stainless steel but may also be fabricated from metals, other polymers (such as those listed supra) or plastics. As seen in this FIG. 3B—as well as in FIG. 3A—vessel lid assembly 302 comprises a number of different ports to accommodate liquid addition and removal; gas addition and removal; for insertion of sensors to monitor culture parameters (described in more detail infra); to accommodate one or more cameras or other optical sensors; to provide access to the main body 304 of growth vessel 301 by, e.g., a liquid handling device; and to accommodate a motor for motor integration to drive one or more impellers 306. Exemplary ports depicted in FIG. 3B include three liquid-in ports 316 (at 5 o'clock, 7 o'clock and 10 o'clock), one liquid-out port 322 (at 12 o'clock), a capacitance sensor 318 (at 10 o'clock), one "gas in" port 324 (at 1 o'clock), one "gas out" port 320 (at 10 o'clock), an optical sensor 326 (at 2 o'clock), a rupture disc 328 at 3 o'clock, two self-sealing ports 317, 330 (at 7 o'clock and 4 o'clock) to provide access to the main body 304 of growth vessel 301; and (a temperature probe 332 (at 6 o'clock).

The ports shown in vessel lid assembly 302 in this FIG. 3B are exemplary only and it should be apparent to one of ordinary skill in the art given the present disclosure that, e.g., a single liquid-in port 316 could be used to accommodate addition of all liquids to the cell culture rather than having a liquid-in port for each different liquid added to the cell culture. Similarly, there may be more than one gas-in port 324, such as one for each gas, e.g., $O_2$, $CO_2$ that may be added. In addition, although a temperature probe 332 is shown, a temperature probe alternatively may be located on the outside of vessel holder 314 of bioreactor stand assembly 303 separate from or integrated into heater jacket (314, 202 not seen in this FIG. 3B). One or more self-sealing ports 317, 330, if present, allow access to the main body 304 of growth vessel 301 for, e.g., a pipette, syringe, or other liquid delivery system via a gantry (not shown). As shown in FIG. 3A, additionally there may be a motor integration port 310 to drive the impeller(s), although other configurations of growth vessel 301 may alternatively integrate the motor drive at the bottom of the main body 304 of growth vessel 301. Growth vessel lid assembly 302 may also comprise a camera port for viewing and monitoring the cells.

Additional sensors include those that detect dissolved $O_2$ concentration, dissolved $CO_2$ concentration, culture pH, lactate concentration, glucose concentration, biomass, and optical density. The sensors may use optical (e.g., fluorescence detection), electrochemical, or capacitance sensing and either be reusable or configured and fabricated for single-use. Sensors appropriate for use in the bioreactor are available from Omega Engineering (Norwalk, Conn., USA); PreSens Precision Sensing (Regensburg, Germany); C-CIT Sensors AG (Waedenswil, Switzerland), and ABER Instruments Ltd. (Alexandria, Va., USA). In one embodiment, optical density is measured using a reflective optical density sensor to facilitate sterilization, improve dynamic range and simplify mechanical assembly. The rupture disc, if present, provides safety in a pressurized environment, and is programmed to rupture if a threshold pressure is exceeded in growth vessel. If the cell culture in the growth vessel is a culture of adherent cells, microcarriers may be used as described in U.S. Ser. No. 17/237,747, filed 24 Apr. 2021. In such an instance, the liquid-out port may comprise a filter such as a stainless steel or plastic (e.g., polyvinylidene difluoride (PVDF), nylon, polypropylene, polybutylene, acetal, polyethylene, or polyamide) filter or frit to prevent microcarriers from being drawn out of the culture during, e.g., medium exchange, but to allow dead cells to be withdrawn from the vessel. Additionally, a liquid port may comprise a filter sipper to allow cells that have been dissociated from microcarriers to be drawn into the cell corral while leaving spent microcarriers in main body of the growth vessel. The microcarriers used for initial cell growth can be nanoporous (where pore sizes are typically <20 nm in size), microporous (with pores between >20 nm to <1 µm in size), or macroporous (with pores between >1 µm in size, e.g. 20 µm) and the microcarriers are typically 50-200 µm in diameter; thus the pore size of the filter or frit in the liquid-out port will differ depending on microcarrier size.

The microcarriers used for cell growth depend on cell type and desired cell numbers, and typically include a coating of a natural or synthetic extracellular matrix or cell adhesion promoters (e.g., antibodies to cell surface proteins or poly-L-lysine) to promote cell growth and adherence. Microcarriers for cell culture are widely commercially available from, e.g., Millipore Sigma, (St. Louis, Mo., USA); ThermoFisher Scientific (Waltham, Mass., USA); Pall Corp. (Port Washington, N.Y., USA); GE Life Sciences (Marlborough, Mass., USA); and Corning Life Sciences (Tewkesbury, Mass., USA). As for the extracellular matrix, natural matrices include collagen, fibrin and vitronectin (available, e.g., from ESBio, Alameda, Calif., USA), and synthetic matrices include MATRIGEL® (Corning Life Sciences, Tewkesbury, Mass., USA), GELTREX™ (ThermoFisher Scientific, Waltham, Mass., USA), CULTREX® (Trevigen, Gaithersburg, Md., USA), biomemetic hydrogels available from Cellendes (Tubingen, Germany); and tissue-specific extracellular matrices available from Xylyx (Brooklyn, N.Y., USA); further, denovoMatrix (Dresden, Germany) offers screenMATRIX™, a tool that facilitates rapid testing of a large variety of cell microenvironments (e.g., extracellular matrices) for optimizing growth of the cells of interest.

Figure 3C:
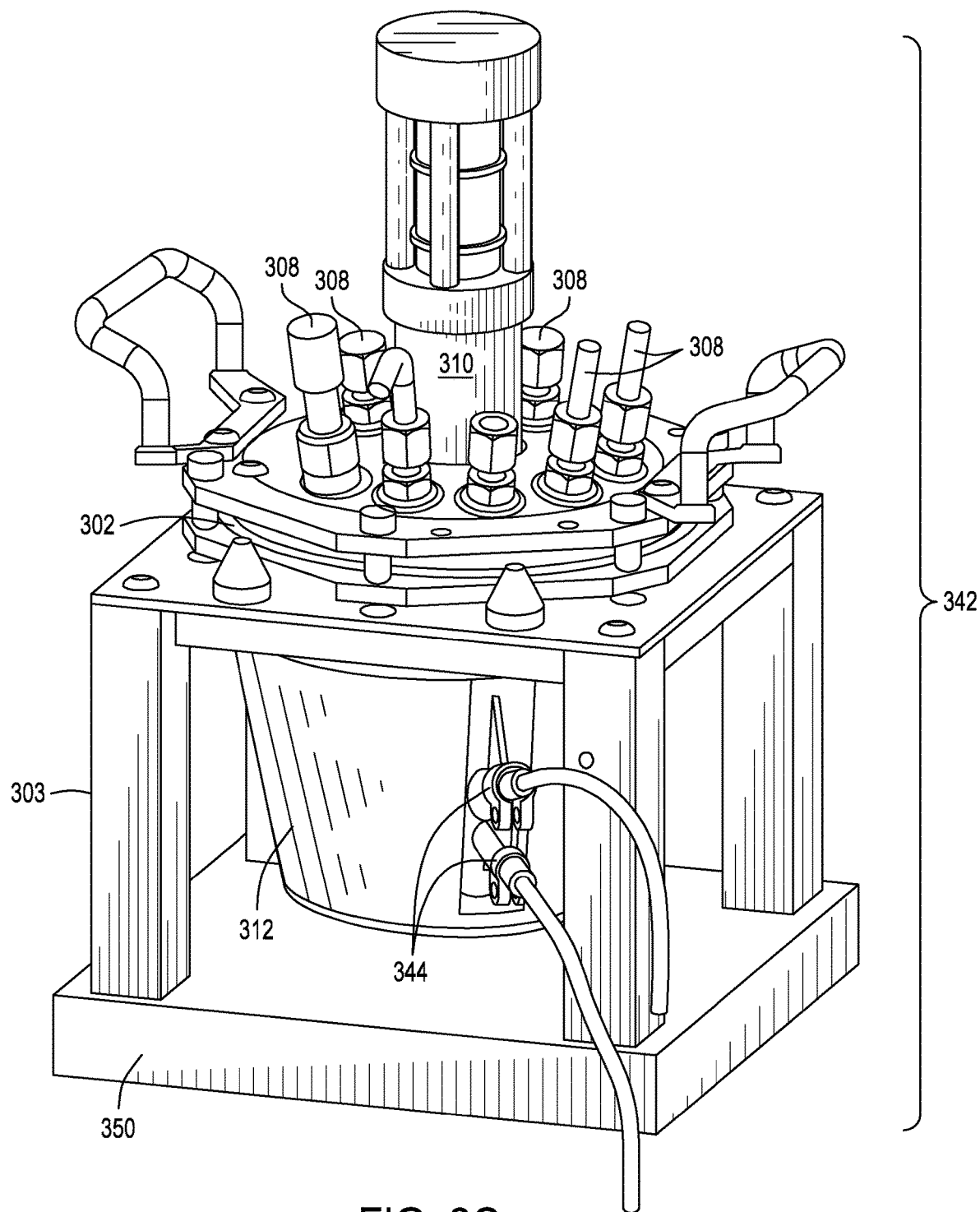

FIG. 3C is a side perspective view of the assembled bioreactor 342 without sensors mounted in ports 308. Seen are vessel lid assembly 302, bioreactor stand assembly 303, bioreactor stand main body 312 into which the main body of growth vessel 301 (not seen in this FIG. 3C) is inserted. Also present are two camera mounts 344, motor integration port 310 and base 350.

Figure 3D:
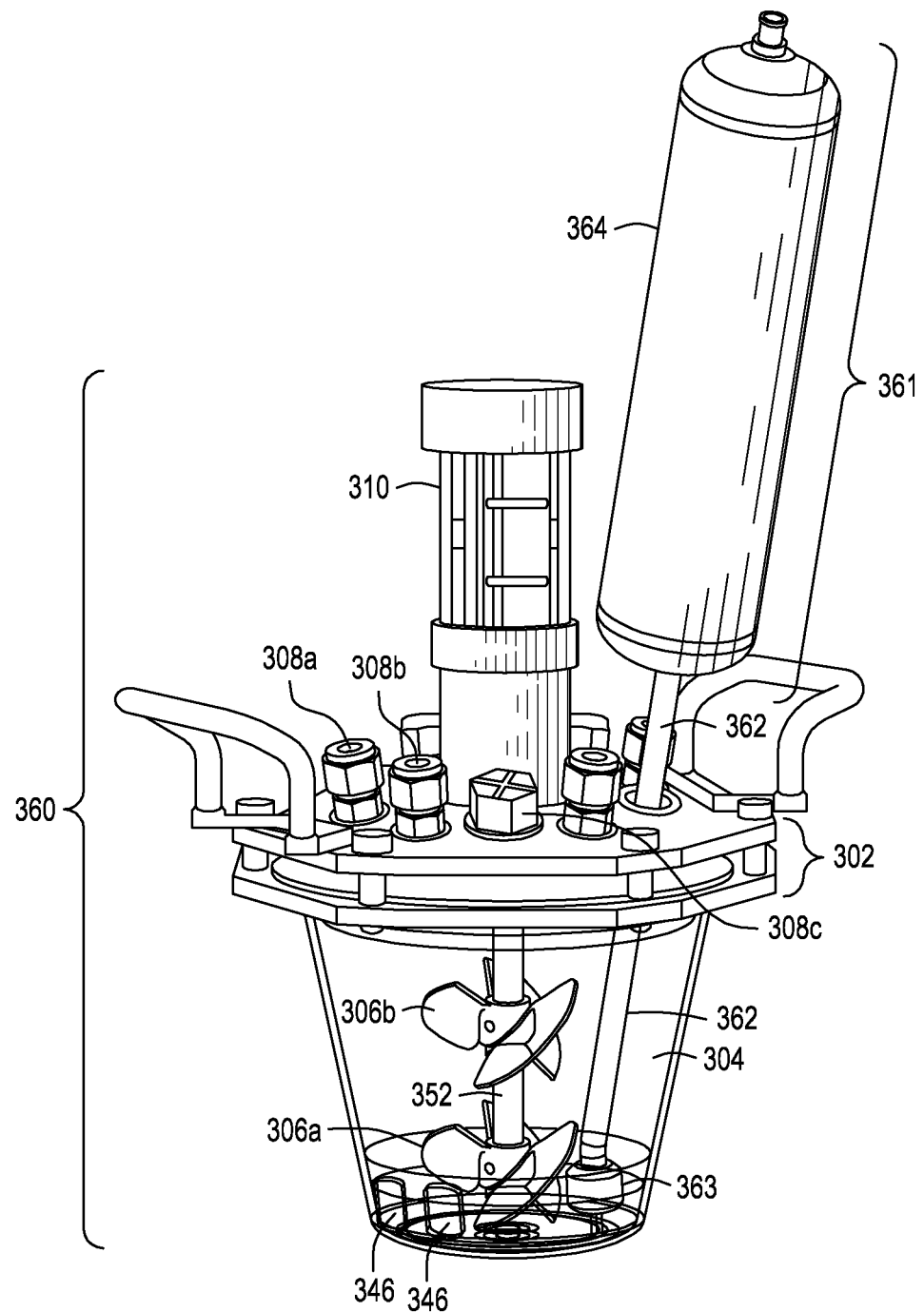
FIGS. 3D and 3E depict an exemplary integrated instrument for growing and transfecting cells.

FIG. 3D shows the embodiment of a bioreactor/cell corral assembly 360, comprising the bioreactor assembly 300 for cell growth, transfection, and editing described in FIG. 3A and further comprising a cell corral 361. Bioreactor assembly comprises a growth vessel comprising tapered a main body 304 with a lid assembly 302 comprising ports 308a, 308b, and 308c, including a motor integration port 310 driving impellers 306a, 306b via impeller shaft 352, as well as two viewing ports 346. Cell corral 361 comprises a main body 364, end caps 373, where the end cap proximal the bioreactor assembly 300 is coupled to a filter sipper 362 comprising a filter portion 363 disposed within the main body 304 of the bioreactor assembly 300. The filter sipper is disposed within the main body 304 of the bioreactor assembly 300 but does not reach to the bottom surface of the bioreactor assembly 300 to leave a "dead volume" for spent microcarriers to settle while cells are removed from the growth vessel 301 into the cell corral 361. The cell corral may or may not comprise a temperature or $CO_2$ probe, and may or not be enclosed within an insulated jacket.

The cell corral 361, like the main body 304 of growth vessel is fabricated from any biocompatible material such as polycarbonate, cyclic olefin copolymer (COC), glass, polyvinyl chloride, polyethylene, polyetheretherketone (PEEK), polypropylene, poly(methyl methacrylate (PMMA)), polysulfone, poly(dimethylsiloxane), cyclo-olefin polymer (COP), and co-polymers of these and other polymers. Likewise, the end caps are fabricated from a biocompatible material such as polycarbonate, cyclic olefin copolymer (COC), glass, polyvinyl chloride, polyethylene, polyetheretherketone (PEEK), polypropylene, poly(methyl methacrylate (PMMA)), polysulfone, poly(dimethylsiloxane), cyclo-olefin polymer (COP), and co-polymers of these and other polymers. The cell corral may be coupled to or integrated with one or more devices, such as a flow cell where an aliquot of the cell culture can be counted. Additionally, the cell corral may comprise additional liquid ports for adding medium, other reagents, and/or fresh microcarriers to the cells in the cell corral. The volume of the main body 364 of the cell corral 361 may be from 25 to 3000 mL, or from 250 to 1000 mL, or from 450 to 500 mL.

In operation, the bioreactor/cell corral assembly 360 comprising the bioreactor assembly 300 and cell corral 361 grows, passages, transfects, and supports editing and further growth of mammalian cells (note, the bioreactor stand assembly is not shown in this FIG. 3D). Cells are transferred to the growth vessel comprising medium and microcarriers. The cells are allowed to adhere to the microcarries. Approximately 2,000,000 microcarriers (e.g., laminin-521 coated polystyrene with enhanced attachment surface treatment) are used for the initial culture of approximately 20 million cells to where there are approximately 50 cells per microcarrier. The cells are grown until there are approximately 500 cells per microcarrier. For medium exchange, the microcarriers comprising the cells are allowed to settle and spent medium is aspirated via a sipper filter, wherein the filter has a mesh small enough to exclude the microcarriers. The mesh size of the filter will depend on the size of the microcarriers and cells present but typically is from 50 to 500 µm, or from 70 to 200 µm, or from 80 to 110 µm. For passaging the cells, the microcarriers are allowed to settle and spent medium is removed from the growth vessel, and phosphobuffered saline or another wash agent is added to the growth vessel to wash the cells on the microcarriers. Optionally, the microcarriers are allowed to settle once again, and some of the wash agent is removed. At this point, the cells are dissociated from the microcarriers. Dissociation may be accomplished by, e.g., bubbling gas or air through the wash agent in the growth vessel, by increasing the impeller speed and/or direction, by enzymatic action (via, e.g., trypsin), or by a combination of these methods. In one embodiment, a chemical agent such as the RelesR™ reagent (STEMCELL Technologies Canada INC., Vancouver, BC) is added to the microcarriers in the remaining wash agent for a period of time required to dissociate most of the cells from the microcarriers, such as from 1 to 60 minutes, or from 3 to 25 minutes, or from 5 to 10 minutes. Once enough time has passed to dissociate the cells, cell growth medium is added to the growth vessel to stop the enzymatic reaction.

Once again, the now-spent microcarriers are allowed to settle to the bottom of the growth vessel and the cells are aspirated through a filter sipper into the cell corral 361. The growth vessel is configured to allow for a "dead volume" of 2 mL to 200 mL, or 6 mL to 50 mL, or 8 mL to 12 mL below which the filter sipper does not aspirate medium to ensure the settled spent microcarriers are not transported to the filter sipper during fluid exchanges. Once the cells are aspirated from the bioreactor vessel leaving the "dead volume" of medium and spent microcarriers, the spent microcarriers are aspirated through a non-filter sipper into waste. The spent microcarriers (and the bioreactor vessel) are diluted in phosphobuffered saline or other buffer one or more times, wherein the wash agent and spent microcarriers continue to be aspirated via the non-filter sipper leaving a clean bioreactor vessel. After washing, fresh microcarriers or RBMCs and fresh medium are dispensed into the bioreactor vessel and the cells in the cell corral are dispensed back into the bioreactor vessel for another round of passaging or for transfection and editing, respectively.

Figure 3E:
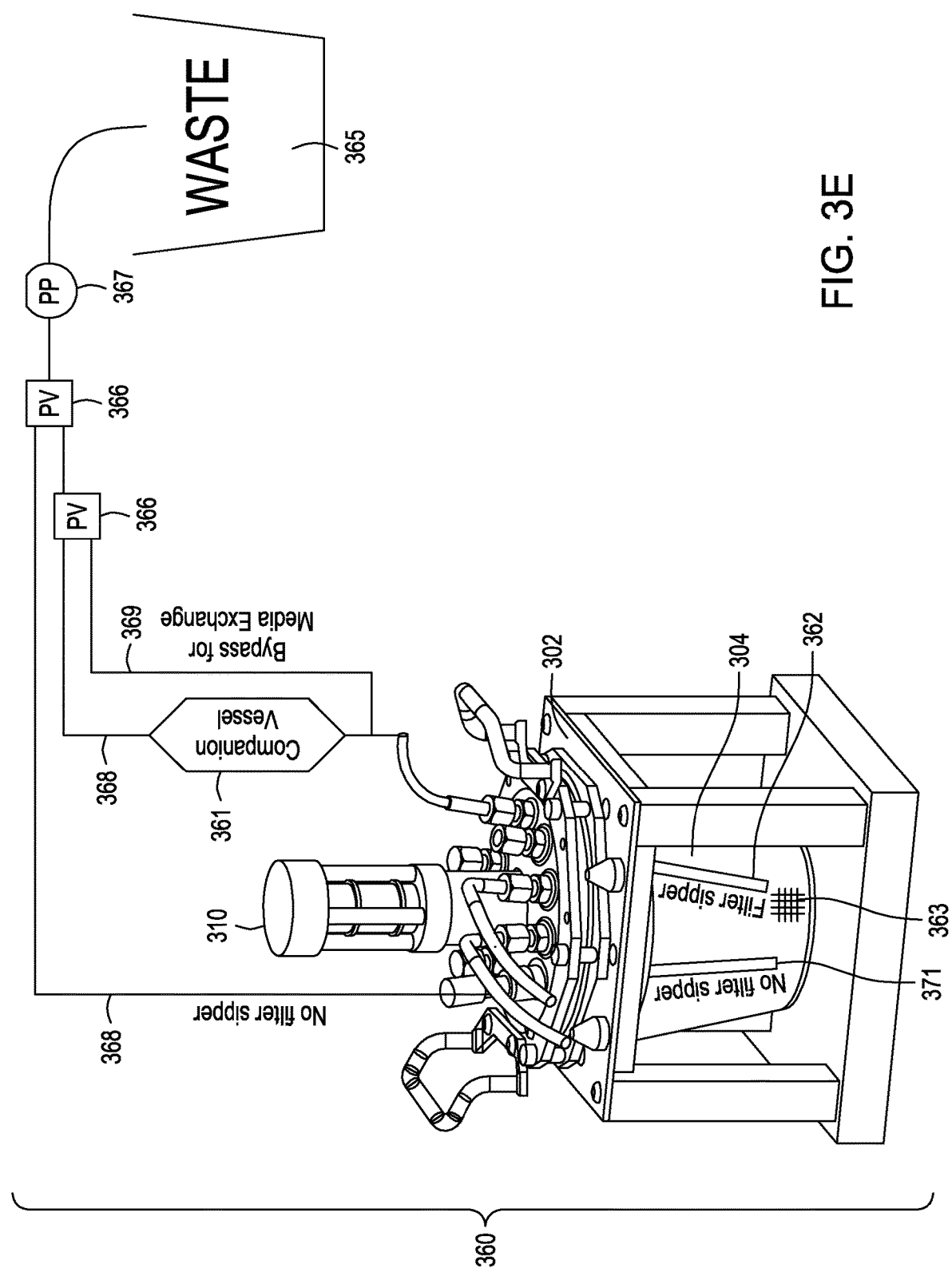

FIG. 3E depicts a bioreactor and bioreactor/cell corral assembly 360 comprising a growth vessel 301, with a main body 304, lid assembly 302 comprising a motor integration port 310, a filter sipper 362 comprising a filter 363 and a no-filter sipper 371. Also seen is a cell corral 361, fluid lines 368 from the cell corral through pinch valve 366, and a line 369 for medium exchange also connected to a pinch valve 366. The no-filter sipper 368 also runs through a pinch valve 366 to waste 365. Also seen is a peristaltic pump 367.

Figure 4A:
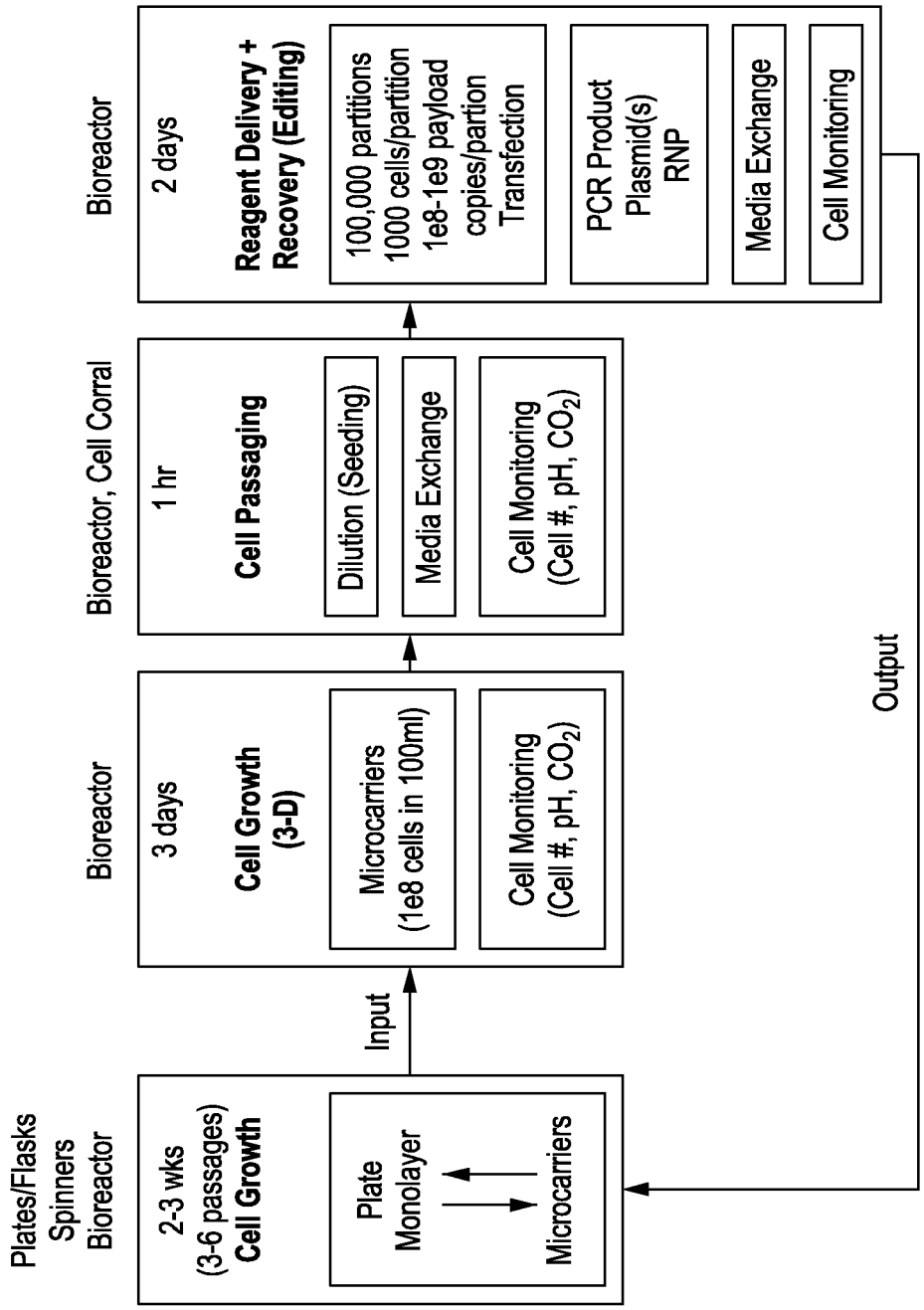
FIG. 4A depicts an exemplary workflow employing microcarrier-partitioned delivery for editing mammalian cells grown in suspension.

Exemplary Embodiments for Delivery of Reagent Bundles to Mammalian Cells in a Bioreactor FIG. 4A depicts an exemplary workflow employing microcarrier-partitioned delivery for editing mammalian cells grown in suspension where the cells are co-localized on reagent bundle microcarriers ("RMBCs") comprising the nucleic acids to be transfected into the cell. In a first step, the cells to be edited are grown for several passages, e.g., off instrument, to assure cell health. The cells may be grown in 2D culture, in 3D culture (if the cells are viable when grown in or adapted to 3D culture) or on microcarriers. This initial cell growth typically takes place off the automated instrument. If necessary, the cells are dissociated and added to medium in the bioreactor comprising cell growth medium such as MEM, DMEM, RPMI, or, for stem cells, mTeSR™ Plus serum-free, feeder-free cell culture medium (STEMCELL Technologies Canada INC., Vancouver, BC, Canada) and cell growth microcarriers. If the cells are grown initially on microcarriers, the microcarriers are transferred to the bioreactor comprising cell growth medium such as mTeSR™ Plus serum-free, feeder-free cell culture medium (STEMCELL Technologies Canada INC., Vancouver, BC, Canada) and additional microcarriers. Approximately 1e7 or 1e8 cells are transferred to the cell growth module on the automated instrument for growth.

In parallel with the off-instrument cell growth, reagent bundle microcarriers (RBMCs) are manufactured, also off-instrument. The present description provides depictions two exemplary methods for manufacturing RBMCs (see FIGS. 4C and 4D) that may be used to edit the cells in the modules and automated instruments described herein.

The cells are grown in 3D culture on microcarriers in the bioreactor for, e.g., three to four days or until a desired number of cells, e.g., 1e8, cells are present. Note that all processes in this FIG. 4A may take place in the bioreactor and cell corral. During this growth cycle, the cells are monitored for cell number, pH, and optionally other parameters. As described above, cell growth monitoring can be performed by imaging, for example, by allowing the microcarriers to settle and imaging the bottom of the bioreactor. Alternatively, an aliquot of the culture may be removed and run through a separate flow cell, e.g., in a separate module, for imaging. For example, the cell corral, in addition to being integrated with the bioreactor vessel, may be integrated with a flow cell or other device for cell counting where an aliquot of the cell culture in the cell corral may be removed and counted in the flow cell.

In another alternative, the cells may express a fluorescent protein and fluorescence in the cell culture is measured or fluorescent dye may be used to stain cells, particularly live cells. This microcarrier-based workflow can be performed in the bioreactor and cell corral with most if not all steps performed in the same device; thus, several bioreactors and cell corrals may be deployed in parallel for two to many samples simultaneously. In yet another alternative, permittivity or capacitance is used to monitor cell coverage on the microcarriers. In yet another embodiment, an aliquot of cells may be removed from the bioreactor or cell corral and transported out of the instrument and manually counted on a commercial cell counter (i.e., Thermofisher Countess, Waltham, Mass., USA).

The microcarriers used for initial cell growth can be nonporous (where pore sizes are typically <20 nm in size), microporous (with pores between >20 nm to <1 μm in size), or macroporous (with pores between >1 μm in size, e.g. 20 μm). In microcarrier culture, cells grow as monolayers on the surface of nonporous or microporous microcarriers, which are typically spherical in morphology; alternatively, the cells grow on the surface and as multilayers in the pores of macroporous microcarriers. The microcarriers preferably have a density slightly greater than that of the culture medium to facilitate easy separation of cells and medium for, e.g., medium exchange and imaging and passaging; yet the density of the microcarriers is also sufficiently low to allow complete suspension of the microcarriers at a minimum stirring or bubbling rate. Maintaining a low stirring or bubbling rate is preferred so as to avoid hydrodynamic damage to the cells.

The microcarriers used for cell growth depend on cell type and desired cell numbers, and typically include a coating of a natural or synthetic extracellular matrix or cell adhesion promoters (e.g., antibodies to cell surface proteins or poly-L-lysine) to promote cell growth and adherence. Microcarriers for cell culture are widely commercially available from, e.g., Millipore Sigma, (St. Louis, Mo., USA); Thermo Fisher (Waltham, Mass., USA); Pall Corp. (Port Washington, N.Y., USA); GE Life Sciences (Marlborough, Mass., USA); and Corning Life Sciences (Tewkesbury, Mass., USA). As for the extracellular matrix, natural matrices include collagen, fibrin and vitronectin (available, e.g., from ESBio, Alameda, Calif., USA), and synthetic matrices include Matrigel® (Corning Life Sciences, Tewkesbury, Mass., USA), Geltrex™ (Thermo Fisher Scientific, Waltham, Mass., USA), Cultrex® (Trevigen, Gaithersburg, Md., USA), biomemetic hydrogels available from Cellendes (Tubingen, Germany); and tissue-specific extracellular matrices available from Xylyx (Brooklyn, N.Y., USA); further, denovoMatrix (Dresden, Germany) offers screenMATRIX™, a tool that facilitates rapid testing of a large variety of cell microenvironments (e.g., extracellular matrices) for optimizing growth of the cells of interest.

Following cell growth, passaging is performed by, e.g., stopping the impeller rotation or bubbling action in the bioreactor and allowing the microcarriers to settle. In one method, the cells are removed from the microcarriers using enzymes such as collagenase, trypsin or pronase, or by non-enzymatic methods including EDTA or other chelating chemicals, and once removed from the carriers, medium is added to dilute the enzyme to inhibit enzymatic action. The dissociation procedures relating to the cell corral are described in detail infra. Once medium is added, then the cells are separated from the microcarriers by allowing the microcarriers to settle and aspirating the cells via a filtered sipper into the cell corral. The cells then may be optionally dissociated from one another via a filter, sieve or by bubbling or other agitation in the cell corral. Next, microcarriers comprising the manufactured reagent bundles (reagent bundle microcarrier microcarriers or RBMCs) and the dissociated cells are combined in an appropriate medium in the growth vessel. Alternatively, instead of removing cells from the cell growth microcarriers and re-seeding on RBMCs, the cells may be transferred from the cell growth microcarriers to RBMCs via microcarrier bridge passaging either in the growth vessel in a reduced volume or in the cell corral. Bridge passaging involves allowing a new microcarrier (e.g. an RBMC) to come into physical contact with a cell-laden microcarrier, such that cells on the latter microcarrier can migrate to the RBMC.

RBMCs are not prepared on-instrument but are pre-manufactured. The microcarriers used for reagent bundles may be microporous microcarriers, which, due to the plethora of micropores, can carry a larger reagent payload per carrier diameter than nonporous or macroporous microcarriers. Preferred RBMCs are microporous, to provide increased surface area for reagent delivery, and functionalized on the surface so as to be able to bind reagents. Preferred microcarriers for RBMCs include Pierce™ Streptavidin UltraLink™ Resin, a cross-linked polyacrylamide carrier functionalized with streptavidin comprising a pore size of 50 to 100 nm; Pierce™ NeutrAvidin™ Plus UltraLink™ Resin, cross-linked polyacrylamide carrier functionalized with avidin comprising a pore size of 50 to 100 nm; and UltraLink™ Hydrazide Resin, a cross-linked polyacrylamide carrier functionalized with hydrazine comprising a pore size of 50 to 100 nm, all available from Thermo Fisher (Waltham, Mass., USA); cross-linked agarose resins with alkyne, azide, photo-cleavable azide and disulfide surface functional groups available from Click Chemistry Tools (Scottsdale, Ariz., USA); Sepharose™ Resin, cross-linked agarose with amine, carboxyl, carbodiimide, N-hydroxysuccinimide (NHS), and epoxy surface functional groups available from GE Health (Chicago, Ill., USA).

The microcarriers are loaded with amplified editing cassettes or amplified editing plasmids, engine plasmids, nuclease, mRNAs or ribonucleoproetins (RNPs) depending on, e.g., the functionalized group, via, e.g., via chemical or photo linkage or depending on a surface coating on the microcarrier, if present. RBMCs are prepared by 1) partitioning and amplifying a single copy of an editing cassette to produce clonal copies in an RBMC, or by 2) pooling and amplifying editing cassettes, followed by dividing the editing cassettes into sub-pools and "pulling down" the amplified editing cassettes with microcarriers comprising nucleic acids specific to and complementary to unique sequences on the editing cassettes. The step of sub-pooling acts to "demultiplex" the editing cassette pool, thereby increasing the efficiency and specificity of the "pull down" process. De-multiplexing thus allows for amplification and error correction of the editing cassettes to be performed in bulk followed by efficient loading of clonal copies of the editing cassettes onto a microcarrier.

Figure 4B:
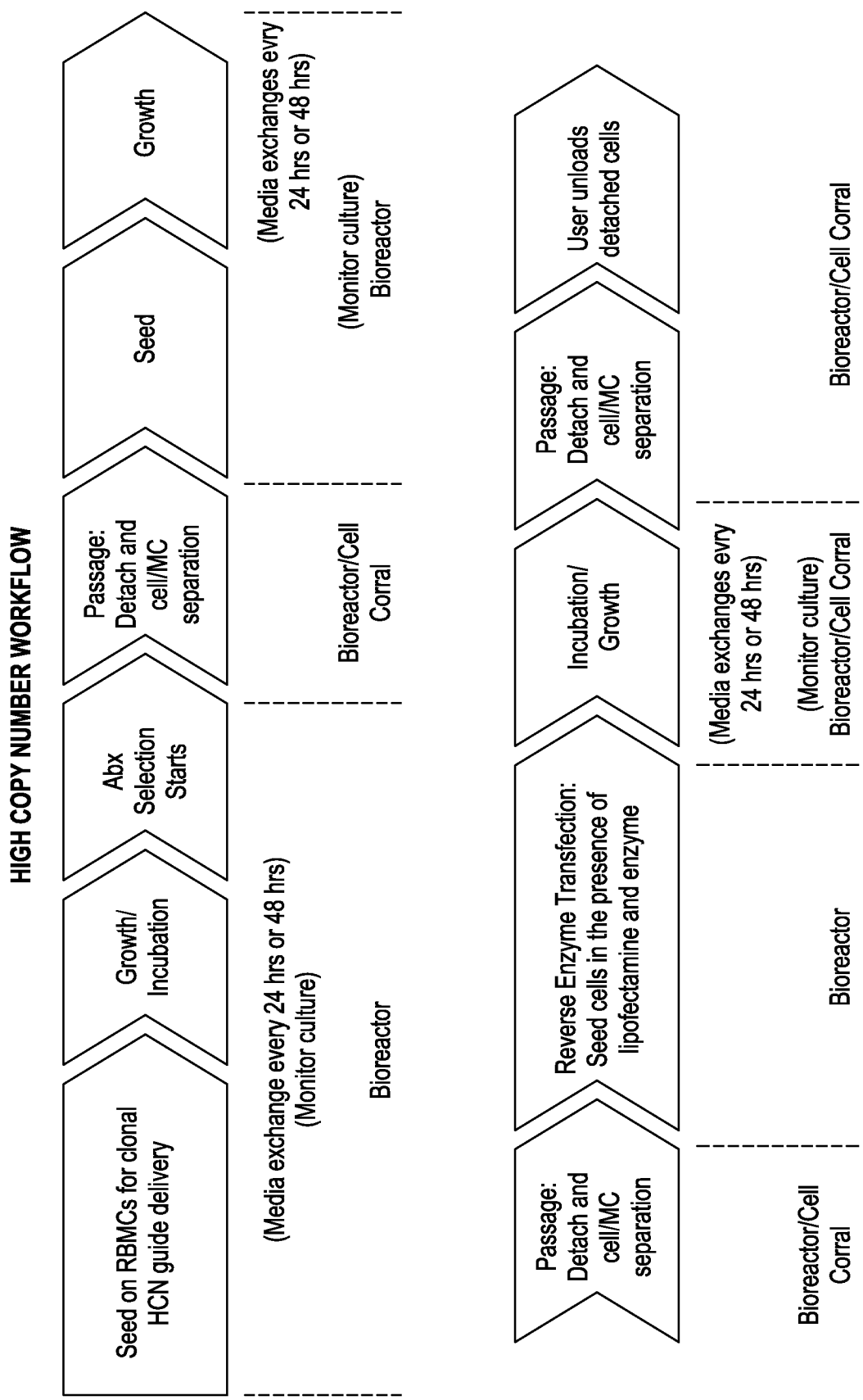
FIG. 4B depicts an option for growing, passaging, transfecting and editing iPSCs involving sequential transfection of editing cassettes and nuclease.

FIG. 4B depicts an exemplary option for growing, passaging, transfecting and editing iPSCs (induced pluripotent stem cells), where there is sequential delivery of clonal high copy number (HCN) RBMCs—i.e., lipid nanoparticle-coated microcarriers, where each microcarrier is coated with many copies of delivery vehicles (e.g., RNA, DNA, plasmid, or ribonucleoprotein) carrying a single clonal editing cassette—followed by bulk enzyme delivery. Note that the bioreactors and cell corrals described infra may be used for all processes. Following the workflow of FIG. 1B, first cells are seeded on the RBMCs to deliver clonal copies of nucleic acids to the cells. Again, the RBMCs are typically fabricated or manufactured off-instrument. The cells are allowed to grow and after 24-48 hours, medium is exchanged for medium containing antibiotics to select for cells that have been transfected. The cells are passaged, re-seeded and grown again, and then passaged and re-seeded, this time onto microcarriers comprising lipofectamine with the enzyme provided as a coding sequence under the control of a promoter, or as a protein on the surface of a microcarrier. As an alternative, the enzyme may be provided in bulk in solution. The enzyme is taken up by the cells on the microcarriers, and the cells are incubated and allowed to grow. Medium is exchanged as needed and the cells are detached from the microcarriers for subsequent growth and analysis.

An alternative exemplary option for the method shown in FIG. 4B comprises the steps of growing, passaging, transfecting and editing iPSCs. In this embodiment, there is simultaneous delivery of clonal high copy number (HCN) RBMCs (i.e., reagent bundle lipid nanoparticle-coated microcarriers) where each microcarrier is coated with many copies of delivery vehicles (e.g., RNA, DNA, plasmid, or ribonucleoprotein) carrying a single clonal editing cassette and enzyme (e.g., as a coding sequence under the control of a promoter therefor, as a ribonucleoprotein complex, or as a protein). Again, the RBMCs are typically fabricated or manufactured off-instrument. Note that the integrated instrument described infra may be used for all processes. As with the workflow shown in FIG. 4B, first cells are seeded on microcarriers to grow. The cells are then passaged, detached, re-seeded, grown and detached again to increase cell number, with medium exchanged every 24-48 or 24-72 hours as needed. Following detachment, the cells are seeded on RBMCs for clonal delivery of the editing cassette and enzyme in a co-transfection reaction. Following transfection, the cells grown for 24-48 hours after which medium is exchanged for medium containing antibiotics for selection. The cells are selected and passaged, re-seeded and grown again. Medium is exchanged as needed and the cells are detached from the microcarriers for subsequent growth and analysis.

Figure 4C:
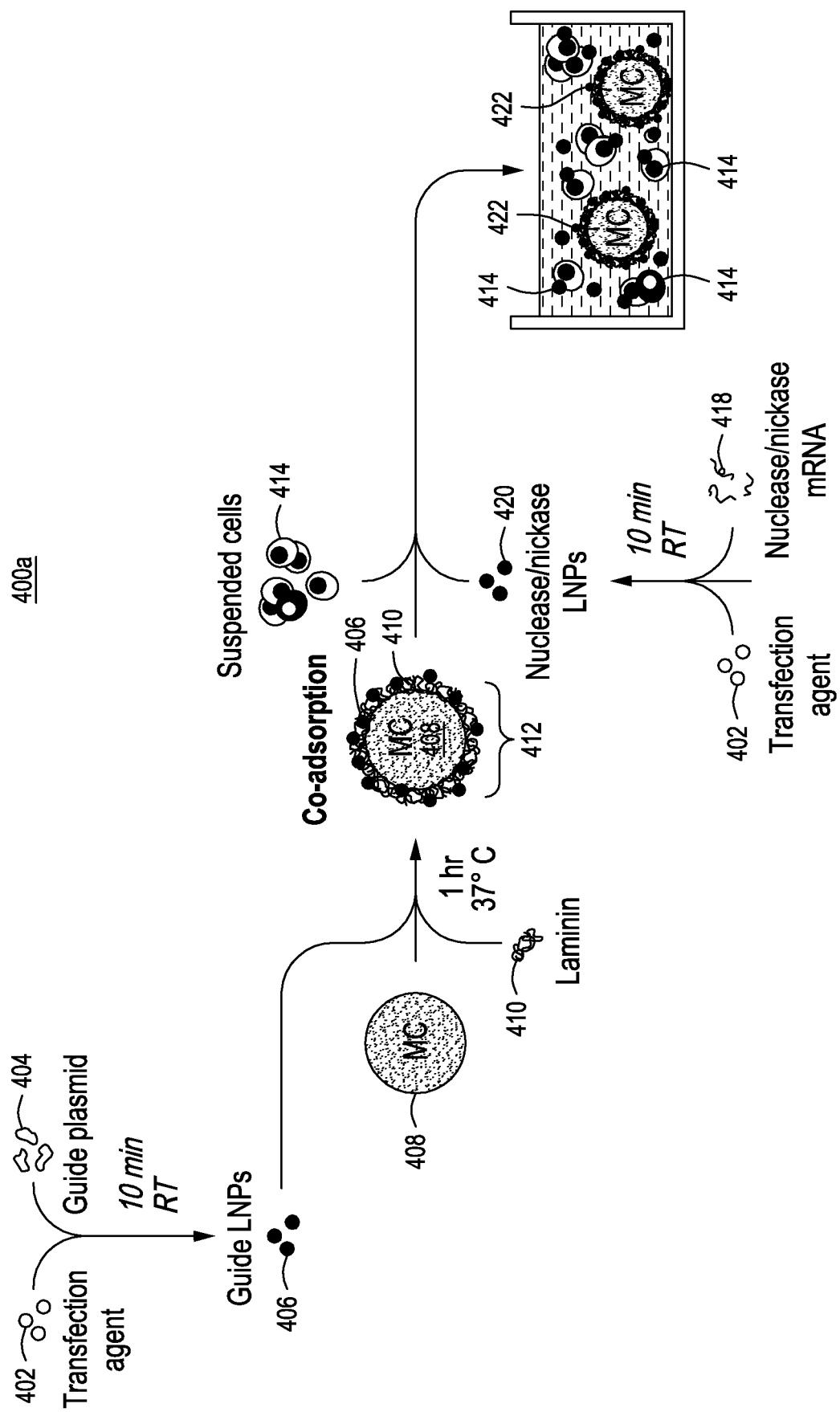
FIG. 4C depicts an exemplary workflow employing microcarrier-partitioned delivery for editing mammalian cells.
Figure 4D:
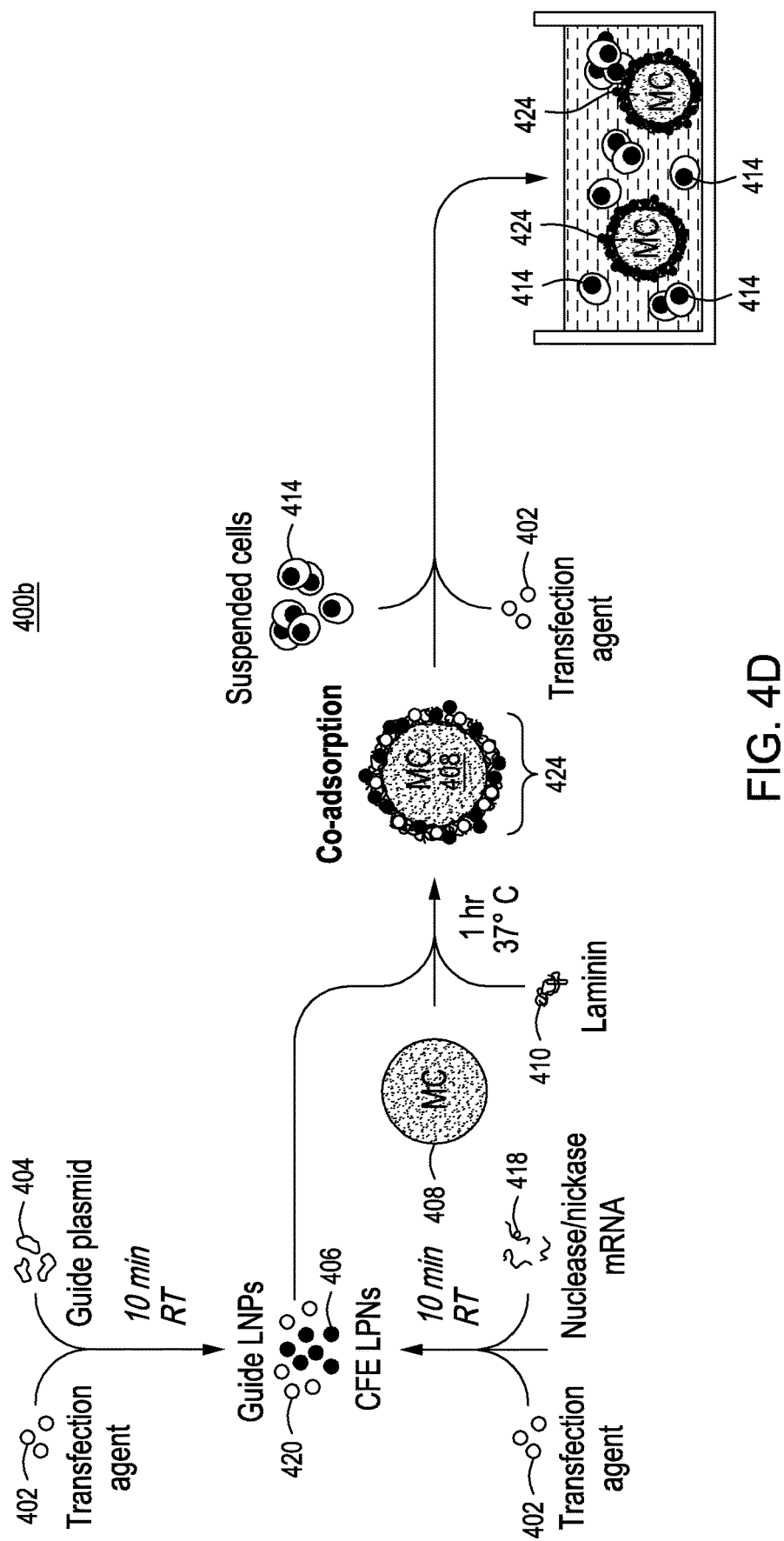
FIG. 4D depicts an alternative workflow employing microcarrier-partitioned delivery for editing mammalian cells.

FIGS. 4C and 4D depict alternative methods for populating microcarriers with a lipofectamine/nucleic acid payload and cells. In the method 400a shown in FIG. 4C at top left, lipofectamine 402 and guide plasmid payloads 404 are combined and guide LNPs (lipofectamine nucleic acid payloads) 406 are formed in solution. In parallel, microcarriers 408 ("MCs") are combined with a coating such as laminin 521 410 to foster adsorption and cell attachment. The laminin 521-coated microcarriers are then combined with the guide LNPs 406 to form partially-loaded microcarriers 412. The processes of forming RBMCs (i.e., the partially-loaded microcarriers 412 comprising the guide LNPs 406) to this point are typically performed off-instrument. In parallel and typically off-instrument, nuclease LNPs 420 are formed by combining lipofectamine 402 and nuclease mRNA 418. The nuclease LNPs 420 are combined with the partially-loaded microcarriers 412 and adsorb onto the partially-loaded microcarriers 412 to form fully-loaded RBMCs 422 comprising both the guide LNPs 406 and the nuclease LNPs 420. At this point, the mammalian cells 414 have been grown and passaged in the bioreactor and cell corral several to many times. The cells 414 populate the fully-loaded RBMCs 422, where the cells 414 then take up (i.e., are transfected by) the guide LNPs 406 and the nuclease LNPs 420, a process that may take several hours up to several days. At the end of the transfection process, transfected mammalian cells reside on the surface of the fully-loaded microcarriers 422.

As an alternative to the method 400a shown in FIG. 4C, FIG. 4D depicts method 400b which features simultaneous adsorption of the guide LNPs and the nuclease LNPs. Again, lipofectamine 402 and guide plasmid payloads 404 are combined where guide LNPs (lipofectamine nucleic acid payloads) 406 are formed in solution. In parallel, nuclease LNPs 420 are formed by combining lipofectamine 402 and nuclease mRNA 418. Also in parallel, microcarriers 408 are combined with a coating such as laminin 521 410 to foster adsorption and cell attachment. The laminin 521-coated microcarriers are simultaneously combined with both the guide LNPs 406 and the nuclease LNPs 420 to form fully-loaded microcarriers 424 where both the guide LNPs 406 and the nuclease LNPs 420 co-adsorb onto the surface of the laminin-coated microcarriers. The processes of forming RBMCs (i.e., the fully-loaded microcarriers 424 comprising both the guide LNPs 406 and the nuclease LNPs 420) to this point are typically performed off-instrument.

At this point, the fully-loaded microcarriers 424 comprising the guide LNPs 406 and the nuclease LNPs 420 are added to medium in the bioreactor comprising the mammalian cells 414 to be transfected, optionally with additional lipofect reagent 402. The mammalian cells 414 have been grown and passaged in the bioreactor and cell corral one to many times. The cells 414 populate the fully-loaded RBMCs 424, where the cells 414 then take up (i.e., are transfected by) the guide LNPs 406 and the nuclease LNPs 420, a process that may take several hours up to several days. At the end of the transfection process, transfected mammalian cells reside on the surface of the fully-loaded microcarriers 424. In these exemplary methods, nuclease mRNAs are used to form the nuclease LNPs; however, the nuclease enzymes may be loaded on to form LNPs, or gRNAs and nuclease enzymes may be loaded in the form of RNPs on the LNPs.

Use of the Automated Multi-Module Cell Processing Instrument

Figure 5:
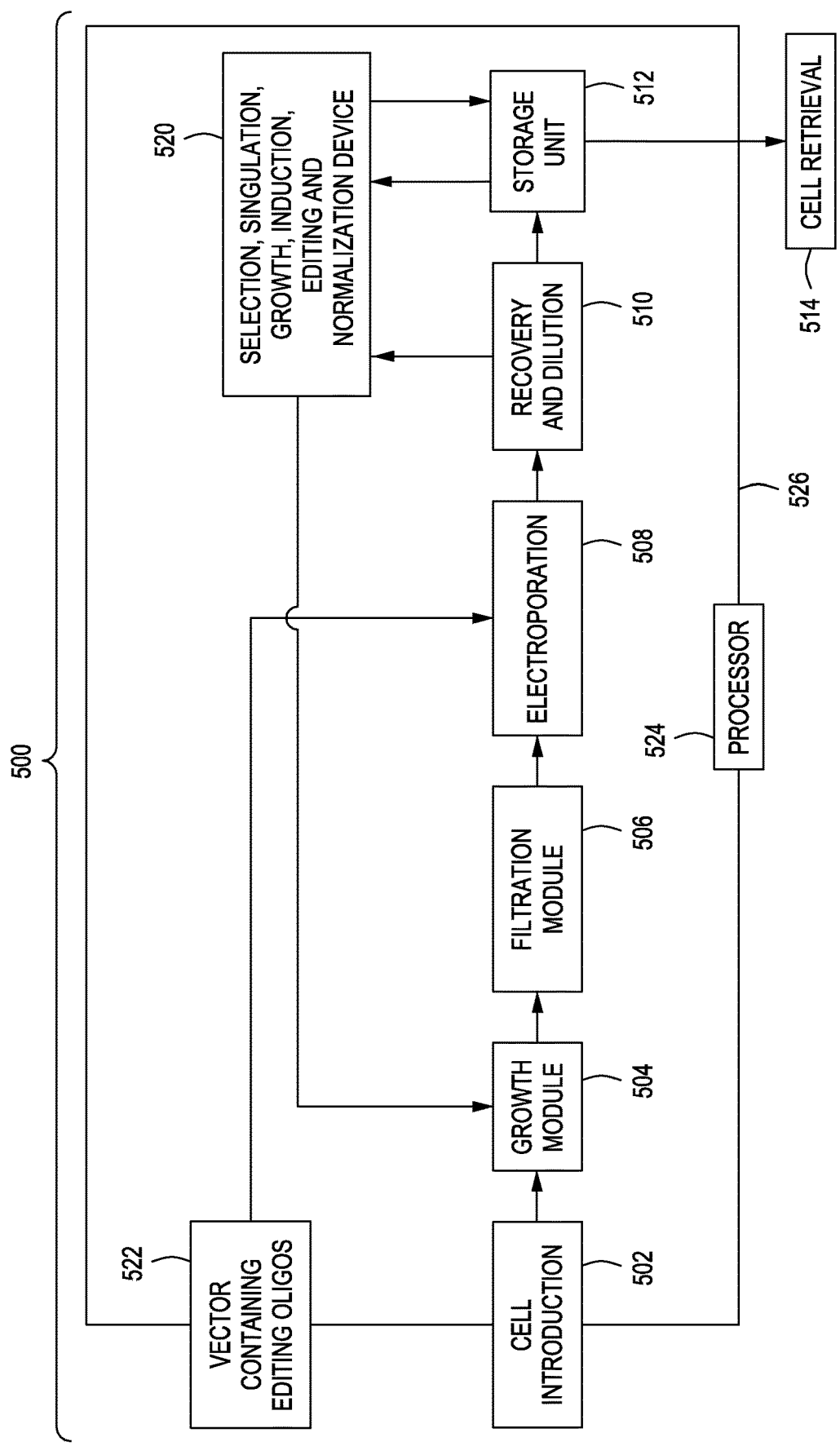
FIG. 5 is a simplified block diagram of an embodiment of an exemplary automated multi-module cell processing instrument comprising a solid wall singulation/growth/editing/normalization module for recursive cell editing.

FIG. 5 illustrates an embodiment of a multi-module cell processing instrument. This embodiment depicts an exemplary system that performs recursive gene editing on a cell population. The cell processing instrument 500 may include a housing 526, a reservoir for storing cells to be transformed or transfected 502, and a cell growth module (comprising, e.g., a rotating growth vial) 504. The cells to be transformed are transferred from a reservoir to the cell growth module to be cultured until the cells hit a target OD. Once the cells hit the target OD, the growth module may cool or freeze the cells for later processing or transfer the cells to a cell concentration module 506 where the cells are subjected to buffer exchange and rendered electrocompetent, and the volume of the cells may be reduced substantially. Once the cells have been concentrated to an appropriate volume, the cells are transferred to electroporation device 508. In addition to the reservoir for storing cells 512, the multi-module cell processing instrument includes a reservoir for storing the vector pre-assembled with editing oligonucleotide cassettes 522. There is also a vessel for cell retrieval 514. The pre-assembled nucleic acid vectors are transferred to the electroporation device 508, which already contains the cell culture grown to a target OD. In the electroporation device 508, the nucleic acids are electroporated into the cells.

Following electroporation, the cells are transferred into an optional recovery module 510, where the cells recover briefly post-transformation.

After recovery, the cells may be transferred to a storage module 512, where the cells can be stored at, e.g., 4° C. for later processing, or the cells may be diluted and transferred to a selection/singulation/growth/induction/editing/normalization (SWIIN) module 520. In the SWIIN 520, the cells are arrayed such that there is an average of one cell per microwell. The arrayed cells may be in selection medium to select for cells that have been transformed or transfected with the editing vector(s). Once singulated, the cells grow through 2-50 doublings and establish colonies. Once colonies are established, editing is induced by providing conditions (e.g., temperature, addition of an inducing or repressing chemical) to induce editing. Once editing is initiated and allowed to proceed, the cells are allowed to grow to terminal size (e.g., normalization of the colonies) in the microwells and then the cells are treated to conditions that cure the editing vector from this round. Once cured, the cells can be flushed out of the microwells and pooled, then transferred to the storage (or recovery) unit 512 or can be transferred back to the growth module 504 for another round of editing. In between pooling and transfer to a growth module, there typically is one or more additional steps, such as cell recovery, medium exchange (rendering the cells electrocompetent), cell concentration (typically concurrently with medium exchange by, e.g., filtration. Note that the selection/singulation/growth/induction/editing/normalization and editing modules may be the same module, where all processes are performed in, e.g., a solid wall device, or selection and/or dilution may take place in a separate vessel before the cells are transferred to the solid wall singulation/growth/induction/editing/normalization/editing module (solid wall device). Similarly, the cells may be pooled after normalization, transferred to a separate vessel, and cured in the separate vessel. Once the putatively-edited cells are pooled, they may be subjected to another round of editing, beginning with growth, cell concentration and treatment to render electrocompetent, and transformation by yet another repair template in another editing cassette via the electroporation module 508.

In electroporation device 508, the cells selected from the first round of editing are transformed by a second set of editing oligos (or other type of oligos) and the cycle is repeated until the cells have been transformed and edited by a desired number of, e.g., editing cassettes. The multi-module cell processing instrument exemplified in FIG. 5 is controlled by a processor 524 configured to operate the instrument based on user input or is controlled by one or more scripts including at least one script associated with the reagent cartridge. The processor 524 may control the timing, duration, and temperature of various processes, the dispensing of reagents, and other operations of the various modules of the instrument 500. For example, a script or the processor may control the dispensing of cells, reagents, vectors, and editing oligonucleotides; which editing oligonucleotides are used for cell editing and in what order; the time, temperature and other conditions used in the recovery and expression module, the wavelength at which OD is read in the cell growth module, the target OD to which the cells are grown, and the target time at which the cells will reach the target OD. In addition, the processor may be programmed to notify a user (e.g., via an application) as to the progress of the cells in the automated multi-module cell processing instrument.

It should be apparent to one of ordinary skill in the art given the present disclosure that the process described may be recursive and multiplexed; that is, cells may go through the workflow described in relation to FIG. 5, then the resulting edited culture may go through another (or several or many) rounds of additional editing (e.g., recursive editing) with different editing vectors. For example, the cells from round 1 of editing may be diluted and an aliquot of the edited cells edited by editing vector A may be combined with editing vector B, an aliquot of the edited cells edited by editing vector A may be combined with editing vector C, an aliquot of the edited cells edited by editing vector A may be combined with editing vector D, and so on for a second round of editing. After round two, an aliquot of each of the double-edited cells may be subjected to a third round of editing, where, e.g., aliquots of each of the AB-, AC-, AD-edited cells are combined with additional editing vectors, such as editing vectors X, Y, and Z. That is that double-edited cells AB may be combined with and edited by vectors X, Y, and Z to produce triple-edited edited cells ABX, ABY, and ABZ; double-edited cells AC may be combined with and edited by vectors X, Y, and Z to produce triple-edited cells ACX, ACY, and ACZ; and double-edited cells AD may be combined with and edited by vectors X, Y, and Z to produce triple-edited cells ADX, ADY, and ADZ, and so on. In this process, many permutations and combinations of edits can be executed, leading to very diverse cell populations and cell libraries.

In any recursive process, it may be advantageous to "cure" the previous engine and editing vectors (or single engine+editing vector in a single vector system). "Curing" is the process in which one or more vectors used in the prior round of editing is eliminated from the transformed cells. Curing can be accomplished by, e.g., cleaving the vector(s) using a curing plasmid thereby rendering the editing and/or engine vector (or single, combined vector) nonfunctional; diluting the vector(s) in the cell population via cell growth (that is, the more growth cycles the cells go through, the fewer daughter cells will retain the editing or engine vector(s)), or by, e.g., utilizing a heat-sensitive origin of replication on the editing or engine vector (or combined engine+editing vector). The conditions for curing will depend on the mechanism used for curing; that is, in this example, how the curing plasmid cleaves the editing and/or engine vector. For more details about curing, please see U.S. Pat. Nos. 10,837,021; 11,053, 507; and U.S. Ser. No. 17/353, 282, filed 21 Jun. 2021 and U.S. Ser. No. 17/300,518, filed 27 Jul. 2021.

Figure 6:
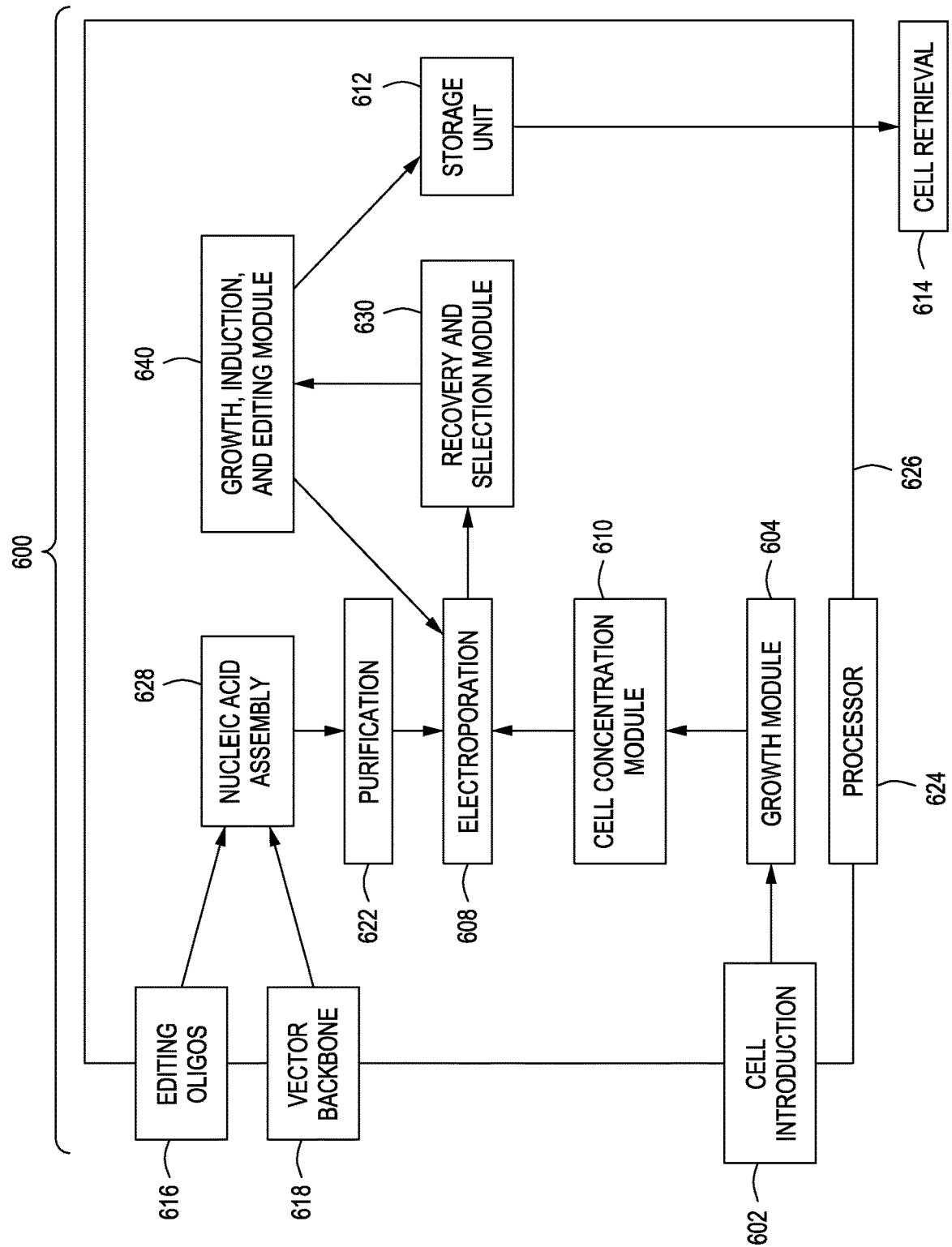
FIG. 6 is a simplified process diagram of an alternative embodiment of an exemplary automated multi-module cell processing instrument useful for recursive cell editing.

FIG. 6 is a simplified block diagram of an embodiment of an alternative exemplary automated multi-module cell processing instrument comprising a bulk liquid growth module for induced editing and enrichment for edited cells. The cell processing instrument 600 may include a housing 626, a reservoir of cells to be transformed or transfected 602, and a growth module (a cell growth device) 604. The cells to be transformed are transferred from a reservoir to the growth module to be cultured until the cells hit a target OD. Once the cells hit the target OD, the growth module may cool or freeze the cells for later processing, or the cells may be transferred to a cell concentration module 630 where the cells are rendered electrocompetent and concentrated to a volume optimal for cell transformation. Once concentrated, the cells are then transferred to an electroporation device 608 (e.g., transformation/transfection module). Exemplary electroporation devices of use in the automated multi-module cell processing instruments for use in the multi-module cell processing instrument include flow-through electroporation devices.

In addition to the reservoir for storing the cells, the system 600 may include a reservoir for storing editing cassettes 616 and a reservoir for storing an expression vector backbone 618. Both the editing oligonucleotide cassettes and the expression vector backbone are transferred from the reagent cartridge to a nucleic acid assembly module 628, where the editing oligonucleotide cassettes are inserted into the expression vector backbone. The assembled nucleic acids may be transferred into an optional purification module 622 for desalting and/or other purification and/or concentration procedures needed to prepare the assembled nucleic acids for transformation. Alternatively, pre-assembled nucleic acids, e.g., an editing vector, may be stored within reservoir 616 or 618. Once the processes carried out by the purification module 622 are complete, the assembled nucleic acids are transferred to, e.g., an electroporation device 608, which already contains the cell culture grown to a target OD and rendered electrocompetent via filtration/cell concentration module 610. In electroporation device 608, the assembled nucleic acids are introduced into the cells. Following electroporation, the cells are transferred into a combined recovery/selection module 630. For examples of multi-module cell editing instruments, see U.S. Pat. Nos. 10,253,316; 10,329,559; 10,323,242; 10,421,959; 10,465,185; 10,519,437; 10,947,532; 10,584,333; 10,584,334; 10,647,982; 10,689,645; 10,738,301; 10,738,663; 10,894,958; 10,954,512; and 11,034,953, all of which are herein incorporated by reference in their entirety.

Following recovery, and, optionally, selection, the cells are transferred to a growth, induction, and editing module (bulk liquid culture) 640. The cells are allowed to grow until the cells reach the stationary growth phase (or nearly so), then editing is induced by induction of transcription of one or both of the nuclease and gRNA. In some embodiments, editing is induced by transcription of one or both of the nuclease and the gRNA being under the control of an inducible promoter. In some embodiments, the inducible promoter is a pL promoter where the promoter is activated by a rise in temperature and "deactivated" by lowering the temperature.

The recovery, selection, growth, induction, editing and storage modules may all be separate, may be arranged and combined as shown in FIG. 6, or may be arranged or combined in other configurations. In certain embodiments, recovery and selection are performed in one module, and growth, editing, and re-growth are performed in a separate module. Alternatively, recovery, selection, growth, editing, and re-growth are performed in a single module.

Once the cells are edited and re-grown (e.g., recovered from editing), the cells may be stored, e.g., in a storage module 612, where the cells can be kept at, e.g., 4° C. until the cells are used in another round of editing or the cells may be retrieved at the cell retrieval 614. The multi-module cell processing instrument is controlled by a processor 624 configured to operate the instrument based on user input, as directed by one or more scripts, or as a combination of user input or a script. The processor 624 may control the timing, duration, temperature, and operations of the various modules of the system 600 and the dispensing of reagents. For example, the processor 624 may cool the cells post-transformation until editing is desired, upon which time the temperature may be raised to a temperature conducive of genome editing and cell growth. The processor may be programmed with standard protocol parameters from which a user may select, a user may specify one or more parameters manually or one or more scripts associated with the reagent cartridge may specify one or more operations and/or reaction parameters. In addition, the processor may notify the user (e.g., via an application to a smart phone or other device) that the cells have reached the target OD as well as update the user as to the progress of the cells in the various modules in the multi-module system.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example I: Growth in the Cell Growth Module

One embodiment of the cell growth device as described herein was tested against a conventional cell shaker shaking a 5 ml tube and an orbital shaker shaking a 125 ml baffled flask to evaluate cell growth in bacterial and yeast cells. Additionally, growth of a bacterial cell culture and a yeast cell culture was monitored in real time using an embodiment of the cell growth module shown in the integrated instrument described herein in relation to FIGS. 2A-2C.

Figure 7:
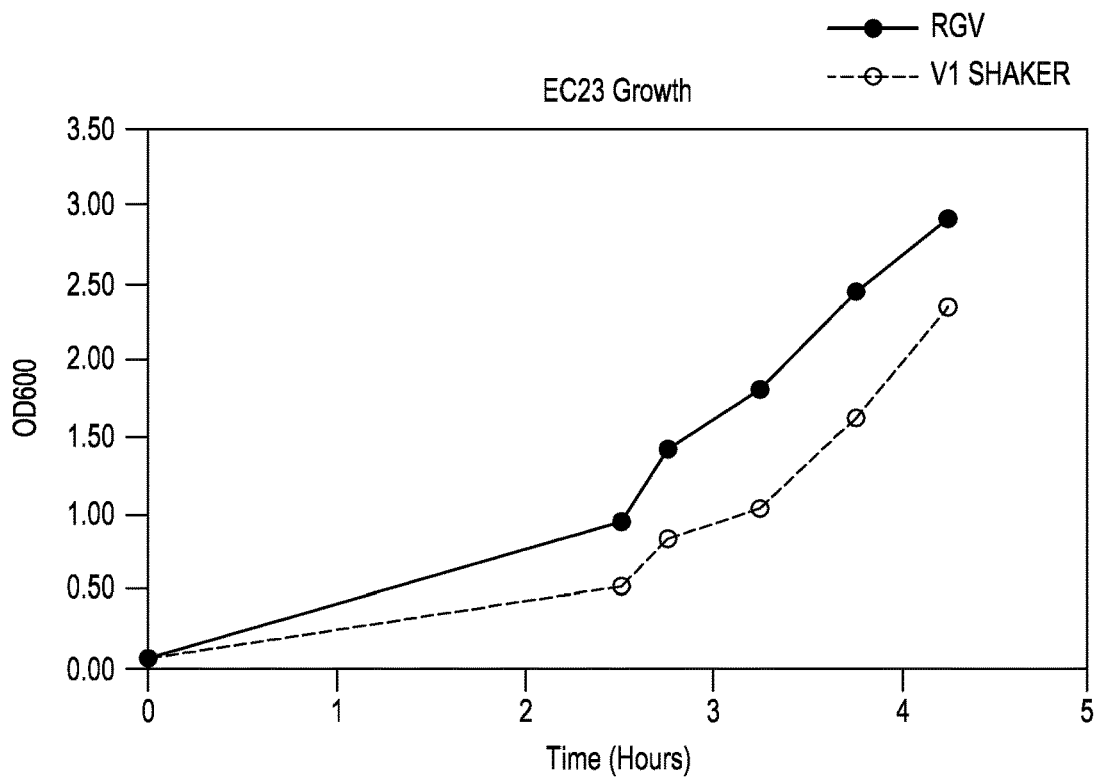
FIG. 7 is a graph demonstrating the effectiveness of a 2-paddle rotating growth vial and cell growth device as described herein for growing an EC23 cell culture vs. a conventional cell shaker.
Figure 8:
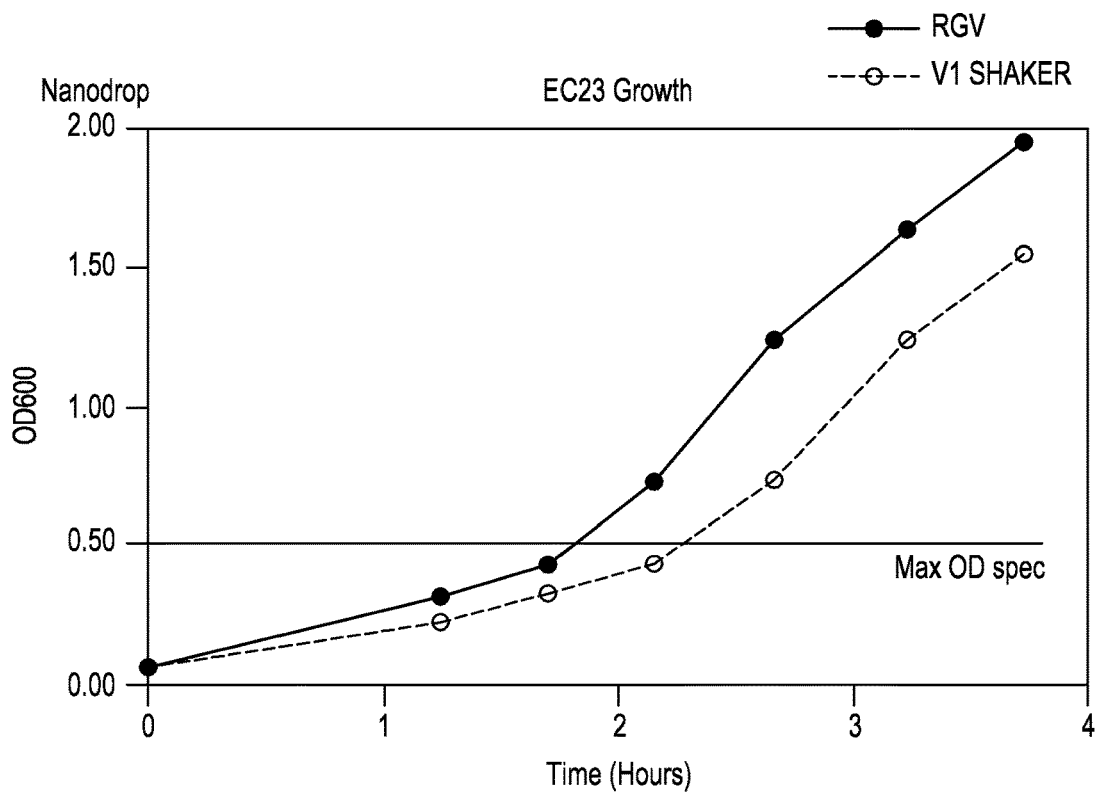
FIG. 8 is a graph demonstrating the effectiveness of a 3-paddle rotating growth vial and cell growth device as described herein for growing an EC23 cell culture vs. a conventional cell shaker.

In a first example, 20 ml EC23 cells (*E. coli* cells) in LB were grown in a 35 ml rotating growth vial with a 2-paddle configuration at 30° C. using the cell growth device as described herein. The rotating growth vial was spun at 600 rpm and oscillated (i.e., the rotation direction was changed) every 1 second. In parallel, 5 ml EC23 cells in LB were grown in a 5 ml tube at 30° C. and were shaken at 750 rpm. $OD_{600}$ was measured at intervals using a NanoDrop™ spectrophotometer (Thermo Fisher Scientific, (Waltham, Mass., USA)). The results are shown in FIG. 7. The rotating growth vial/cell growth device performed better than the cell shaker in growing the cells to $OD_{600}$ 3.0 in slightly over 4 hours. Another experiment was performed with the same conditions (volumes, cells, oscillation) the only difference being a 3-paddle rotating growth vial was employed with the cell growth device, and the results are shown in FIG. 8. Again, the rotating growth vial/cell growth device performed better than the cell shaker in growing the cells to $OD_{600}$ 1.9.

Figure 9:
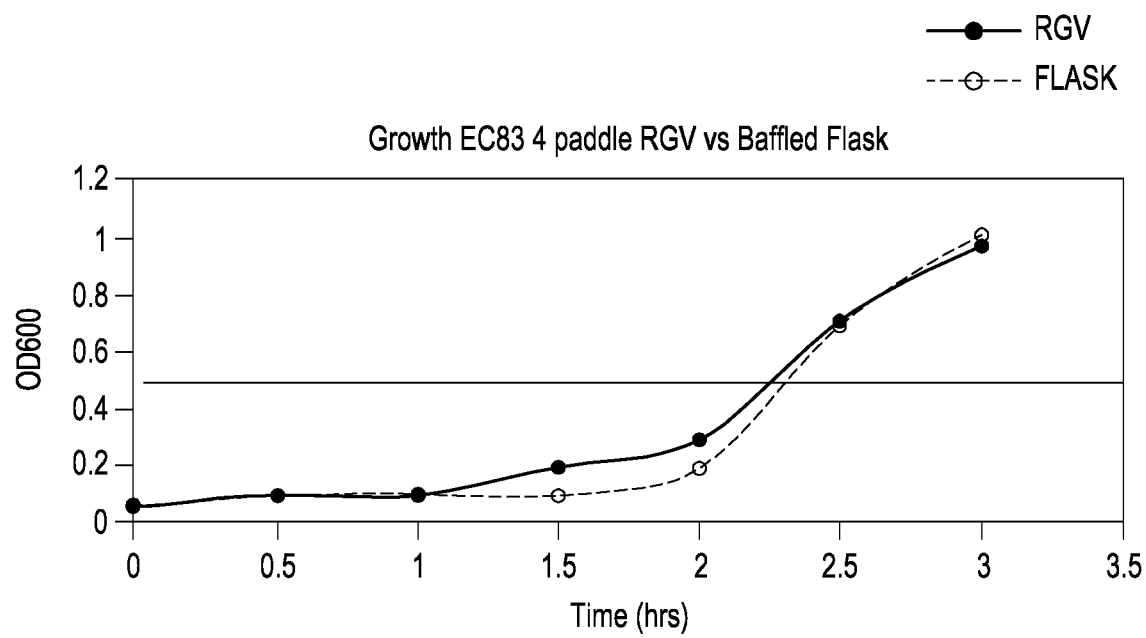
FIG. 9 is a graph demonstrating the effectiveness of a 4-paddle rotating growth vial and cell growth device as described herein for growing an EC83 cell culture vs. a conventional baffled flask.
Figure 10:
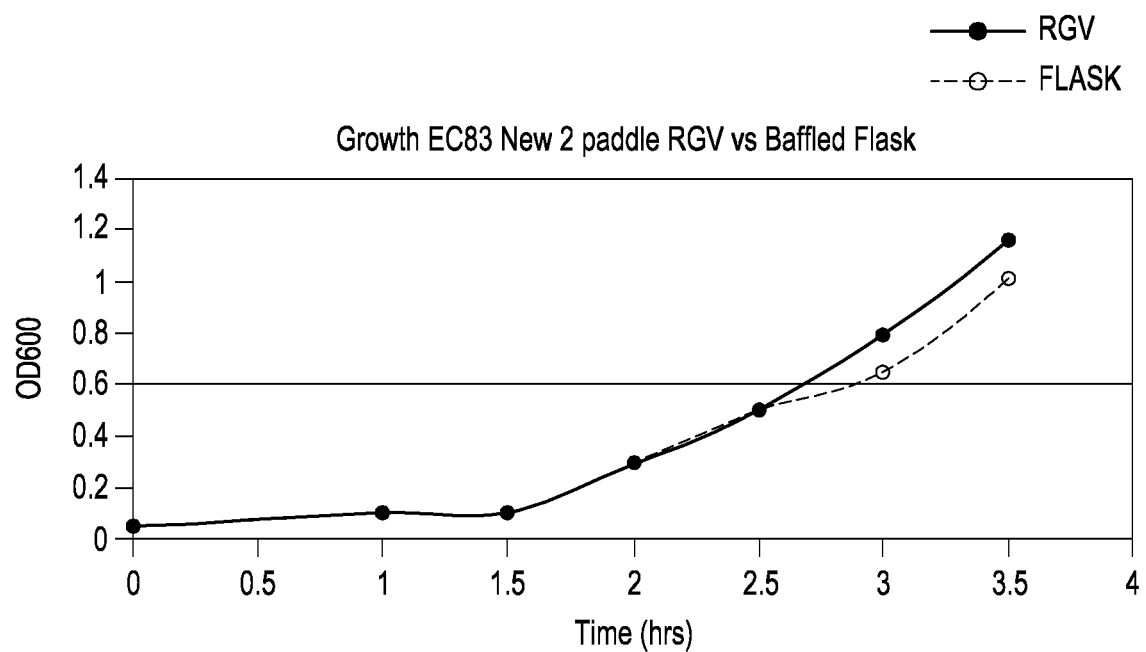
FIG. 10 is a graph demonstrating the effectiveness of a 2-paddle rotating growth vial and cell growth device as described herein for growing an EC83 cell culture vs. a conventional baffled flask.

Two additional experiments were performed, this time comparing the rotating growth vial/cell growth device to a baffled flask and an orbital shaker. In one experiment, 20 ml EC138 cells (*E. coli* cells) in LB were grown in a 35 ml rotating growth vial with a 4-paddle configuration at 30° C. The rotating growth vial was spun at 600 rpm and oscillated (i.e., the rotation direction was changed) every 1 second. In parallel, 20 ml EC138 cells in LB were grown in a 125 ml baffled flask at 30° C. using an orbital shaker. $OD_{600}$ was measured at intervals using a NanoDrop™ spectrophotometer (Thermo Fisher Scientific (Waltham, Mass., USA)). The results are shown in FIG. 9, demonstrating that the rotating growth vial/cell growth device performed as well as the orbital shaker in growing the cells to $OD_{600}$ 1.0. In a second experiment 20 ml EC138 cells (*E. coli* cells) in LB were grown in a 35 ml rotating growth vial with a 2-paddle configuration at 30° C. using the cell growth device as described herein. The rotating growth vial was spun at 600 rpm and oscillated (i.e., the rotation direction was changed) every 1 second. In parallel, 20 ml EC138 cells in LB were grown in a 125 ml baffled flask at 30° C. using an orbital shaker. $OD_{600}$ was measured at intervals using a Nano-Drop™ spectrophotometer (Thermo Fisher Scientific (Waltham, Mass., USA)). The results are shown in FIG. 10, demonstrating that the rotating growth vial/cell growth device performed as well—or better—as the orbital shaker in growing the cells to $OD_{600}$ 1.2.

Figure 11:
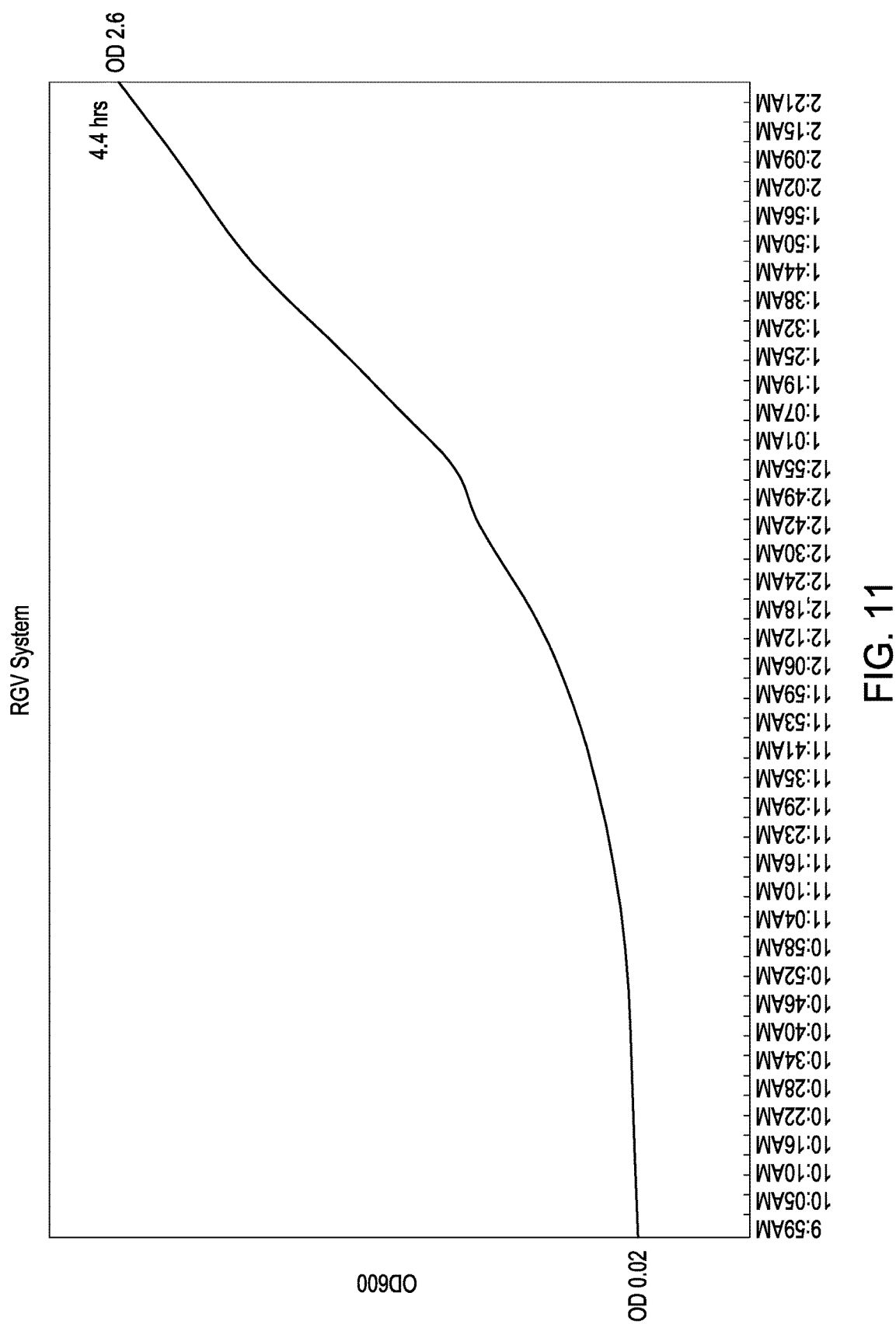
FIG. 11 is a graph demonstrating real-time monitoring of growth of an EC83 cell culture to $OD_{600}$ employing the cell growth device as described herein where a 2-paddle rotating growth vial was used.

In yet another experiment, the rotating growth vial/cell growth device was used to measure $OD_{600}$ in real time. FIG. 11 is a graph showing the results of real time measurement of growth of an EC138 cell culture at 30° C. using oscillating rotation and employing a 2-paddle rotating growth vial. Note that $OD_{600}$ 2.6 was reached in 4.4 hours.

Figure 12:
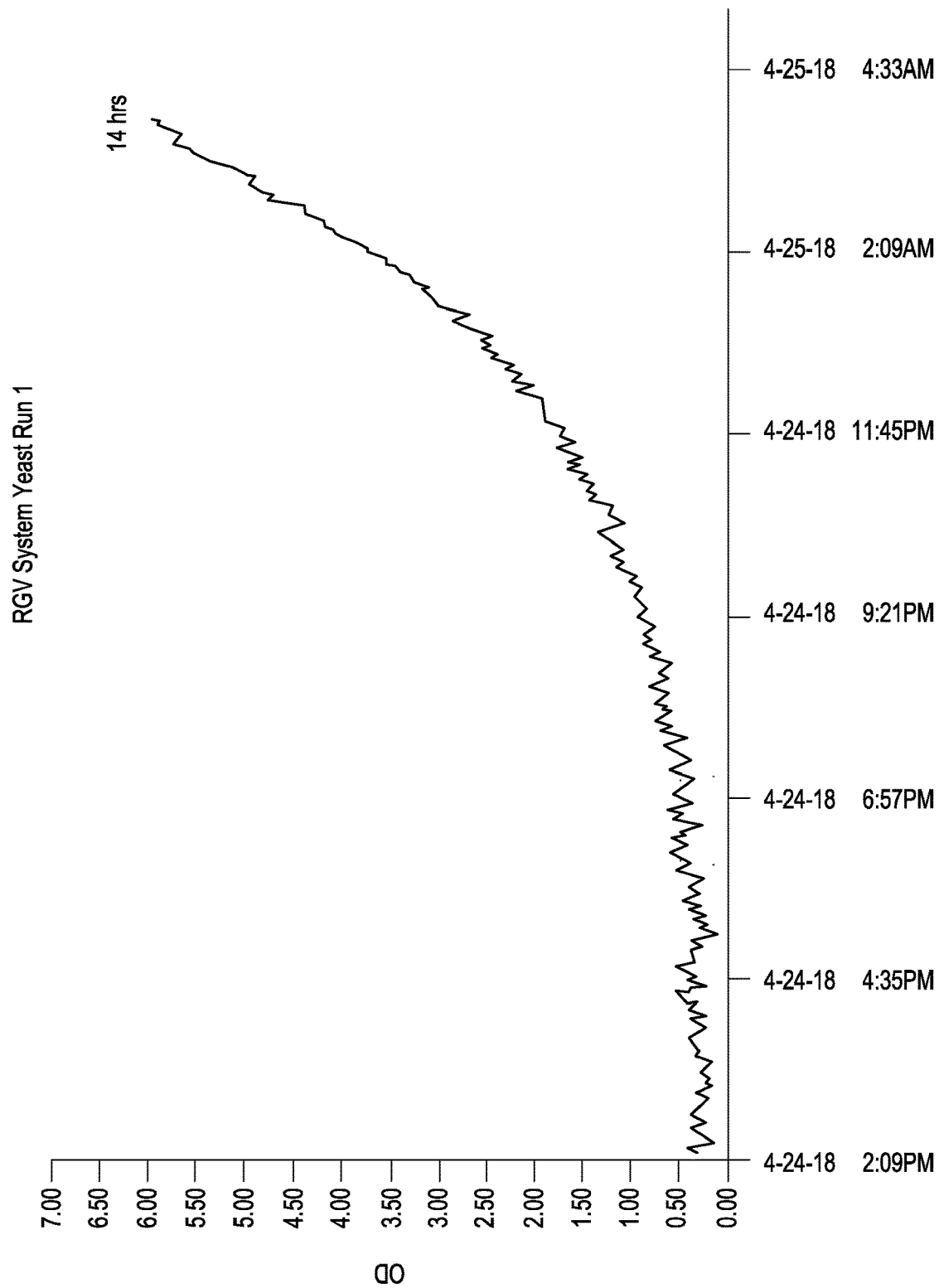
FIG. 12 is a graph demonstrating real-time monitoring of growth of s288c yeast cell culture $OD_{600}$ employing the cell growth device as described herein where a 2-paddle rotating growth vial was used.

In another experiment, the rotating growth vial/cell growth device was used to measure $OD_{600}$ in real time of yeast s288c cells in YPAD medium. The cells were grown at 30° C. using oscillating rotation and employing a 2-paddle rotating growth vial. FIG. 12 is a graph showing the results. Note that $OD_{600}$ 6.0 was reached in 14 hours.

Example II: Cell Concentration

The TFF module as described above in relation to the automated cell processing instrument in FIGS. 2A-2C has been used successfully to process and perform buffer exchange on both *E. coli* and yeast cultures. See U.S. Ser. No. 16/798,302, filed 22 Feb. 2020. In concentrating an *E. coli* culture, the following steps were performed:

First, a 20 ml culture of *E. coli* in LB grown to OD 0.5-0.62 was passed through the TFF device in one direction, then passed through the TFF device in the opposite direction. At this point the cells were concentrated to a volume of approximately 5 ml. Next, 50 ml of 10% glycerol was added to the concentrated cells, and the cells were passed through the TFF device in one direction, in the opposite direction, and back in the first direction for a total of three passes. Again the cells were concentrated to a volume of approximately 5 ml. Again, 50 ml of 10% glycerol was added to the 5 ml of cells and the cells were passed through the TFF device for three passes. This process was repeated; that is, again 50 ml 10% glycerol was added to cells concentrated to 5 ml, and the cells were passed three times through the TFF device. At the end of the third pass of the three 50 ml 10% glycerol washes, the cells were again concentrated to approximately 5 ml of 10% glycerol. The cells were then passed in alternating directions through the TFF device three more times, wherein the cells were concentrated into a volume of approximately 400 μl.

Figure 13A:
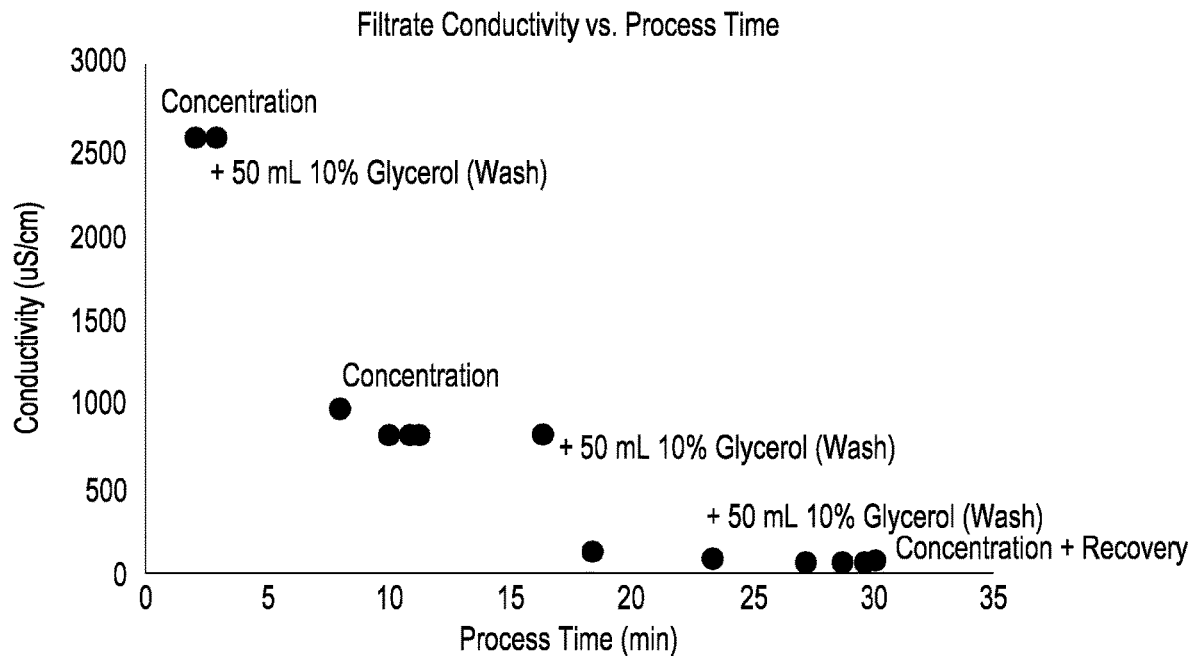
FIG. 13A is a graph plotting filtrate conductivity against filter processing time for an *E. coli* culture processed in the cell concentration device/module described herein.

Filtrate conductivity and filter processing time was measured for *E. coli* with the results shown in FIG. 13A. Filter performance was quantified by measuring the time and number of filter passes required to obtain a target solution electrical conductivity. Cell retention was determined by comparing the optical density (OD600) of the cell culture both before and after filtration. Filter health was monitored by measuring the transmembrane flow rate during each filter pass. Target conductivity (~16 μS/cm) was achieved in approximately 30 minutes utilizing three 50 ml 10% glycerol washes and three passes of the cells through the device for each wash. The volume of the cells was reduced from 20 ml to 400 μl, and recovery of approximately 90% of the cells has been achieved.

Figure 13B:
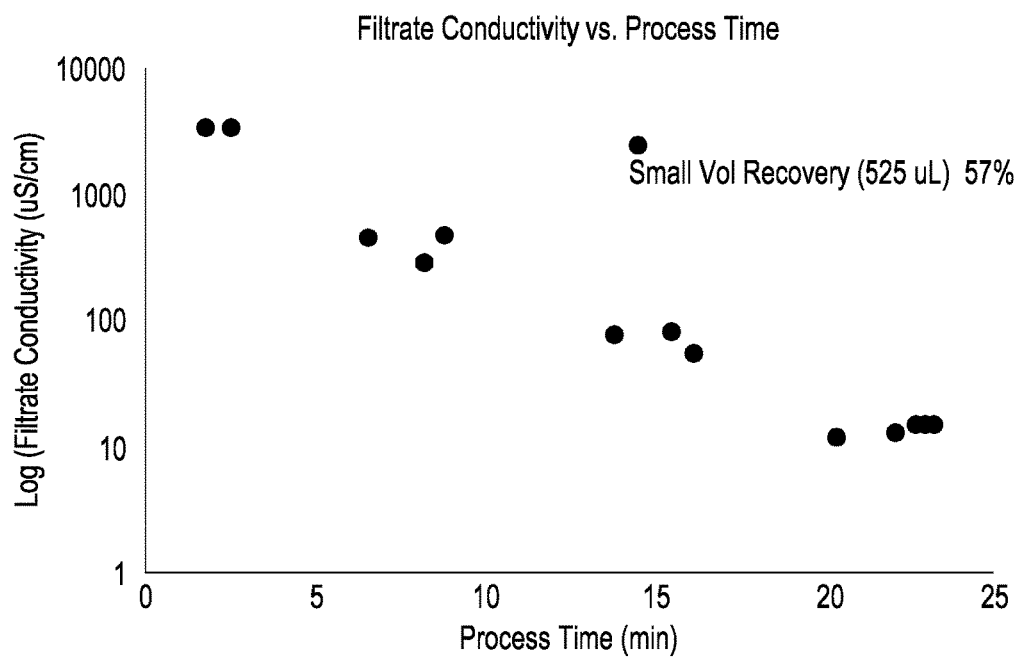
FIG. 13B is a graph plotting filtrate conductivity against filter processing time for a yeast culture processed in the cell concentration device/module described herein.

The same process was repeated with yeast cell cultures. A yeast culture was initially concentrated to approximately 5 ml using two passes through the TFF device in opposite directions. The cells were washed with 50 ml of 1 M sorbitol three times, with three passes through the TFF device after each wash. After the third pass of the cells following the last wash with 1 M sorbitol, the cells were passed through the TFF device two times, wherein the yeast cell culture was concentrated to approximately 525 μl. FIG. 13B presents the filter buffer exchange performance for yeast cells determined by measuring filtrate conductivity and filter processing time. Target conductivity (~10 μS/cm) was achieved in approximately 23 minutes utilizing three 50 ml 1M sorbitol washes and three passes through the TFF device for each wash. The volume of the cells was reduced from 20 ml to 525 μl. Recovery of approximately 90% of the cells has been achieved.

Example III: Production and Transformation of Electrocompetent *E. coli* and *S. cerevisiae*

For testing transformation of the FTEP device, electrocompetent *E. coli* cells were created. To create a starter culture, 6 ml volumes of LB chlor-25 (LB with 25 μg/ml chloramphenicol) were transferred to 14 ml culture tubes. A 25 μl aliquot of *E. coli* was used to inoculate the LB chlor-25 tubes. Following inoculation, the tubes were placed at a 45° angle in the shaking incubator set to 250 RPM and 30° C. for overnight growth, between 12-16 hrs. The OD600 value should be between 2.0 and 4.0. A 1:100 inoculum volume of the 250 ml LB chlor-25 tubes were transferred to four sterile 500 ml baffled shake flasks, i.e., 2.5 ml per 250 ml volume shake flask. The flasks were placed in a shaking incubator set to 250 RPM and 30° C. The growth was monitored by measuring OD600 every 1 to 2 hrs. When the $OD_{600}$ of the culture was between 0.5-0.6 (approx. 3-4 hrs), the flasks were removed from the incubator. The cells were centrifuged at 4300 RPM, 10 min, 4° C. The supernatant was removed, and 100 ml of ice-cold 10% glycerol was transferred to each sample. The cells were gently resuspended, and the wash procedure performed three times, each time with the cells resuspended in 10% glycerol. After the fourth centrifugation, the cell resuspension was transferred to a 50 ml conical Falcon tube and additional ice-cold 10% glycerol added to bring the volume up to 30 ml. The cells were again centrifuged at 4300 RPM, 10 min, 4° C., the supernatant removed, and the cell pellet resuspended in 10 ml ice-cold glycerol. The cells were aliquoted in 1:100 dilutions of cell suspension and ice-cold glycerol.

The comparative electroporation experiment was performed to determine the efficiency of transformation of the electrocompetent *E. coli* using the FTEP device described. The flow rate was controlled with a pressure control system. The suspension of cells with DNA was loaded into the FTEP inlet reservoir. The transformed cells flowed directly from the inlet and inlet channel, through the flow channel, through the outlet channel, and into the outlet containing recovery medium. The cells were transferred into a tube containing additional recovery medium, placed in an incubator shaker at 30° C. shaking at 250 rpm for 3 hours. The cells were plated to determine the colony forming units (CFUs) that survived electroporation and failed to take up a plasmid and the CFUs that survived electroporation and took up a plasmid. Plates were incubated at 30° C.; *E. coli* colonies were counted after 24 hrs.

Figure 14A:
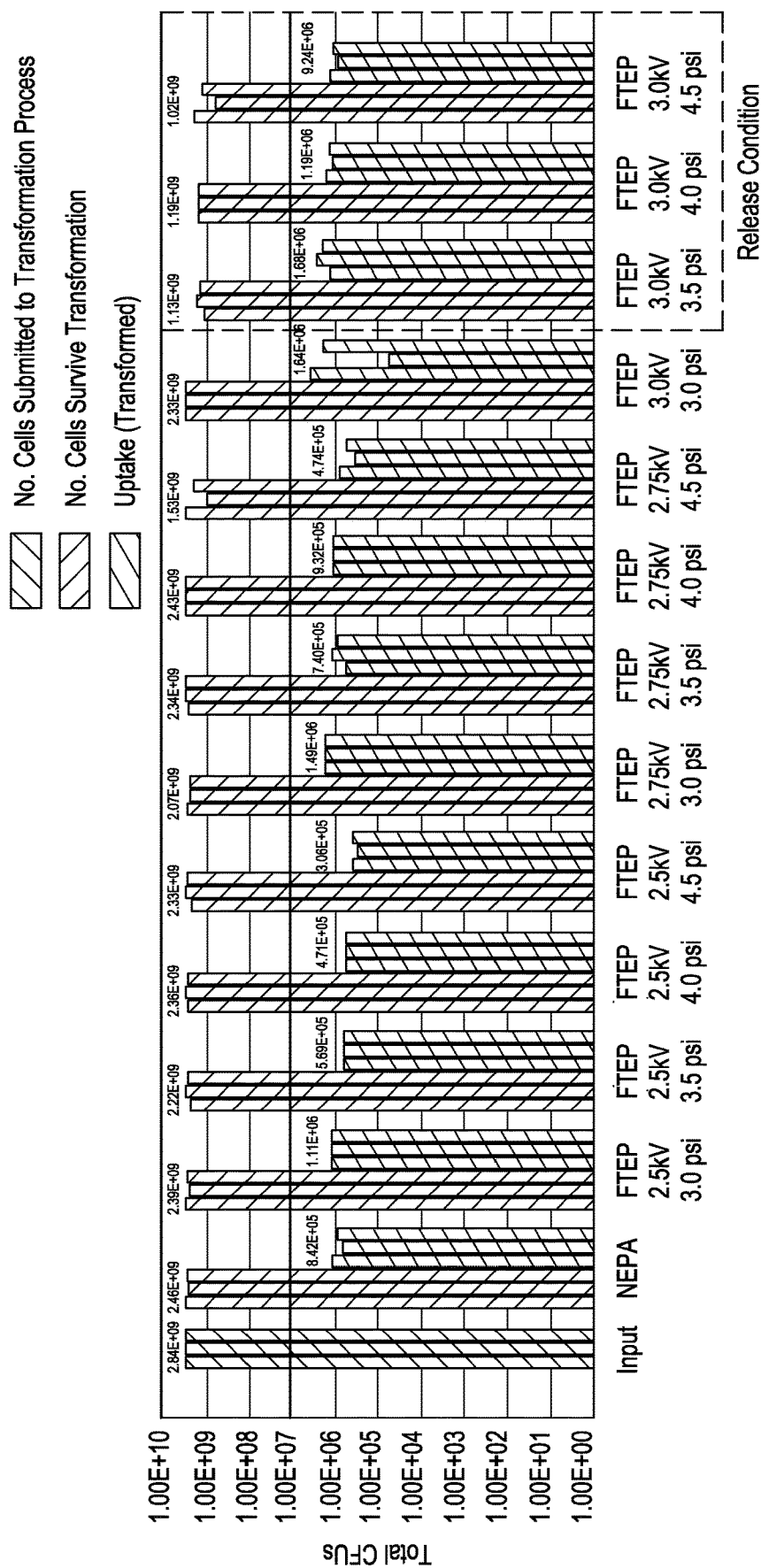
FIG. 14A is a bar graph showing the results of electroporation of *E. coli* using a flow through electroporation device (FTEP) and a comparator electroporation device.

The flow-through electroporation experiments were benchmarked against 2 mm electroporation cuvettes (Bulldog Bio, Portsmouth, N.H., USA) using an in vitro high voltage electroporator (NEPAGENE™ ELEPO21). Stock tubes of cell suspensions with DNA were prepared and used for side-to-side experiments with the NEPAGENE™ and the flow-through electroporation. The results are shown in FIG. 14A. In FIG. 14A, the left-most bars hatched /// denote cell input, the bars to the left bars hatched \\\ denote the number of cells that survived transformation, and the right bars hatched /// denote the number of cells that were actually transformed. The FTEP device showed equivalent transformation of electrocompetent E. coli cells at various voltages as compared to the NEPAGENE™ electroporator. As can be seen, the transformation survival rate is at least 90% and in some embodiments is at least 95%, 96%, 97%, 98%, or 99%. The recovery ratio (the fraction of introduced cells which are successfully transformed and recovered) is in certain embodiments at least 0.001 and preferably between 0.00001 and 0.01. In FIG. 14A the recovery ratio is approximately 0.0001.

Figure 14B:
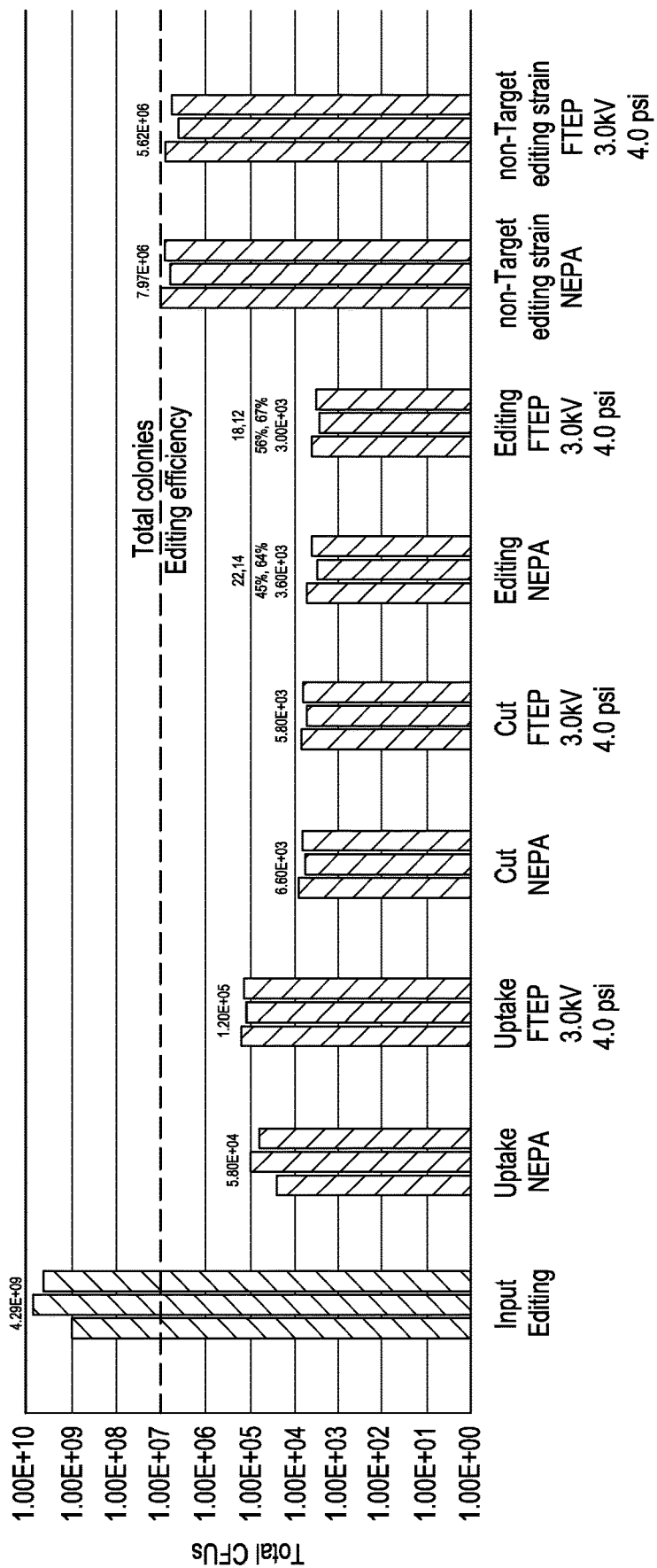
FIG. 14B is a bar graph showing uptake, cutting, and editing efficiencies of *E. coli* cells transformed via an FTEP as described herein benchmarked against a comparator electroporation device.

Additionally, a comparison of the NEPAGENE™ ELEPO21 and the FTEP device was made for efficiencies of transformation (uptake), cutting, and editing. In FIG. 14B, triplicate experiments were performed where the bars hatched /// denote the number of cells input for transformation, and the bars hatched \\\ denote the number of cells that were transformed (uptake), the number of cells where the genome of the cells was cut by a nuclease transcribed and translated from a vector transformed into the cells (cutting), and the number of cells where editing was effected (cutting and repair using a nuclease transcribed and translated from a vector transformed into the cells, and using a guide RNA and a repair template sequence both of which were transcribed from a vector transformed into the cells). Again, it can be seen that the FTEP showed equivalent transformation, cutting, and editing efficiencies as the NEPAGENE™ electroporator. The recovery rate in FIG. 14B for the FTEP is greater than 0.001.

For testing transformation of the FTEP device in yeast, S. cerevisiae cells were created using the methods as generally set forth in Bergkessel and Guthrie, Methods Enzymol., 529:311-20 (2013). Briefly, YFAP media was inoculated for overnight growth, with 3 ml inoculate to produce 100 ml of cells. Every 100 ml of culture processed resulted in approximately 1 ml of competent cells. Cells were incubated at 30° C. in a shaking incubator until they reached an OD600 of 1.5+/−0.1.

A conditioning buffer was prepared using 100 mM lithium acetate, 10 mM dithiothreitol, and 50 mL of buffer for every 100 mL of cells grown and kept at room temperature. Cells were harvested in 250 ml bottles at 4300 rpm for 3 minutes, and the supernatant removed. The cell pellets were suspended in 100 ml of cold 1 M sorbitol, spun at 4300 rpm for 3 minutes and the supernatant once again removed. The cells were suspended in conditioning buffer, then the suspension transferred into an appropriate flask and shaken at 200 RPM and 30° C. for 30 minutes. The suspensions were transferred to 50 ml conical vials and spun at 4300 rpm for 3 minutes. The supernatant was removed and the pellet resuspended in cold 1 M sorbitol. These steps were repeated three times for a total of three wash-spin-decant steps. The pellet was suspended in sorbitol to a final OD of 150+/−20.

A comparative electroporation experiment was performed to determine the efficiency of transformation of the electrocompetent S. cerevisiae using the FTEP device. The flow rate was controlled with a syringe pump (Harvard Apparatus PHD ULTRA™ 4400, Holliston, Mass., USA). The suspension of cells with DNA was loaded into a 1 mL glass syringe (Hamilton 81320 Syringe, PTFE Luer Lock) before mounting on the pump. The output from the function generator was turned on immediately after starting the flow. The processed cells flowed directly into a tube with 1M sorbitol with carbenicillin. Cells were collected until the same volume electroporated in the NEPAGENE™ had been processed, at which point the flow and the output from the function generator were stopped. After a 3-hour recovery in an incubator shaker at 30° C. and 250 rpm, cells were plated to determine the colony forming units (CFUs) that survived electroporation and failed to take up a plasmid and the CFUs that survived electroporation and took up a plasmid. Plates were incubated at 30° C. Yeast colonies are counted after 48-76 hrs.

Figure 15:
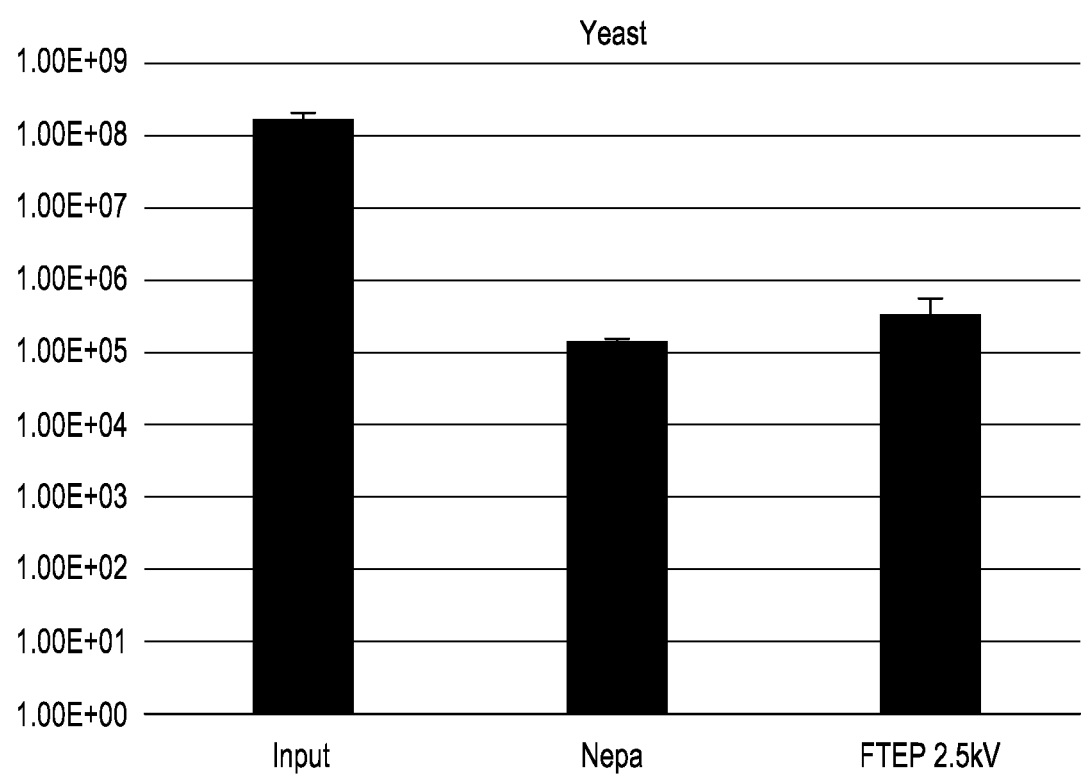
FIG. 15 is a bar graph showing the results of electroporation of *S. cerevisiae* using an FTEP device of the disclosure and a comparator electroporation method.

The flow-through electroporation experiments were benchmarked against 2 mm electroporation cuvettes (Bulldog Bio, Portsmouth, N.H., USA) using an in vitro high voltage electroporator (NEPAGENE™ ELEPO21). Stock tubes of cell suspensions with DNA were prepared and used for side-to-side experiments with the NEPAGENE™ and the flow-through electroporation. The results are shown in FIG. 15. The device showed better transformation and survival of electrocompetent S. Cerevisiae at 2.5 kV voltages as compared to the NEPAGENE™ method. Input is total number of cells that were processed.

Example IV: Bulk Liquid Protocol: Induction and Outgrowth 250 mL baffled shake flasks were prepared with 50 mL of SOB+100 µg/mL carbenicillin and 25 µg/mL chloramphenicol. For a full, deconvolution experiment three shake flasks were prepared per transformation. 500 µL of undiluted culture from each transformation reaction was transferred into the prepared 250 mL shake flasks. The following temperature settings were set up on an incubator: 30° C. for 9 hours→42° C. for 2 hours→30° C. for 9 hours. This temperature regime was used to allow for additional recovery of the cells from transformation during the first eight hours. The λred system was induced one hour prior to induction of the nuclease, where λ induction was triggered by the addition of arabinose (2.5 mL of 20% arabinose) to the culture, and the nuclease induction was triggered by increasing the temperature of the cultures to 42° C. For full deconvolution experiments, arabinose was not added to the UPTAKE and CUT flasks as those should not express lambda red; further, the UPTAKE flasks were not shifted to 42° C.

After the temperature cycling is complete (~21 hours), the shake flasks were removed. For NGS-SinglePlex: serial dilutions of $10^{-5}$ to $10^{-7}$ of each culture were prepared with 0.8% NaCl (50 µL of culture into 450 µL of sterile, 0.8% NaCl). Following dilution, 300 µL of each dilution was plated onto 150 mm LB agar plates with standard concentrations of chloramphenicol and carbenicillin. The plates were then placed in a 30° C. incubator for overnight growth and were picked for singleplex NGS the following day. For NGS-Amplicon: 250 µL of culture from each shake flask was removed and used as the input for a plasmid extraction protocol. The OD of this culture was measured to select a volume based on the desired number of cells to go into the plasmid purification. Optionally, an undiluted volume from each shake flask may be plated to see enrichment/depletion of cassettes and the plates were scraped the following day and processed.

Figure 16:
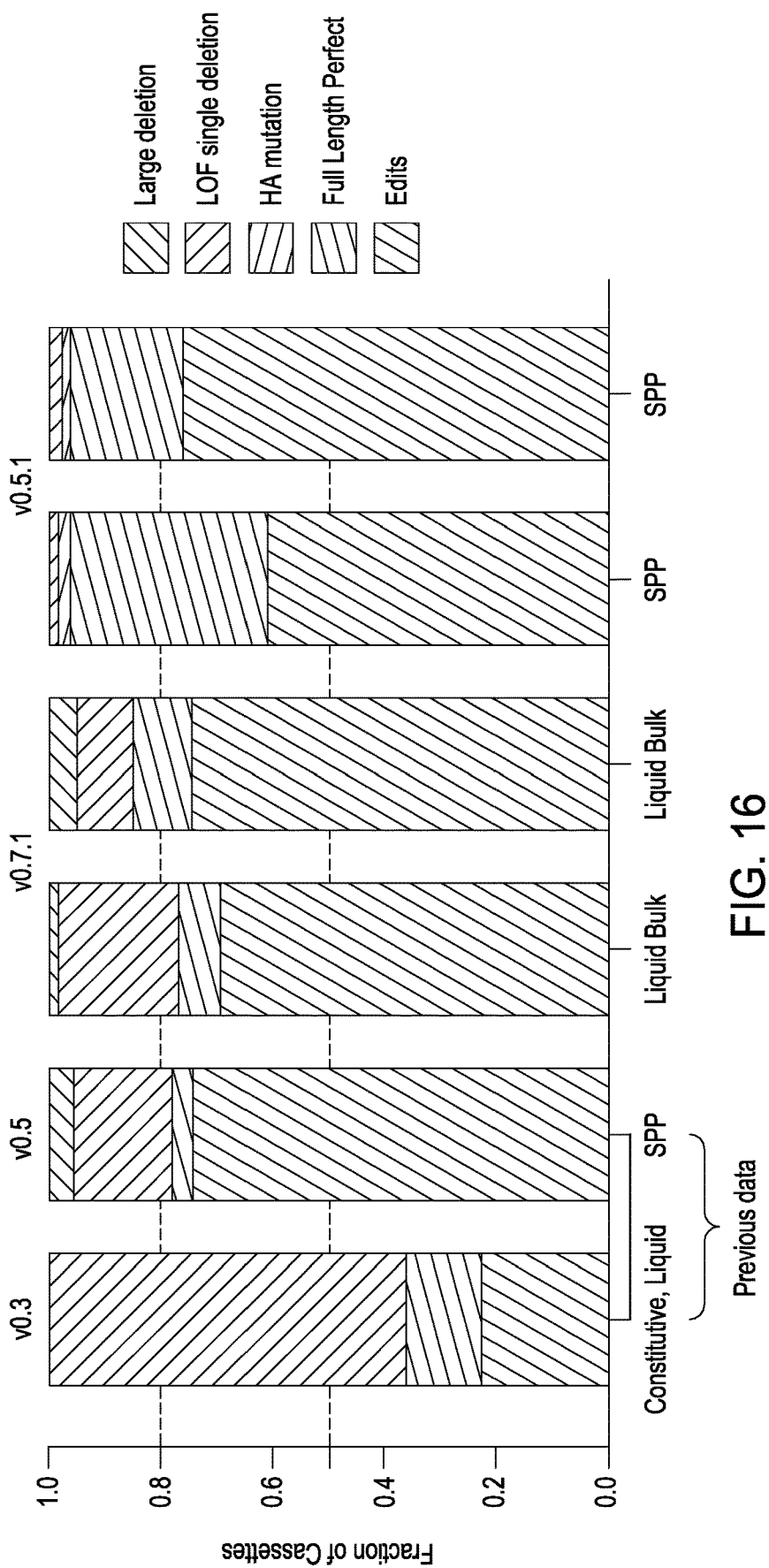
FIG. 16 is a graph showing the editing results obtained via the liquid bulk method for increasing observed editing in live cells.

FIG. 16 is a bar graph showing the various types of edits observed using constitutive editing in a liquid culture (approximately 20% editing observed), standard plating procedure (approximately 76% editing observed), two replica experiments of induced editing in liquid bulk (approximately 70% and 76% editing observed), and two replica experiments of induced editing using the standard plating procedure (approximately 60% and 76% editing observed). Editing clonality was also measured. The editing clonality of the standard plating procedure showed mixed clonality for the 96 wells, with some colonies achieving 100% clonality, most colonies achieving greater than 50% clonality, and an average clonality of 70% and 60% for two replicates (data not shown). The editing clonality of the liquid bulk protocol shows that the majority of the cells were either 100% edited, or 0% edited (e.g., wildtype), with a small number (approximately 8%) between 100% or 0%. The average editing efficiency was similar for these protocols.

Example V: Singulation, Growth and Editing of *E. coli* in 200 K SWIIN

A singleplex automated genomic editing using MAD7 nuclease, a library with 94 different edits in a single gene (yagP) and employing a 200K singulation device such as those exemplified in U.S. Pat. Nos. 10,533,152; 10,532,324; 10,550,363; 10,625,212; 10,663,626; 10,633,627; 10,647,958; 10,760,043; 10,723,995; 10,844,344; 10,801,008; 10,851,339; 11,046,928; 10,954,485; 11,072,774; 10,774,463; 10,835,869 and 10,752,874 was carried out. The engine vector used comprised MAD7 under the control of the pL inducible promoter, and the editing vector used comprised the editing cassette being under the control of the pL inducible promoter, and the λ Red recombineering system under control of the pBAD inducible promoter pBAD—with the exception that the editing cassette comprises the 94 yagP gene edits (repair templates) and the appropriate corresponding gRNAs. Two SWIIN workflows were compared, and further were benchmarked against the standard plating protocol. The SWIIN protocols differ from one another that in one set of replicates LB medium containing arabinose was used to distribute the cells in the SWIIN (arabinose was used to induce the λ Red recombineering system (which allows for repair of double-strand breaks in *E. coli* that are created during editing), and in the other set of replicates SOB medium without arabinose was used to distribute the cells in the SWIIN and for initial growth, with medium exchange performed to replace the SOB medium without arabinose with SOB medium with arabinose. Approximately 70K cells were loaded into the 200 K SWIIN.

Figure 17:
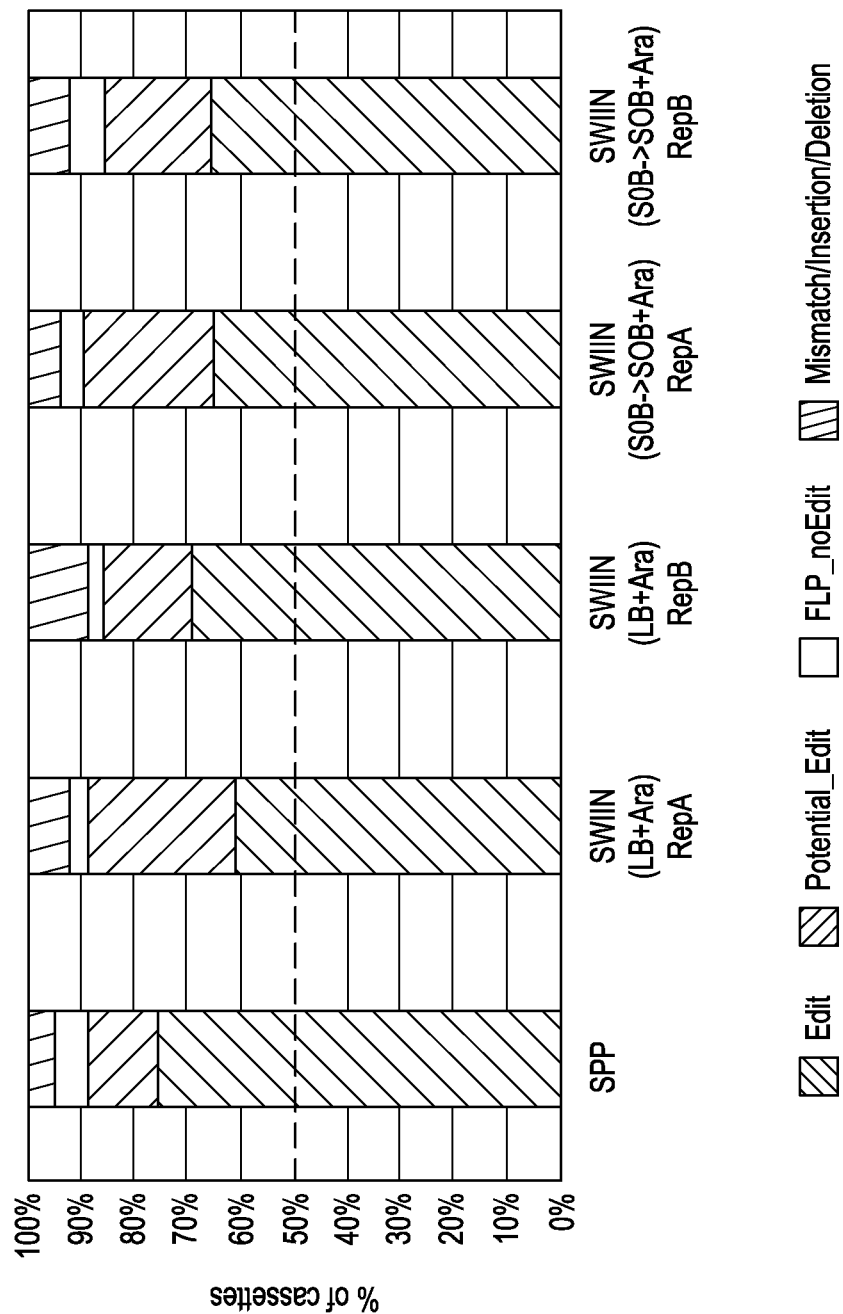
FIG. 17 is a graph comparing the percentage of editing obtained for a standard plating protocol (SPP), and replicate samples using two different conditions in a solid wall isolation, induction, and normalization device (SWIIN): the first with LB+ arabinose; and the second with SOB followed by SOB+ arabinose.

In all protocols (standard plating, LB-SWIIN, and SOB-SWIIN), the cells were allowed to grow at 30° C. for 9 hours and editing was induced by raising the temperature to 42° C. for 2.5 hours, then the temperature was returned to 30° C. and the cells were grown overnight. The results of this experiment are shown in FIG. 17 and in Table 1 below. Note that similar editing performance was observed with the four replicates of the two SWIIN workflows, indicating that the performance of SWIIN plating with and without arabinose in the initial medium is similar. Editing percentage in the standard plating protocol was approximately 77%, in bulk liquid was approximately 67%, and for the SWIIN replicates ranged from approximately 63% to 71%. Note that the percentage of unique edit cassettes divided by the total number of edit cassettes was similar for each protocol.

TABLE 1

|  | Standard Plating | SWIIN LB/Ara Rep. A | SWIIN LB/Ara Rep. B | SWIIN SOB then SOB/Ara Rep. A | SWIIN SOB then SOB/Ara Rep. B |
|---|---|---|---|---|---|
| 40006 edit calls/ identified wells | 0.777 | 0.633 | 0.719 | 0.663 | 0.695 |
| Unique edit cassettes/ total edit cassettes | 0.49 | 0.49 | 0.43 | 0.50 | 0.51 |

Example VI: MAD7 vs. MAD7-SSBct Fusion Protein Cell Viability

Figure 18:
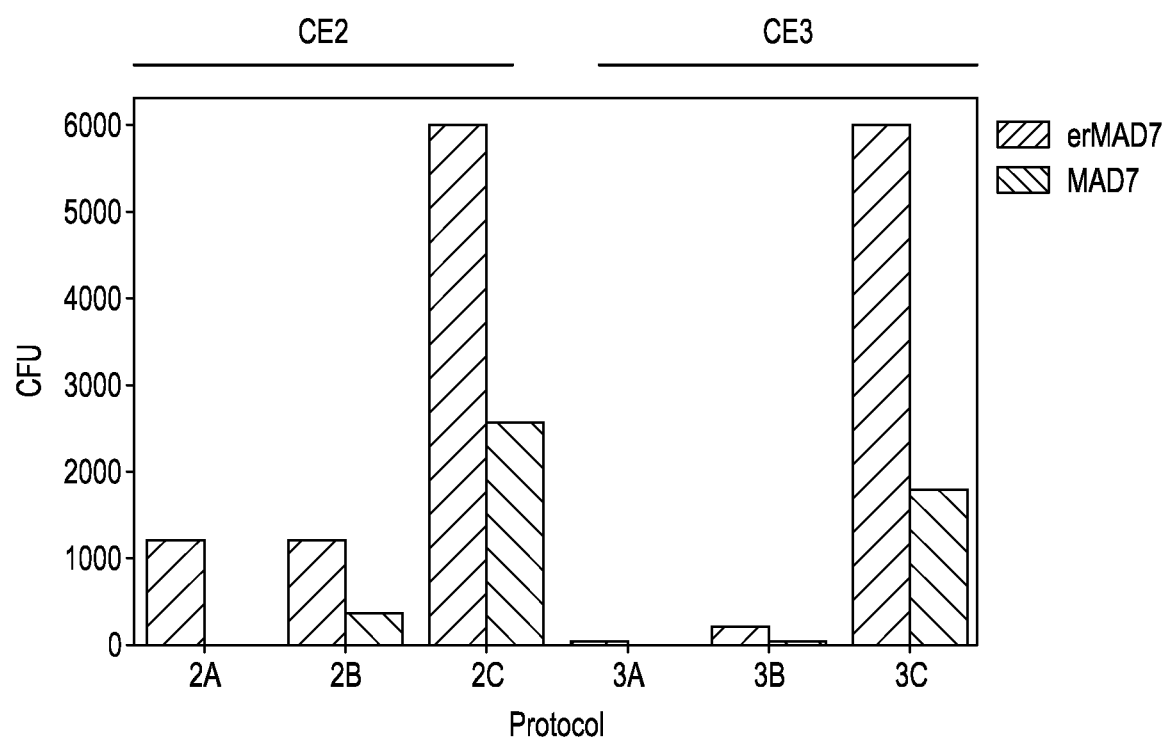
FIG. 18 is a bar graph showing enhanced cell viability using a MAD7-SSBct fusion protein versus MAD7 to edit *E. coli* cells.

FIG. 18 is a bar graph showing the results of cell viability during simultaneous editing of two (CE2) or three (CE3) sites in the *E. coli* genome using either MAD7 or enhanced repair MAD7 ("erMAD7").

Example VII: Fully-Automated Singleplex RGN-Directed Editing Run

Singleplex automated genomic editing using MAD7 nuclease was successfully performed with an automated multi-module instrument of the disclosure. See U.S. Pat. No. 9,982,279; and U.S. Ser. No. 16/024,831 filed 30 Jun. 2018; Ser. No. 16/024,816 filed 30 Jun. 2018; Ser. No. 16/147,353 filed 28 Sep. 2018; Ser. No. 16/147,865 filed 30 Sep. 2018; and Ser. No. 16/147,871 filed 30 Jun. 2018.

An ampR plasmid backbone and a lacZ_F172* editing cassette were assembled via Gibson Assembly™ into an "editing vector" in an isothermal nucleic acid assembly module included in the automated instrument. lacZ_F172 functionally knocks out the lacZ gene. "lacZ_F172*" indicates that the edit happens at the 172nd residue in the lacZ amino acid sequence. Following assembly, the product was de-salted in the isothermal nucleic acid assembly module using AMPure beads, washed with 80% ethanol, and eluted in buffer. The assembled editing vector and recombineering-ready, electrocompetent *E. coli* cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module), and allowed to recover in SOC medium containing chloramphenicol. Carbenicillin was added to the medium after 1 hour, and the cells were allowed to recover for another 2 hours. After recovery, the cells were held at 4° C. until recovered by the user.

After the automated process and recovery, an aliquot of cells was plated on MacConkey agar base supplemented with lactose (as the sugar substrate), chloramphenicol and carbenicillin and grown until colonies appeared. White colonies represented functionally edited cells, purple colonies represented un-edited cells. All liquid transfers were performed by the automated liquid handling device of the automated multi-module cell processing instrument.

The result of the automated processing was that approximately $1.0E^{-03}$ total cells were transformed (comparable to conventional benchtop results), and the editing efficiency was 83.5%. The lacZ_172 edit in the white colonies was confirmed by sequencing of the edited region of the genome of the cells. Further, steps of the automated cell processing were observed remotely by webcam and text messages were sent to update the status of the automated processing procedure.

Example VII: Fully-Automated Recursive Editing Run

Recursive editing was successfully achieved using the automated multi-module cell processing system. An ampR plasmid backbone and a lacZ_V10* editing cassette were assembled via Gibson Assembly® into an "editing vector" in an isothermal nucleic acid assembly module included in the automated system. Similar to the lacZ_F172 edit, the lacZ_V10 edit functionally knocks out the lacZ gene. "lacZ_V10" indicates that the edit happens at amino acid position 10 in the lacZ amino acid sequence. Following assembly, the product was de-salted in the isothermal nucleic acid assembly module using AMPure beads, washed with 80% ethanol, and eluted in buffer. The first assembled editing vector and the recombineering-ready electrocompetent *E. Coli* cells were transferred into a transformation module for electroporation. The cells and nucleic acids were combined and allowed to mix for 1 minute, and electroporation was performed for 30 seconds. The parameters for the poring pulse were: voltage, 2400 V; length, 5 ms; interval, 50 ms; number of pulses, 1; polarity, +. The parameters for the transfer pulses were: Voltage, 150 V; length, 50 ms; interval, 50 ms; number of pulses, 20; polarity, +/−. Following electroporation, the cells were transferred to a recovery module (another growth module) allowed to recover in SOC medium containing chloramphenicol. Carbenicillin was added to the medium after 1 hour, and the cells were grown for another 2 hours. The cells were then transferred to a centrifuge module and a media exchange was then performed. Cells were resuspended in TB containing chloramphenicol and carbenicillin where the cells were grown to OD600 of 2.7, then concentrated and rendered electrocompetent.

During cell growth, a second editing vector was prepared in the isothermal nucleic acid assembly module. The second editing vector comprised a kanamycin resistance gene, and the editing cassette comprised a galK Y145* edit. If successful, the galK Y145* edit confers on the cells the ability to uptake and metabolize galactose. The edit generated by the galK Y154* cassette introduces a stop codon at the 154th amino acid reside, changing the tyrosine amino acid to a stop codon. This edit makes the galK gene product non-functional and inhibits the cells from being able to metabolize galactose. Following assembly, the second editing vector product was de-salted in the isothermal nucleic acid assembly module using AMPure beads, washed with 80% ethanol, and eluted in buffer. The assembled second editing vector and the electrocompetent *E. Coli* cells (that were transformed with and selected for the first editing vector) were transferred into a transformation module for electroporation, using the same parameters as detailed above. Following electroporation, the cells were transferred to a recovery module (another growth module), allowed to recover in SOC medium containing carbenicillin. After recovery, the cells were held at 4° C. until retrieved, after which an aliquot of cells were plated on LB agar supplemented with chloramphenicol, and kanamycin. To quantify both lacZ and galK edits, replica patch plates were generated on two media types: 1) MacConkey agar base supplemented with lactose (as the sugar substrate), chloramphenicol, and kanamycin, and 2) MacConkey agar base supplemented with galactose (as the sugar substrate), chloramphenicol, and kanamycin. All liquid transfers were performed by the automated liquid handling device of the automated multi-module cell processing system.

In this recursive editing experiment, 41% of the colonies screened had both the lacZ and galK edits, the results of which were comparable to the double editing efficiencies obtained using a "benchtop" or manual approach.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A composition for homologous recombination-based editing of live isolated prokaryotic or eukaryotic cells at a target DNA sequence comprising:
    a first editing vector construct comprising:
        a polynucleotide sequence that encodes a fusion protein comprising two domains, the two domains comprising:
            an N-terminal RNA-guided MAD7 endonuclease domain configured to nick or cleave the target DNA sequence; and
            a C-terminal domain consisting of a full or C-terminal portion of a single-strand binding (SSB) protein, the full or C-terminal portion of the SSB protein fused to a C-terminus of the RNA-guided MAD7 endonuclease domain; and
        a polynucleotide sequence that encodes a single-strand DNA annealing protein (SSAP) that is co-expressed with the fusion protein and exhibits binding for the C-terminal domain of the fusion protein;
    a second editing vector construct comprising a cassette, the cassette comprising a polynucleotide sequence that encodes a gRNA transcript and a repair template transcript covalently linked together.

2. The composition of claim 1, wherein the live cells are mammalian cells, bacteria cells, or yeast cells.

3. The composition of claim 2, wherein the live cells are mammalian cells.

4. The composition of claim 2, wherein the live cells are bacterial cells.

5. The composition of claim 1, wherein the SSB protein is EcSSB and the SSAP is Redβ.

6. The composition of claim 1, wherein the SSB protein is EcSSB.

7. The composition of claim 1, wherein the SSAP is Redβ.

8. A composition for homologous recombination-based editing of isolated prokaryotic or eukaryotic cells at a target DNA sequence comprising:
- a polynucleotide sequence that encodes a fusion protein comprising two domains, the two domains comprising:
  - an N-terminal RNA-guided MAD7 endonuclease domain configured to nick or cleave the target DNA sequence; and
  - a C-terminal domain consisting of a full or C-terminal portion of a single-strand binding (SSB) protein, the full or C-terminal portion of the SSB protein fused to a C-terminus of the RNA-guided MAD7 endonuclease domain;
- a polynucleotide sequence that encodes a single-strand DNA annealing protein (SSAP) that exhibits binding for the C-terminal domain of the fusion protein; and
- an editing cassette comprising a polynucleotide sequence that encodes a gRNA transcript and a repair template transcript covalently linked together.

9. The composition of claim 8, wherein the cells are mammalian cells, bacteria cells, or yeast cells.

10. The composition of claim 9, wherein the cells are mammalian cells.

11. The composition of claim 9, wherein the cells are bacteria cells.

12. The composition of claim 9, wherein the cells are yeast cells.

13. The composition of claim 8, wherein the SSB protein is EcSSB.

14. The composition of claim 8, wherein the SSAP is Redβ.

15. The composition of claim 14, wherein the SSB protein is EcSSB.

16. A composition for homologous recombination-based editing of isolated prokaryotic or eukaryotic cells at a target DNA sequence comprising:
- a fusion protein comprising two domains, the two domains comprising:
  - an N-terminal RNA-guided MAD7 endonuclease domain configured to nick or cleave the target DNA sequence; and
  - a C-terminal domain consisting of a full or C-terminal portion of a single-strand binding (SSB) protein, the full or C-terminal portion of the SSB protein fused to a C-terminus of the RNA-guided MAD7 endonuclease domain;
- a single-strand DNA annealing protein (SSAP) that exhibits binding for the C-terminal domain of the fusion protein; and
- a polynucleotide that comprises or encodes a gRNA transcript and a repair template transcript covalently linked together.

17. The composition of claim 16, wherein the cells are mammalian cells, bacteria cells, or yeast cells.

18. The composition of claim 17, wherein the cells are mammalian cells.

19. The composition of claim 17, wherein the cells are bacteria cells.

20. The composition of claim 17, wherein the cells are yeast cells.

21. The composition of claim 16, wherein the SSB protein is EcSSB.

22. The composition of claim 16, wherein the SSAP is Redβ.

23. The composition of claim 22, wherein the SSB protein is EcSSB.

* * * * *